(12) United States Patent
Faull et al.

(10) Patent No.: US 6,225,309 B1
(45) Date of Patent: *May 1, 2001

(54) AMINOHETEROCYCLIC DERIVATIVES AS ANTITHROMBOTIC OR ANTICOAGULANT AGENTS

(75) Inventors: Alan Wellington Faull; Andrew Stocker; Colette Marie Mayo, all of Macclesfield; John Preston, Knutsford, all of (GB)

(73) Assignee: Zeneca Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/369,857

(22) Filed: Aug. 9, 1999

Related U.S. Application Data

(62) Division of application No. 08/817,031, filed as application No. PCT/GB95/02285 on Sep. 25, 1995, now Pat. No. 5,965,559.

(30) Foreign Application Priority Data

Sep. 26, 1994 (GB) .................................. 9419341
Dec. 21, 1994 (GB) .................................. 9425789
Jun. 1, 1995 (GB) .................................. 9511051

(51) Int. Cl.[7] ................ C07D 401/14; C07D 405/12; C07D 409/14; A61K 31/495; A61P 7/02
(52) U.S. Cl. .............. 514/218; 514/235.8; 514/237.2; 514/252.02; 514/252.03; 514/256; 514/316; 514/318; 514/341; 514/343; 514/353; 540/470; 540/481; 540/575; 540/597; 544/121; 544/129; 544/360; 544/333; 544/364; 546/187; 546/194; 546/268.1; 546/274.1; 546/276.4; 546/279.1
(58) Field of Search .................... 540/470, 481, 540/575, 597; 544/121, 129, 360, 364, 333; 546/187, 194, 268.1, 274.1, 276.4, 279.1; 514/218, 235.8, 237.2, 256, 316, 318, 341, 343, 353

(56) References Cited

U.S. PATENT DOCUMENTS

| | | | |
|---|---|---|---|
| 4,167,567 | 9/1979 | McCall | 424/250 |
| 4,231,938 | 11/1980 | Monaghan et al. | 260/343.5 |
| 4,537,896 | 8/1985 | Claeson et al. | 514/330 |
| 4,564,610 | 1/1986 | Rahtz et al. | 514/80 |
| 4,629,728 | 12/1986 | Regnier et al. | 514/252 |
| 4,788,196 | 11/1988 | Cross et al. | 514/252 |
| 4,806,536 | 2/1989 | Cross et al. | 514/252 |
| 4,835,165 | 5/1989 | Cross et al. | 514/318 |
| 4,840,963 | 6/1989 | Shepard et al. | 514/418 |
| 4,968,704 | 11/1990 | Cross et al. | 514/318 |
| 5,032,604 | 7/1991 | Baldwin et al. | 514/361 |
| 5,138,058 | 8/1992 | Geisen et al. | 544/295 |
| 5,254,563 | 10/1993 | Huth et al. | 514/292 |
| 5,332,822 | 7/1994 | Misra | 546/164 |
| 5,364,865 | 11/1994 | Diana | 514/318 |
| 5,371,091 | 12/1994 | Misra et al. | 514/314 |
| 5,411,971 | 5/1995 | Emonds-Alt et al. | 514/318 |
| 5,556,977 | 9/1996 | Wayne et al. | 544/360 |
| 5,563,141 | 10/1996 | Wayne et al. | 514/252 |
| 5,580,881 | 12/1996 | Binet et al. | 514/307 |
| 5,606,065 | 2/1997 | Emonds-Alt et al. | 546/223 |
| 5,681,954 | 10/1997 | Yamamoto et al. | 544/114 |
| 5,795,893 | 8/1998 | Bondinell et al. | 514/252 |
| 5,856,326 | 5/1999 | Anthony et al. | 514/252 |
| 6,022,869 | * 2/2000 | Faull | 514/227.8 |
| 6,037,343 | 3/2000 | Ali | 514/252 |

FOREIGN PATENT DOCUMENTS

| | | |
|---|---|---|
| 10177/92 | 7/1992 | (AU) . |
| 39 05 364 A1 | 8/1990 | (DE) . |
| 39 43 225 | 6/1991 | (DE) . |
| 42 43 858 A1 | 6/1994 | (DE) . |
| 43 06 506 A1 | 9/1994 | (DE) . |
| 0 097 630 A2 | 1/1984 | (EP) . |

(List continued on next page.)

OTHER PUBLICATIONS

CAPLUS printout of WO 94/22835, 1994.*
Boissier et al., "Synthesis and Pharmacological Study of New Piperazine Derivatives. I. Benzylpiperazines", J. Med. Chem., Sep. 1963, pp. 541–544.
Conway et al., "Approaches to the Generation of 2,3–Indolyne"; Heterocycles, 1992, 34(11) 2095–2108.
Deratani et al., "Synthesis of new dialkylaminopyridine acylation catalysts and their attachment to insoluble polymer supports", Polymer, Apr. 1987, pp. 825–830.
Hibino et al.; "N–Phenylsulfonylinodole derivatives", Chemical Abstracts, 118:147461, Apr. 1993.

(List continued on next page.)

*Primary Examiner*—Mukund J. Shah
*Assistant Examiner*—Thomas McKenzie
(74) *Attorney, Agent, or Firm*—Pillsbury Winthrop LLP

(57) ABSTRACT

The invention concerns $$\begin{array}{c} G^1 = G^2 \\ \diagdown \diagup \\ N \\ \diagup \diagdown \\ (R^1)_m \end{array} \hspace{-6pt} \begin{array}{c} \\ \\ \hspace{-6pt}\text{---} M^1\text{---}A\text{---}CO\text{---}M^2\text{---}M^3\text{---}X\text{---}Q \\ \\ | \\ \text{---}G^3 \end{array} \quad (I)$$

compounds of formula (I), wherein each of $G^1$, $G^2$ and $G^3$ is CH or N; m is 1 or 2; $R^1$ includes hydrogen, halogeno and 1–C)alkyl; $M^1$ is a group of formula: $NR^2$—$L^1$—$T^1R^3$, in which $R^2$ and $R^3$ together form a (1–4C)alylene group, $L^1$ includes (1–4C)alkylene, and $T^1$ is CH or N; A may be a direct link; $M^2$ is a group of the formula: $(T^2R^4)_r L^2$—$T^3R^5$ in which R is 0 or 1, each of $T^2$ and $T^3$ is CH or N, each of $R^4$ and $R^5$ is hydrogen or (1–4C)alkyl, or $R^4$ and $R^5$ together form a (1–4C)alkylene group, and $L^2$ includes (1–4C) alkylene; $M^3$ may be a direct link to X; X includes sulphonyl; and Q includes naphthyl and a heterocyclic moiety; or a pharmaceutically-acceptable salt thereof; processes for their preparation, pharmaceutical compositions containing them and their use as antithrombotic or anticoagulant agents.

25 Claims, No Drawings

FOREIGN PATENT DOCUMENTS

| | | |
|---|---|---|
| 0 232 740 A1 | 8/1987 | (EP) . |
| 0 233 051 | 8/1987 | (EP) . |
| 0 244 115 | 11/1987 | (EP) . |
| 0 308 337 | 3/1989 | (EP) . |
| 0 324 421 A2 | 7/1989 | (EP) . |
| 0 359 389 | 3/1990 | (EP) . |
| 0 352 946 A1 | 10/1990 | (EP) . |
| 0 409 413 | 1/1991 | (EP) . |
| 0 495 750 | 7/1992 | (EP) . |
| 0 515 240 A1 | 11/1992 | (EP) . |
| 0 519 449 A1 | 12/1992 | (EP) . |
| 0 555 824 A1 | 8/1993 | (EP) . |
| 0 576 941 A1 | 1/1994 | (EP) . |
| 0 608 759 A2 | 8/1994 | (EP) . |
| 2 697 252 A1 | 4/1994 | (FR) . |
| 1 449 100 | 9/1976 | (GB) . |
| WO 92/08709 | 5/1992 | (WO) . |
| WO 92/18478 | 10/1992 | (WO) . |
| WO 93/06085 | 4/1993 | (WO) . |
| WO 94/18185 | 8/1994 | (WO) . |
| WO 94/20467 | 9/1994 | (WO) . |
| WO 94/20468 | 9/1994 | (WO) . |
| WO 94/22835 | 10/1994 | (WO) . |
| WO 96/05189 | 2/1996 | (WO) . |
| WO 96/10022 | 4/1996 | (WO) . |
| WO 96/26196 | 8/1996 | (WO) . |
| WO 96/30343 | 10/1996 | (WO) . |
| WO 96/33171 | 10/1996 | (WO) . |
| WO 97/06802 | 2/1997 | (WO) . |
| WO 97/28128 | 8/1997 | (WO) . |
| WO 97/28129 | 8/1997 | (WO) . |
| WO 97/29104 | 8/1997 | (WO) . |
| WO 97/30971 | 8/1997 | (WO) . |
| WO 98/06705 | 2/1998 | (WO) . |
| WO 98/21188 | 5/1998 | (WO) . |

OTHER PUBLICATIONS

Jain et al., "Compounds Acting on the Central Nervous System, VII. Studies in 1–Pyridyl–1–substituted Piperazines. A New Class of Anticonvulsants", J. Med. Chem., Sep. 1967, pp. 812–818.

Kataoka et al., Chemical Abstracts, vol. 123, No. 14, Oct. 2, 1995 Columbus, Ohio, US; abstract No. 179521d, "Homopiperazines as cell migration inhibitors." Xp002081582 see abstract & JP 95 145060 A (TEJIN LTD).

Prasad et al., "Antiamoebic Action of Drugs and Synthetic Compounds Against Trophozoites of Entamoeba Histolytica Under Axenic and Polyxenic Culture Conditions and in the Infected Rat Caecum", Curr. Sci., Aug. 1984, pp. 778–781.

Ratouis et al., "Synthesis and pharmacological Study of New Piperazine Derivatives, II. Phenethylpiperazines", J. Med. Chem., Jan. 1965, pp. 104–107.

Sato et al., "Synthetic Studies on Cardiovascular Agents. III. Synthesis of Pyrano–[2,3–c]pyrazoline Derivatives", Yakugaku Zasshi, vol. 98(3), 1978, pp. 335–348.

Sexena et al., "Quantitative Structure Activity Relationship in 3–4 Disubstituted Pyridines & I–(3"–Amino–4"–pyridyl)–4–arylpiperazines" Indian J. Chem. vol. 19B, Oct. 1980, pp. 873–878.

Sundberg et al. "Synthesis with N–Protected 2–Lithioindoles"; J. Org. Chem., 1973 38(19) 3324–3330.

Von G. Krüger, et al.; (Thomae et al.) Arzneim.–Fosch., Synthesen von N–Benzyl–aminocarbonsäuren und thren Derivaten; (Synthesis and N–benzylaminocarboxylic acids and their derivatives), vol. 23(2a), pp. 290–295.

Yokoyama et al. "Palladium–catalyzed cross–coupling reaction: direct allylation of aryl bromides with allyl acetate" Tetrahedron Letters., vol. 26, No. 52—1985 pp. 6457–6460, XP002081581 Oxford GB * p. 6458–6459: compound 7.

Zagral et al., "Amino acids and peptides. LIX. Synthesis and some biological properties of L–DABB–vasopressin", Collect. Czech. Chem. Commun., vol. 31, 1966, pp. 90–95, XPOO2081879 see compound 11, p. 95.

Mitsunobu et al., "Preparation of Carboxylic Esters and Phosphoric Esters by the Activation of Alcohols", Bull. Chem. Soc. Jpn., 44(10):3427–3430 (1971).

Bowers Nemia et al., "Synthetic Routes to 3–Pyrrolidinol", Synth. Comm., 13(13):1117–1123 (1983).

Cattel et al: "Drug design based on biosynthetic studies: synthesis, biological activity, and kinetics of new inhibitors of 2,3–oxidosualene cyclase and squalene epoxidase.", Steriods., vol. 53, No. 3–5, 1989, pp. 363–391, XP000611661.

Chambers et al., "Preparation of arylpyridine compounds for treating leukotriene–related diseases", Chemical Abstracts, Abstract No. 139113, vol. 119 (1993).

Cross et al., "Preparation of N–[(heterocycliclmethoyx)phenyl] sulfamides and analogs as antiarrhythmics", Chemical Abstracts, Abstract No. 231211, vol. 113 (1989).

E. Jucker, "Über C–substituierte Piperazinderativate", Helv. Chim. Acta., 45:2383–2042 (1962).

Kato et al., "Reactivities of 4–Chloropyridine Derivatives and Their 1–Oxides", Chem. Pharm. Bull., 15:1343–1348 (1967).

Kato et al., "Studies on Ketene and Its Derivatives. LXXVI. [1]) Reactions of Acetoacetamide and β–Aminocrotonamide with β–Diketone, β–Ketoaldehyde and Related Compounds", Chem. Pharm. Bull., 24(2):303–309 (1976).

Kettner et al., "The Selective Inhibition of Thrombin by Peptides of Boroarginine", The Journal of Biological Chemistry, vol. 265, No. 30, pp. 18289–18297 (1990).

Smith et al., "Fibrin, Red Cell and Platelet Interactions in an Experimental Model of Thrombosis", Br. J. Pharmac., vol. 77, pp. 29–38 (1982).

Szmant et al., "Concerning the Variable Character of the Sulfone Group", J. Amer. Chem. Soc., vol. 78, pp. 3400–3403 (1956).

Tabacik et al: "Squalene epoxidase, oxido–squalene cyclase and cholesterol biosynthesis in normal and tumoral mucosa of the human gastrointestinal tract. Evidence of post–HMGCoA regulation.", Biochim. Biophys. Acta, vol. 666, No. 3, 1982, pp. 433–441, XP000610864.

Vigroux e tal., "Cyclization–Activated Prodrugs: N–(Substituted 2–hydroxyphenyl and 2–hydroxypropyl)carbamates Based on Ring–Opened Derivatives of Active Benzoxazolones and Oxazolidones as Mutual Produrgs of Acetamiophen", J. Med. Chem., vol. 38, pp. 3983–3994 (1995).

Vogel et al., "Comparison of Two Experimental Thrombosis Models in Rats Effects of Four Glycosaminoglycans", Thrombosis Research, vol. 54, No. 5, pp. 399–410 (1989).

Sartori et al., "Synthesis and analgesic activities of urea derivatives of α–amino–N–pyridyl benzene propanamide", Eur J. Med Chem (1994), 431–439.

Wallis, "Inhibitors of Coagulation Factor Xa: From Macromolecular Beginnings to Small Molecules", Current Opinion in Therapeutic Patents, Aug., 1993, pp. 1173–1179.

Budavari: Merck Index, vol. 11 Ed., 1989, See Monograph Nos. 804 and 2807.

* cited by examiner

AMINOHETEROCYCLIC DERIVATIVES AS ANTITHROMBOTIC OR ANTICOAGULANT AGENTS

This application is a divisional of application Ser. No. 08/817,031 filed Mar. 26, 1997, now U.S. Pat. No. 5,965,559 which is a 371 of PCT/GB95/02285 filed Sep. 25, 1995.

The invention relates to a group of aminoheterocyclic derivatives, or pharmaceutically-acceptable salts thereof, which possess antithrombotic and anticoagulant properties and are accordingly useful in methods of treatment of the human or animal body. The invention also relates to processes for the preparation of said aminoheterocyclic derivatives, to pharmaceutical compositions containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by R. B. Wallis, *Current Opinion in Therapeutic Patents*, 1993, 1173–1179. Thus it is known that two proteins, one known as antistatin and the other known as tick anticoagulant protein (TAP), are specific Factor Xa inhibitors which possess antithrombotic properties in various animal models of thrombotic disease.

It is also known that certain non-peptidic compounds possess Factor Xa inhibitory properties. Of the low molecular weight inhibitors mentioned in the review by R. B. Wallis, all possessed a strongly basic group such as an amidinophenyl or amidinonaphthyl group.

It is the object of the present invention to provide a new class of agent which lacks the amidino group previously believed to be an essential feature for a Factor Xa inhibitor.

We have now found that certain amino-substituted heterocyclic derivatives possess Factor Xa inhibitory activity. Many of the compounds of the present invention also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

The compounds of the present invention possess activity in the treatment or prevention of a variety of medical disorders where anticoagulant therapy is indicated, for example in the treatment or prevention of thrombotic conditions such as coronary artery and cerebro-vascular disease. Further examples of such medical disorders include various cardiovascular and cerebrovascular conditions such as myocardial infarction, the formation of atherosclerotic plaques, venous or arterial thrombosis, coagulation syndromes, vascular injury including reocclusion and restenosis following angioplasty and coronary artery bypass surgery, thrombus formation after the application of blood vessel operative techniques, the introduction of artificial heart valves or on the recirculation of blood, cerebral infarction, cerebral thrombosis, stroke, cerebral embolism, pulmonary embolism, ischaemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

According to one aspect of the invention there is provided an aminoheterocyclic derivative of the formula I (set out hereinafter)

wherein $G^1$ is CH or N;
$G^2$ is CH or N;
$G^3$ is CH or N;
m is 1 or 2;
$R^1$ is hydrogen, amino, halogeno, cyano, (1–4C)alkyl or (1–4C)alkoxy;
$M^1$ is a group of the formula $$NR^2—L^1—T^1R^3$$

in which $R^2$ and $R^3$ together form a (1–4C)alkylene group,
$L^1$ is (1–4C)alkylene, and
$T^1$ is CH or N,
and wherein 1 or 2 methylene groups within $L^1$ and the ring formed when $R^2$ and $R^3$ are linked optionally bears a (1–4C)alkyl substituent;
A is a direct link to the carbonyl group, or A is (1–4C)alkylene;
$M^2$ is a group of the formula $$(T^2R^4)_r—L^2—T^3R^5$$

in which r is 0 or 1,
$T^2$ is CH or N,
$T^3$ is CH or N,
$R^4$ is hydrogen or (1–4C)alkyl, $R^5$ is hydrogen or (1–4C)alkyl, or $R^4$ and $R^5$ together form a (1–4C)alkylene, methylenecarbonyl or carbonylmethylene group, or $R^4$ is a (2–3C)alkylene group which is linked to a methylene group within $L^2$ forming a 5- or 6-membered ring involving $R^4$ and $T^2$, or
$R^5$ is a (2–3C)alkylene group which is linked to a methylene group within $L^2$ forming a 5- or 6-membered ring involving $R^5$ and $T^3$,
$L^2$ is (1–4C)alkylene, (3–6C)cycloalkane-1,2-diyl, (1–3C)alkylene-carbonyl or phenylene, and, when r is 1, $L^2$ may also be carbonyl-(1–3C)alkylene,
and wherein 1 or 2 methylene groups within $L^2$ and the rings formed when $R^4$ and $R^5$, $R^4$ and $L^2$ or $R^5$ and $L^2$ are linked optionally bears a substituent selected from the group consisting of oxo, carboxy, (1–4C)alkoxycarbonyl, carbamoyl, N-(1–4C)alkylcarbamoyl, N,N-di-(1–4C)alkylcarbamoyl, pyrrolidin-1-ylcarbonyl, piperidinocarbonyl, morpholinocarbonyl, piperazin-1-ylcarbonyl, 4-(1–4C)alkylpiperazin-1-ylcarbonyl, N-phenylcarbamoyl, N-(1–4C)alkyl-N-phenylcarbamoyl, N-[phenyl-(1–3C)alkyl]carbamoyl, N-(1–4C)alkyl-N-[phenyl-(1–3C)alkyl]carbamoyl, N-[hydroxy-(2–3C)alkyl]carbamoyl, N-(1–4C)alkyl-N-[hydroxy-(2–3C)alkyl]carbamoyl, N-[(1–4C)alkoxy-(2–3C)alkyl]carbamoyl, N-(1–4C)alkyl-N-[(1–4C)alkoxy-(2–3C)alkyl]carbamoyl, N-[carboxy-(1–3C)alkyl]carbamoyl, N-(1–4C)alkyl-N-[carboxy-(1–3C)alkyl]carbamoyl, N-[carboxy-(1–3C)alkyl]-N-[hydroxy-(2–3C)alkyl]carbamoyl, N-[carboxy-(1–3C)

alkyl]-N-[(1–4C)alkoxy-(2–3C)alkyl]carbamoyl, N-[(1–4C)alkoxycarbonyl-(1–3C)alkyl]carbamoyl, N-(1–4C)alkyl-N-[(1–4C)alkoxycarbonyl-(1–3C) alkyl]carbamoyl, N-[(1–4C)alkoxycarbonyl-(1–3C) alkyl]-N-[hydroxy-(2–3C)alkyl]carbamoyl, N-[(1–4C) alkoxycarbonyl-(1–3C)alkyl]-N-[(1–4C)alkoxy-(2–3C)alkyl]carbamoyl, (1–4C)alkyl, carboxy-(1–4C) alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, pyrrolidin-1-ylcarbonyl-(1–4C)alkyl, piperidinocarbonyl-(1–4C)alkyl, morpholinocarbonyl-(1–4C)alkyl, piperazin-1-ylcarbonyl-(1–4C)alkyl, 4-(1–4C)alkylpiperazin-1-ylcarbonyl-(1–4C)alkyl, N-phenylcarbamoyl-(1–4C)alkyl, N-[phenyl-(1–3C) alkyl]carbamoyl-(1–4C)alkyl, hydroxy-(1–4C)alkyl, (1–4C)alkoxy-(1–4C)alkyl and phenyl-(1–4C)alkyl, and wherein any heterocyclic group in said substituent optionally bears 1 or 2 substituents selected from the group consisting of (1–4C)alkyl, (1–4C)alkoxy, carboxy, (1–4C)alkoxycarbonyl, carbamoyl, N-(1–4C) alkylcarbamoyl and N,N-di-(1–4C)alkylcarbamoyl, and wherein any phenyl or phenylene group in $M^2$ optionally bears 1 or 2 substituents selected from the group consisting of halogeno, trifluoromethyl, (1–4C)alkyl and (1–4C)alkoxy;

$M^3$ is a direct link to X, or $M^3$ is a group of the formula $$L^3-(NR^6)_s$$

in which s is 0 or 1, $R^6$ is hydrogen or (1–4C)alkyl, or $R^5$ and $R^6$ together form a (1–4C)alkylene, methylenecarbonyl or carbonylmethylene group, or R6 is a (2–3C)alkylene group which is linked to a methylene group within $L^3$ forming a 5- or 6-membered ring involving $NR^6$, $L^3$ is (1–4C)alkylene, (3–6C)cycloalkane-1,2-diyl, carbonyl-(1—3C)alkylene or phenylene, and, when s is 1, $L^3$ may also be (1–3C)alkylene-carbonyl, and wherein 1 or 2 methylene groups within $L^3$ and the rings formed when $R^5$ and $R^6$ or $R^6$ and $L^3$ are linked optionally bears a substituent selected from the group consisting of oxo, carboxy, (1–4C)alkoxycarbonyl, carbamoyl, N-(1–4C)alkylcarbamoyl, N,N-di-(1–4C) alkylcarbamoyl, pyrrolidin-1-ylcarbonyl, piperidinocarbonyl, morpholinocarbonyl, piperazin-1-ylcarbonyl, 4-(1–4C)alkylpiperazin-1-ylcarbonyl, N-pbenylcarbamoyl, N-(1–4C)alkyl-N-phenylcarbamoyl, N-[phenyl-(1–3C)alkyl]carbamoyl, N-(1–4C)alkyl-N-[pbenyl-(1–3C)alkyl]carbamoyl, (1–4C)alkyl, carboxy-(1–4C)alkyl, (1–4C) alkoxycarbonyl-(1–4C)alkyl, carbamoyl-(1–4C)alkyl, N-(1–4C)alkylcarbamoyl-(1–4C)alkyl, N,N-di-(1–4C) alkylcarbamoyl-(1–4C)alkyl, pyrrolidin-1-ylcarbonyl-(1–4C)alkyl, piperidinocarbonyl-(1–4C)alkyl, morpholinocarbonyl-(1–4C)alkyl, piperazin-1-ylcarbonyl-(1–4C)alkyl, 4-(1–4C)alkylpiperazin-1-ylcarbonyl-(1–4C)alkyl, N-phenylcarbamoyl-(1–4C) alkyl, N-[phenyl-(1–3C)alkyl]carbamoyl-(1–4C)alkyl, hydroxy-(1–4C)alkyl, (1–4C)alkoxy-(1–4C)alkyl and phenyl-(1–4C)alkyl, and wherein any heterocyclic group in said substituent optionally bears 1 or 2 substituents selected from the group consisting of (1–4C)alkyl, (1–4C)alkoxy, carboxy, (1–4C)alkoxycarbonyl, carbamoyl, N-(1–4C) alkylcarbamoyl and N,N-di-(1–4C)alkylcarbamoyl, and wherein any phenyl or phenylene group in $M^3$ optionally bears 1 or 2 substituents selected from the group consisting of halogeno, trifluoromethyl, (1–4C)alkyl and (1–4C)alkoxy;

X is oxy, thio, sulphinyl, sulphonyl, carbonyl, carbonyloxy, carbonylamino, N-(1–4C) alkylcarbonylamino, sulphonylamino, methylene, (1–4C)alkylmethylene or di-(1–4C)alkylmethylene, or, when $T^3$ is CH and $M^3$ is a direct link to X, X may also be aminosulphonyl or oxycarbonyl; and Q is phenyl, naphthyl, phenyl-(1–4C)alkyl, phenyl-(2–4C)alkenyl, phenyl-(2–4C)alkynyl, (5–7C) cycloalkyl or a heterocyclic moiety containing up to 4 heteroatoms selected from the group consisting of nitrogen, oxygen and sulphur, and Q optionally bears 1, 2 or 3 substituents selected from the group consisting of hydroxy, amino, halogeno, cyano, trifluoromethyl, nitro, carboxy, carbamoyl, formyl, formimidoyl, formohydroximoyl, (1–4C)alkoxycarbonyl, (1–4C) alkyl, (1–4C)alkoxy, N-(1–4C)alkylcarbamoyl, N,N-di-(1–4C)alkylcarbamoyl, (1–4C)alkylamino, di-(1–4C)alkylamino, (2–4C)alkanoylamino, (2–4C) alkanoyl, (2–4C)alkanoimidoyl, (2–4C) alkanohydroximoyl, phenyl, heteroaryl, phenoxy, phenylthio, phenylsulphinyl, phenylsulphonyl, heteroaryloxy, heteroarylthio, heteroarylsulphinyl, heteroarylsulphonyl, benzyl and benzoyl, and wherein said heteroaryl substituent or the heteroaryl group in a heteroaryl-containing substituent comprises a 5- or 6-membered monocyclic heteroaryl ring containing up to 3 heteroatoms selected from the group consisting of nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1, 2, 3 or 4 substituents selected from the group consisting of halogeno, trifluoromethyl, cyano, trifluoromethoxy, nitro, (1–4C)alkyl, (1–4C) alkoxy, hydroxy, amino, carboxy, carbamoyl, (1–4C) alkoxycarbonyl, N-(1–4C)alkylcarbamoyl, N,N-di-(1–4C)alkylcarbamoyl, (1–4C)alkylamino, di-(1–4C) alkylamino, (2–4C)alkanoylamino and tetrazolyl;

or a pharmaceutically-acceptable salt thereof.

The chemical formulae referred to herein by Roman numerals are set out for convenience on a separate sheet hereinafter. In this specification the term "alkyl" includes both straight and branched chain alkyl groups but references to individual alkyl groups such as "propyl" are specific for the straight chain version only. An analogous convention applies to other generic terms.

It is to be understood that certain aminoheterocyclic derivatives of the present invention can exist in solvate as well as unsolvated forms such as, for example, hydrated forms. It is to be understood that the invention encompasses all such solvated forms which possess Factor Xa inhibitory activity.

It is further to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or by resolution of a racemic form.

According to a further aspect of the invention there is provided an aminoheterocyclic derivative of the formula Ia
  wherein $G^1$ is CH or N;
  $G^2$ is CH or N;
  m is 1 or 2;
  $R^1$ is hydrogen, amino, halogeno, cyano, (1–4C)alkyl or (1–4C)alkoxy;
  $M^1$ is a group of the formula $NR^2—L^1—T^1R^3$ in which $R^2$ and $R^3$ together form a (1–4C)alkylene group,
  $L^1$ is (1–4C)alkylene, and
  $T^1$ is CH or N,
  and wherein 1 or 2 methylene groups within $L^1$ and the rings formed when $R^2$ and $R^3$ are linked optionally bears a (1–4C)alkyl substituent;
  (1–4C)alkyl and (1–4C)alkoxy;
  A is a direct link to the carbonyl group, or A is (1–4C)alkylene;
  $M^2$ is a group of the formula $(T^2R^4)_r—L^2—T^3R^5$ in which r is 0 or 1,
  $T^2$ is CH or N,
  $T^3$ is CH or N,
  $R^4$ is hydrogen or (1–4C)alkyl, $R^5$ is hydrogen or (1–4C)alkyl, or $R^4$ and
  $R^5$ together form a (1–4C)alkylene, methylenecarbonyl or carbonylmethylene group, or $R^4$ is a (2–3C)alkylene group which is linked to a methylene group within $L^2$ forming a 5- or 6-membered ring involving $R^4$ and $T^2$, or $R^5$ is a (2–3C)alkylene group which is linked to a methylene group within $L^2$ forming a 5- or 6-membered ring involving $R^5$ and $T^3$,
  $L^2$ is (1–4C)alkylene, (3–6C)cycloalkane-1,2-diyl, (1–3C)alkylene-carbonyl or phenylene, and, when r is 1, $L^2$ may also be carbonyl-(1–3C)alkylene,
  and wherein 1 or 2 methylene groups within $L^2$ and the rings formed when $R^4$ and $R^5$, $R^4$ and $L^2$ or $R^5$ and $L^2$ are linked optionally bears a substituent selected from the group consisting of carboxy, (1–4C)alkoxycarbonyl, carbamoyl, N-(1–4C)alkylcarbamoyl, N,N-di-(1–4C)alkylcarbamoyl, pyrrolidin-1-ylcarbonyl, piperidinocarbonyl, morpholinocarbonyl, piperazin-1-ylcarbonyl, 4-(1–4C)alkylpiperazin-1-ylcarbonyl, N-phenylcarbamoyl, N-(1–4C)alkyl-N-phenylcarbamoyl, N-[phenyl-(1–3C)alkyl]carbamoyl, N-(1–4C)alkyl-N-[phenyl-(1–3C)alkyl]carbamoyl, N-[hydroxy-(2–3C)alkyl]carbamoyl, N-(1–4C)alkyl-N-[hydroxy-(2–3C)alkyl]carbamoyl, N-[(1–4C)alkoxy-(2–3C)alkyl]carbamoyl, N-(1–4C)alkyl-N-[(1–4C)alkoxy-(2–3C)alkyl]carbamoyl, N-[carboxy-(1–3C)alkyl]carbamoyl, N-(1–4C)alkyl-N-[carboxy-(1–3C)alkyl]carbamoyl, N-[carboxy-(1–3C)alkyl]-N-[hydroxy-(2–3C)alkyl]carbamoyl, N-[carboxy-(1–3C)alkyl]-N-[(1–4C)alkoxy-(2–3C)alkyl]carbamoyl, N-[(1–4C)alkoxycarbonyl-(1–3C)alkyl]carbamoyl, N-(1–4C)alkyl-N-[(1–4C)alkoxycarbonyl-(1–3C)alkyl]carbamoyl, N-[(1–4C)alkoxycarbonyl-(1–3Chalkyl]-N-[hydroxy-(2–3C)alkyl]carbamoyl, N-[(1–4C)alkoxycarbonyl-(1–3C)alkyl]-N-[(1–4C) alkoxy-(2–3C)alkyl]carbamoyl, (1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, pyrrolidin-1-ylcarbonyl-(1–4C)alkyl, piperidinocarbonyl-(1–4C)alkyl, morpholinocarbonyl-(1–4C)alkyl, piperazin-1-ylcarbonyl-(1–4C)alkyl, 4-(1–4C)alkylpiperazin-1-ylcarbonyl-(1–4C)alkyl, N-phenylcarbamoyl-(1–4C)alkyl, N-[phenyl-(1–3C)alkyl]carbamoyl-(1–4C)alkyl, hydroxy-(1–4C)alkyl, (1–4C)alkoxy-(1–4C)alkyl and phenyl-(1–4C)alkyl,
  and wherein any heterocyclic group in said substituent optionally bears 1 or 2 substituents selected from the group consisting of (1–4C)alkyl, (1–4C)alkoxy, carboxy, (1–4C)alkoxycarbonyl, carbamoyl, N-(1–4C)alkylcarbamoyl and N,N-di-(1–4C)alkylcarbamoyl,
  and wherein any phenyl or phenylene group in $M^2$ optionally bears 1 or 2 substituents selected from the group consisting of halogeno, trifluoromethyl, (1–4C)alkyl and (1–4C)alkoxy;
  $M^3$ is a direct link to X, or $M^3$ is a group of the formula $L^3—(NR^6)_s$ in which s is 0 or 1,
  $R^6$ is hydrogen or (1–4C)alkyl, or $R^5$ and $R^6$ together form a (1–4C)alkylene, methylenecarbonyl or carbonylmethylene group, or $R^6$ is a $(^{2-3}C)$alkylene group which is linked to a methylene group within $L^3$ forming a 5- or 6-membered ring involving $NR^6$,
  $L^3$ is (1–4C)alkylene, (3–6C)cycloalkane-1,2-diyl, carbonyl-(1–3C)alkylene or phenylene, and, when s is 1, $L^3$ may also be (1–3C)alkylene-carbonyl,
  and wherein 1 or 2 methylene groups within $L^3$ and the rings formed when $R^5$ and $R^6$ or $R^6$ and $L^3$ are linked optionally bears a substituent selected from the group consisting of carboxy, (1–4C)alkoxycarbonyl, carbamoyl, N-(1–4C)alkylcarbamoyl, N,N-di-(1–4C)alkylcarbamoyl, pyrrolidin-1-ylcarbonyl, piperidinocarbonyl, morpholinocarbonyl, piperazin-1-ylcarbonyl, 4-(1–4C)alkylpiperazin-1-ylcarbonyl, N-phenylcarbamoyl, N-(1–4C)alkyl-N-phenylcarbamoyl, N-[phenyl-(1–3C[]alkyl] carbamoyl, N-(1–4C)alkyl-N-[phenyl-(1–3C)alkyl]-carbamoyl, (1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, pyrrolidin-1-ylcarbonyl-(1–4C)alkyl, piperidinocarbonyl-(1–4C)alkyl, morpholinocarbonyl-(1–4C)alkyl, piperazin-1-ylcarbonyl-(1–4C)alkyl, 4-(1–4C)alkylpiperazin-1-ylcarbonyl-(1–4C)alkyl, N-phenylcarbamoyl-(1–4C) alkyl, N-[phenyl-(1–3C)alkyl]carbamoyl-(1–4C)alkyl, hydroxy-(1–4C)alkyl, (1–4C)alkoxy-(1–4C)alkyl and phenyl-(1–4C)alkyl,
  and wherein any heterocyclic group in said substituent optionally bears 1 or 2 substituents selected from the group consisting of (1–4C)alkyl, (1–4C)alkoxy, carboxy, (1–4C)alkoxycarbonyl, carbamoyl, N-(1–4C)alkylcarbamoyl and N,N-di-(1–4C)alkylcarbamoyl,
  and wherein any phenyl or phenylene group in $N^3$ optionally bears 1 or 2 substituents selected from the group consisting of halogeno, trifluoromethyl, (1–4C)alkyl and (1–4C)alkoxy;
  X is oxy, thio, sulphinyl, sulphonyl, carbonyl, carbonyloxy, carbonylamino, N-(1–4C)

alkylcarbonylamino, sulphonylamino, methylene, (1–4C)alkylmethylene or di-(1–4C)alkylmethylene, or, when T³ is CH and M³ is a direct link to X, X may also be aminosulphonyl or oxycarbonyl; and Q is phenyl, naphthyl, phenyl-(1–4C)alkyl, phenyl-(2–4C)alkenyl, phenyl-(2–4C)alkynyl, (5–7C)cycloalkyl or a heterocyclic moiety containing up to 4 heteroatoms selected from the group consisting of nitrogen, oxygen and sulphur, and Q optionally bears 1, 2 or 3 substituents selected from the group consisting of hydroxy, amino, halogeno, cyano, trifluoromethyl, nitro, carboxy, carbamoyl, formyl, formimidoyl, formohydroximoyl, (1–4C)alkoxycarbonyl, (1–4C)alkyl, (1–4C)alkoxy, N-(1–4C)alkylcarbamoyl, N,N-di-(1–4C)alkylcarbamoyl, (1–4C)alkylamino, di-(1–4C)alkylamino, (2–4C)alkanoylamino, (2–4C)alkanoyl, (2–4C)alkanoimidoyl, (2–4C)alkanohydroximoyl, phenyl, heteroaryl, phenoxy, phenylthio, phenylsulphinyl, phenylsulphonyl, heteroaryloxy, heteroarylthio, heteroarylsulphinyl, heteroarylsulphonyl, benzyl and benzoyl, and wherein said heteroaryl substituent or the heteroaryl group in a heteroaryl-containing substituent comprises a 5- or 6-membered monocyclic heteroaryl ring containing up to 3 heteroatoms selected from the group consisting of nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1 or 2 substituents selected from the group consisting of halogeno, trifluoromethyl, (1–4C)alkyl, (1–4C)alkoxy, hydroxy, amino, carboxy, carbamoyl, (1–4C)alkoxycarbonyl, N-(1–4C)alkylcarbamoyl, N,N-di-(1–4C)alkylcarbamoyl, (1–4C)alkylamino, di-(1–4C)alkylamino, (2–4C)alkanoylamino and tetrazolyl;

or a pharmaceutically-acceptable salt thereof.

Suitable values for the generic terms referred to above include those set out below.

When m is 2, each R¹ is independently selected from hydrogen, amino, halogeno, cyano, (1–4C)alkyl and (1–4C)alkoxy.

A suitable value for R¹ when it is a halogeno group, for a halogeno substituent in M² or M³ or for a halogeno substituent in Q is, for example, fluoro, chloro, bromo or iodo.

A suitable value for R¹ when it is a (1–4C)alkyl group, for a (1–4C)alkyl substituent in M¹, M² or M³ or for a (1–4C)alkyl substituent in Q is, for example, methyl, ethyl, propyl, isopropyl, butyl, isobutyl, sec-butyl or tert-butyl.

A suitable value for R¹ when it is a (1–4C)alkoxy group, for a (1–4C)alkoxy substituent in M² or M³ or for a (1–4C)alkoxy substituent in Q is, for example, methoxy, ethoxy, propoxy, isopropoxy or butoxy.

A suitable value for R⁴, R⁵ or R⁶ when it is (1–4C)alkyl is, for example, methyl, ethyl, propyl, isopropyl, butyl or sec-butyl.

A suitable value for a (1–4C)alkylene group formed by R² and R³ together, by R⁴ and R⁵ together or by R⁵ and R⁶ together is, for example, methylene, ethylene, trimethylene or tetramethylene.

A suitable value for a (2–3C)alkylene group by which R⁴ may be linked to a methylene group within L², R⁵ may be linked to a methylene group within L² or R⁶ may be linked to a methylene group within L³ is, for example, ethylene or trimethylene.

A suitable value for L¹, L² or L³ when it is (1–4C)alkylene is, for example, methylene, ethylene, trimethylene or tetramethylene; a suitable value for L² or L³ when it is (3–6C)cycloalkane-1,2-diyl is, for example, cyclopropane-1,2-diyl, cyclobutane-1,2-diyl, cyclopentane-1,2-diyl or cyclohexane-1,2-diyl; when it is (1–3C)alkylene-carbonyl is, for example methylenecarbonyl, ethylenecarbonyl or trimethylenecarbonyl; and when it is phenylene is, for example, 1,3- or 1,4-phenylene.

A suitable value for L² and L³ when it is carbonyl-(1–3C)alkylene is, for example, carbonylmethylene, carbonylethylene or carbonyltrimethylene.

Suitable values for the substituents which may be present within M¹, M² or M³ include, for example:

| | |
|---|---|
| for (1-4C)alkoxycarbonyl: | methoxycarbonyl, ethoxycarbonyl, propoxycarbonyl and tert-butoxycarbonyl; |
| for N-(1-4C)alkylcarbamoyl: | N-methylcarbamoyl, N-ethylcarbamoyl and N-propylcarbamoyl; |
| for N,N-di-[(1-4C)alkyl]-carbamoyl: | N,N-dimethylcarbamoyl, N-ethyl-N-methylcarbamoyl and N,N-diethylcarbamoyl; |
| for 4-(1-4C)alkylpiperazin-1-ylcarbonyl: | 4-methylpiperazin-1-ylcarbonyl and 4-ethylpiperazin-1-ylcarbonyl; |
| for N-(1-4C)alkyl-N-phenylcarbamoyl: | N-methyl-N-phenylcarbamoyl and N-ethyl-N-phenylcarbamoyl; |
| for N-[phenyl-(1-3C)alkyl]-carbamoyl: | N-benzylcarbamoyl and N-phenethylcarbamoyl; |
| for N-(1-4C)alkyl-N-[phenyl-(1-3C)alkyl]carbamoyl: | N-benzyl-N-methylcarbamoyl and N-methyl-N-phenethylcarbamoyl; |
| for N-[hydroxy-(2-3C)alkyl]-carbamoyl: | N-(2-hydroxyethyl)carbamoyl and N-(3-hydroxypropyl)carbamoyl; |
| for N-(1-4C)alkyl-N-[hydroxy-(2-3C)alkyl]carbamoyl: | N-(2-hydroxyethyl)-N-methylcarbamoyl and N-(2-hydroxyethyl)-N-ethyl-carbamoyl; |
| for N-[(1-4C)alkoxy-(2-3c)alkyl]-carbamoyl: | N-(2-methoxyethyl)carbamoyl and N-(2-ethoxyethyl)carbamoyl; |
| for N-(1-4C)alkyl-N-[(1-4C)-alkoxy-(2-3C)alkyl]carbamoyl: | N-(2-methoxyethyl)-N-methylcarbamoyl and N-(2-ethoxyethyl)-N-ethyl-carbamoyl; |
| for N-[carboxy-(1-3C)alkyl]-carbamoyl: | N-(carboxymethyl)carbamoyl, N-(1-carboxyethyl)carbamoyl and N-(2-carboxyethyl)carbamoyl; |
| for N-(1-4C)alkyl-N-[carboxy-(1-3C)alkyl]carbamoyl: | N-(carboxymethyl)-N-methylcarbamoyl, N-(1-carboxyethyl)-N-methylcarbamoyl and N-(2-carboxyethyl)-N-methylcarbamoyl; |
| for N-[carboxy-(1-3C)alkyl]-N-[hydroxy-(2-3C)alkyl]carbamoyl: | N-(carboxymethyl)-N-(2-hydroxyethyl)-carbamoyl; |
| for N-[carboxy-(1-3C)alkyl]-N-[(1-4C)alkoxy-(2-3C)alkyl]-carbamoyl: | N-(carboxymethyl)-N-(2-methoxyethyl)-carbamoyl; |
| for N-[(1-4C)alkoxycarbonyl-(1-3C)alkyl]carbamoyl: | N-(methoxycarbonylmethyl)carbamoyl, N-(ethoxycarbonylmethyl)carbamoyl, N-(1-methoxycarbonylethyl)carbamoyl and N-(2-methoxycarbonylethyl)carbamoyl; |
| for N-(1-4C)alkyl-N-[(1-4C)alkoxycarbonyl-(1-3C)alkyl]carbamoyl: | N-(methoxycarbonylmethyl)-N-methylcarbamoyl; |
| for N-[(1-4C)alkoxycarbonyl-(1-3C)alkyl]-N-[hydroxy-(2-3C)alkyl]carbamoyl: | N-(2-hydroxyethyl)-N-(methoxycarbonylmethyl)carbamoyl; |
| for N-(1-4C)alkoxycarbonyl-(1-3C)alkyl]-N-[(1-4C)alkoxy-(2-3C)alkyl]carbamoyl: | N-(methoxycarbonylmethyl)-N-(2-methoxyethyl)carbamoyl; |
| for (1-4C)alkyl: | methyl, ethyl, propyl, isopropyl and butyl; |

-continued

| | |
|---|---|
| for carboxy-(1-4C)alkyl: | carboxymethyl, 1-carboxyethyl, 2-carboxyethyl and 3-carboxypropyl; |
| for (1-4C)alkoxycarbonyl-(1-4C)alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |
| for carbamoyl-(1-4C)alkyl: | carbamoylmethyl, 1-carbamoylethyl, 2-carbamoylethyl and 3-carbamoylpropyl; |
| for N-(1-4C)alkylcarbamoyl-(1-4C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di-[(1-4C)alkyl]-carbamoyl-(1-4C)alkyl: | N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; |
| for pyrrolidin-1-yl-carbonyl-(1-4C)alkyl: | pyrrolidin-1-ylcarbonylmethyl, 1-(pyrrolidin-1-ylcarbonyl)ethyl and 2-(pyrrolidin-1-ylcarbonyl) ethyl; |
| for piperidinocarbonyl-(1-4C)alkyl: | piperidinocarbonylmethyl, 1-(piperidinocarbonyl)ethyl and 2-(piperidinocarbonyl)ethyl; |
| for morpholinocarbonyl(1-4C)alkyl: | morpholinocarbomylmethyl, 1-(morpholinocarbonyl)ethyl and 2-(morpholinocarbonyl)ethyl; |
| for piperazin-1-yl-carbonyl-(1-4C)alkyl: | piperazin-1-ylcarbonylmethyl, 1-(piperazin-1-ylcarbonyl)ethyl and 2-(piperazin-1-ylcarbonyl)ethyl; |
| for 4-(1-4C)alkylpiperazin-1-ylcarbonyl-(1-4C)alkyl: | 4-methylpiperazin-1-ylcarbonylmethyl, 4-ethylpiperazin-1-ylcarbonylmethyl, 2-(4-methylpiperazin-1-ylcarbonyl)-ethyl and 2-(4-ethylpiperazin-1-yicarbonyl)ethyl; |
| for N-phenylcarbamoyl-(1-4C)alkyl: | N-phenylcarbamoylmethyl and 2-(N-phenylcarbamoyl)ethyl; |
| for N-[phenyl-(1-3C)alkyl]-carbamoyl-(1-4C)alkyl: | N-benzylcarbamoylmethyl, N-phenethylcarbamoylmethyl and 2-(N-benzylcarbamoyl)ethyl; |
| for hydroxy-(1-4C)alkyl: | hydroxymethyl, 1-hydroxyethyl, 2-hydroxyethyl and 3-hydroxypropyl; |
| for (1-4C)alkoxy-(1-4C)alkyl: | methoxymethyl, ethoxymethyl, 1-methoxymethyl, 2-methoxyethyl, 2-ethoxyethyl and 3-methoxypropyl; and |
| for phenyl-(1-4C)alkyl: | benzyl, phenethyl and 3-phenylpropyl. |

Suitable values for substituents which may be present on a heterocyclic group within a substituent which may be present within $M^2$ or $M^3$ include, for example:-

| | |
|---|---|
| for (1-4C)alkyl: | methyl, ethyl, propyl and isopropyl; |
| for (1-4C)alkoxy: | methoxy, ethoxy and propoxy; |
| for (1-4C)alkoxycarbonyl: | methoxycarbonyl, ethoxycarbonyl, propoxycarbonyl and tert-butoxycarbonyl; |
| for N-(1-4C)alkylcarbamoyl: | N-methylcarbamoyl and N-ethylcarbamoyl; and |
| for N,N-di-(1-4C)alkyl-carbamoyl: | N,N-dimethylcarbamoyl, N-ethyl-N-methylcarbamoyl and N,N-diethylcarbamoyl. |

A suitable value for A when it is (1–4C)alkylene is, for example, methylene, ethylene, trimethylene and tetramethylene.

It is to be understood that when $M^1$ is a group of the formula

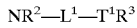

$$NR^2—L^1—T^1R^3$$

the order of the presentation of this group is significant as to the orientation of attachment of the group. Thus it is the $NR^2$ group which is attached to the heterocyclic group, for example, when $G^1$ and $G^2$ are each CH, the pyridyl group which bears the substituent $R^1$. It is also to be understood that within the $NR^2$ group it is the N atom which is attached to $L^1$. Likewise the $R^2$ group is attached to the N atom and not to the $L^1$ group. Similarly in the $T^1R^3$ group it is the $T^1$ group which is attached to the group A of formula I (or the CO group within formula I when A is a direct link) and the $R^3$ group is attached to the $T^1$ group and not to the group A of formula I. A similar convention applies to the attachment of the groups $M^2$ and $M^3$ and to the attachment of the $T^2$, $T^3$ and $NR^6$ groups within $M^2$ or $M^3$.

It is further to be understood that when $R^4$ is a (2–3C) alkylene group such as ethylene and trimethylene which is linked to a methylene group which $L^2$ forming a 5- or 6-membered ring involving $T^2$ and $R^4$, a suitable ring so formed when $T^2$ is N is, for example, pyrrolidine-1,3-diyl, piperidine-1,3-diyl and piperidine-1,4-diyl and a suitable ring so formed when $T^2$ is CH is, for example, cyclopentane-1,3-diyl, cyclohexane-1,3-diyl and cyclohexane-1,4-diyl. Such ring systems are also suitable when, for example, $R^5$ is linked to a methylene group within $L^2$. Ring systems such as pyrrolidine-1,3-diyl, piperidine-1,3-diyl and piperidine-1,4-diyl are also suitable when $R^6$ is linked to a methylene within $L^3$.

For the avoidance of doubt it is stated that a suitable heterocyclic group in a substituent which may be present within $M^2$ and $M^3$ includes, for example, pyrrolidin-1-yl, piperidino, morpholino, piperazin-1-yl and 4-(1–4C) alkylpiperazin-1-yl whether directly attached or attached by way of a linking group as in, for example, pyrrolidin-1-ylcarbonyl-(1–4C)alkyl such as 2-(pyrrolidin-1-ylcarbonyl) ethyl.

A suitable value for X when it is a N-(1–4C)alkylcarbonylamino group is, for example, N-methylcarbonylamino or N-ethylcarbonylamino; when it is (1–4C)alkylmethylene is, for example, ethane-1,1-diyl or propane-1,1-diyl; and when it is di-(1–4C)alkylmethylene is, for example, propane-2,2-diyl. It is also to be understood that when X is a carbonyloxy, carbonylamino or N-(1–4C) alkylcarbonylamino group, it is the carbonyl group therein which is attached to H3. Likewise when X is a sulphonylamino group it is the sulphonyl group therein which is attached to $M^3$ whereas, when X is an aminosulphonyl group, the sulphonyl group therein is attached to Q.

A suitable value for Q when it is naphthyl is, for example, 1-naphthyl or 2-naphthyl; when it is phenyl-(1–4C)alkyl is, for example, benzyl, phenethyl and 3-phenylpropyl, when it is phenyl-(2–4C)alkenyl is, for example, styryl, cinnamyl or 3-phenylprop-2-enyl; when it is phenyl-(2–4C)alkynyl is, for example, 2-phenylethynyl, 3-phenylprop-2-ynyl and 3-phenylprop-1-ynyl; and when it is (5–7C)cycloalkyl is, for example, cyclopentyl, cyclohexyl and cycloheptyl.

A suitable value for Q when it is a heterocyclic moiety containing up to 4 heteroatoms selected from the group consisting of nitrogen, oxygen and sulphur is, for example, a 5- or 6-membered heterocyclic moiety which is a single ring or is fused to one or two benzo rings such as furyl, benzofuranyl, tetrahydrofuryl, chromanyl, thienyl, benzothienyl, pyridyl, piperidinyl, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, quinoxalinyl, quinazolinyl, cinnolinyl, pyrrolyl, pyrrolidinyl, indolyl, indolinyl, imidazolyl, benzimidazolyl, pyrazolyl, indazolyl, oxazolyl, benzoxazolyl, isoxazolyl, thiazolyl, benzothiazolyl, isothiazolyl, morpholinyl, 4H-1,4-benzoxazinyl, 4H-1,4-benzothiazinyl, 1,2,3-triazolyl, 1,2,4-triazolyl, oxadiazolyl, furazanyl, thiadiazolyl, tetrazolyl, dibenzofuranyl and dibenzothienyl, which may be attached through any available position including, for an appropriate X group such as, for example, carbonyl and methylene, through any available nitrogen atom and which may bear up to three substituents including a substituent on any available nitrogen atom.

Suitable values for the substituents which may be present within Q include, for example:

| | |
|---|---|
| for (1-4C)alkoxycarbonyl: | methoxycarbonyl, ethoxycarbonyl and tert-butoxycarbonyl; |
| for (1-4C)alkyl: | methyl, ethyl, propyl and isopropyl; |
| for (1-4C)alkoxy: | methoxy, ethoxy, propoxy and isopropoxy; |
| for N-(1-4C)alkylcarbamoyl: | N-methylcarbamoyl and N-ethylcarbamoyl; |
| for N,N-di-(1-4C)alkyl-carbamoyl: | N,N-dimethylcarbamoyl and N,N-diethylcarbamoyl; |
| for (1-4C)alkylamino: | methylamino, ethylamino and propylamino; |
| for di-(1-4C)alkylamino: | dimethylamino, N-ethyl-N-methylamino and diethylamino; |
| for (2-4C)alkanoylamino: | acetamido, propionamido and butyramido; |
| for (2-4C)alkanoyl: | acetyl, propionyl and butyryl; |
| for (2-4C)alkanoimidoyl: | acetimidoyl and propionoimidoyl; and |
| for (2-4C)alkanohydroximoyl: | acetohydroximoyl and propionohydroximoyl. |

A suitable value for the heteroaryl substituent or the heteroaryl group in a heteroaryl-containing substituent which comprises a 5- or 6-membered monocyclic heteroaryl ring containing up to 3 heteroatoms selected from the group consisting of oxygen, nitrogen and sulphur is, for example, furyl, thienyl, pyridyl, pyrazinyl, pyrimidinyl, pyridazinyl, pyrrolyl, pyrazolyl, oxazolyl, isoxazolyl, thiazolyl, isothiazolyl, 1,2,3-triazolyl, 1,2,4-triazolyl, oxadiazolyl, furazanyl and thiadiazolyl which may be attached through any available position including through any available nitrogen atom.

A suitable pharmaceutically-acceptable salt of an aminoheterocyclic derivative of the invention is, for example, an acid-addition salt of an aminoheterocyclic derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of an aminoheterocyclic derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention include, for example, aminoheterocyclic derivatives of the formula I or of the formula Ia, or pharmaceutically-acceptable salts thereof, wherein, unless otherwise stated, each of $G^1$, $G^2$, $G^3$, m, $R^1$, $M^1$, A, $M^2$, $M^3$, X and Q has any of the meanings defined hereinbefore or in this section concerning particular compounds of the invention:

(a) each of $G^1$, $G^2$ and $G^3$ is CH;

(b) each of $G^1$ and $G^2$ is CH and $G^3$ is N, or $G^1$ is N and each of $G^2$ and $G^3$ is CH;

(c) m is 1 and $R^1$ is hydrogen;

(d) A is a direct link to the carbonyl group;

(e) A is (1–4C)alkylene;

(f) $M^2$ is a group of the formula

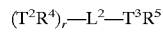

$(T^2R^4)_r$—$L^2$—$T^3R^5$ in which r is 1, $T^2$ is CH or N, $T^3$ is CH or N, $R^4$ is hydrogen or (1–4C)alkyl, $R^5$ is hydrogen or (1–4C) alkyl, or $R^4$ and $R^5$ together form a (1–4C)alkylene group, or $R^4$ is a (2–3C)alkylene group which is linked to a methylene group within $L^2$ forming a 5- or 6-membered ring involving $R^4$ and $T^2$, and $L^2$ is (1–4C)alkylene, and wherein 1 or 2 methylene groups within $L^2$ and the rings formed when $R^4$ and R5 or $R^4$ and $L^2$ are linked optionally bears a substituent selected from the group consisting of carboxy, (1–4C)alkoxycarbonyl, carbamoyl, N-(1–4C)alkylcarbamoyl, N,N-di-(1–4C) alkylcarbamoyl, pyrrolidin-1-ylcarbonyl, piperidinocarbonyl, morpholinocarbonyl, piperazin-1-ylcarbonyl, 4-(1–4C)alkylpiperazin-1-ylcarbonyl, N-phenylcarbamoyl, (1–4C)alkyl and phenyl-(1–4C) alkyl, and wherein any heterocyclic group in said substituent optionally bears 1 or 2 (1–4C)alkyl substituents, and wherein any phenyl group in $M^2$ optionally bears 1 or 2 substituents selected from the group consisting of halogeno, (1–4C)alkyl and (1–4C) alkoxy;

(g) $M^3$ is a direct link to X;

(h) $M^3$ is a group of the formula

$L^3$—$(NR^6)_s$ in which s is 1, $R^6$ is hydrogen or (1—4C)alkyl, $L^3$ is (1–4C)alkylene or carbonyl-(1–3C)alkylene, and wherein 1 or 2 methylene groups within $L^3$ optionally bears a substituent selected from the group consisting of (1–4C)alkyl, hydroxy- (1–4C)alkyl and phenyl-(1–4C)alkyl, and wherein any phenyl group in $M^3$ optionally bears 1 or 2 substituents selected from the group consisting of halogeno, (1–4C)alkyl and (1–4C) alkoxy;

(i) X is thio, sulphinyl or sulphonyl;

(j) X is sulphonyl;

(k) X is carbonyl, carbonyloxy, carbonylamino or N-(1–4C)alkylcarbonylamino;

(l) X is sulphonylamino or, when $T^3$ is CH and $M^3$ is a direct link to X, X may also be aminosulphonyl;

(m) X is methylene, (1–4C)alkylmethylene or di-(1–4C) alkylmethylene;

(n) Q is phenyl, naphthyl or phenyl-(1–4C)alkyl which optionally bears 1, 2 or 3 substituents selected from the group consisting of hydroxy, halogeno, cyano, trifluoromethyl, (1–4C)alkyl, (1–4C)alkoxy, phenyl, phenoxy, phenylthio, phenylsulphinyl, phenylsulphonyl, benzyl and benzoyl, and wherein the phenyl substituent or the phenyl group in a phenyl-containing substituent optionally bears 1 or 2 substituents selected from the group consisting of halogeno, (1–4C)alkyl and (1–4C) alkoxy;

(o) Q is phenyl which bears a phenyl substituent and optionally bears 1 or 2 substituents selected from the group consisting of hydroxy, halogeno, cyano, trifluoromethyl, (1–4C)alkyl and (1–4C)alkoxy, and wherein the phenyl substituent optionally bears up to 4 substituents selected from the group consisting of halogeno, trifluoromethyl, cyano, trifluoromethoxy, (1–4C)alkyl and (1–4C)alkoxy;

(p) Q is phenyl-(1–4C)alkyl, phenyl-(2–4C)alkenyl or phenyl-(2–4C)alkynyl which optionally bears 1, 2 or 3 substituents selected from the group consisting of halogeno, cyano, trifluoromethyl, (1–4C)alkyl and (1–4C)alkoxy;

(q) Q is phenyl-(2–4C)alkenyl which optionally bears 1, 2 or 3 substituents selected from the group consisting of halogeno, cyano, trifluoromethyl, (1–4C)alkyl and (1–4C)alkoxy;

(r) Q is phenyl or phenyl-(1–4C)alkyl which bears 1 substituent selected from the group consisting of heteroaryl, heteroaryloxy, heteroarylthio, heteroarylsulphinyl and heteroarylsulphonyl, wherein the heteroaryl substituent or the heteroaryl group in a heteroaryl-containing substituent comprises a 5- or 6-membered monocyclic heteroaryl ring containing up to 3 heteroatoms selected from the group consisting of nitrogen, oxygen and sulphur, and wherein said heteroaryl or heteroaryl-containing substituent optionally bears 1 or 2 substituents selected from the group consisting of halogeno, (1–4C)alkyl and (1–4C)alkoxy;

(s) Q is phenyl which bears 1 substituent selected from the group consisting of heteroaryl, heteroaryloxy, heteroarylthio and heteroarylsulphonyl, wherein the heteroaryl substituent or the heteroaryl group in a heteroaryl-containing substituent is selected from the group consisting of thienyl, pyridyl, pyrimidinyl, pyrazolyl, oxazolyl, thiazolyl, 1,2,3-triazolyl and 1;2,4-triazolyl, and wherein said heteroaryl or heteroaryl-containing substituent optionally bears 1 or 2 substituents selected from the group consisting of halogeno and (1–4C) alkyl;

(t) Q is naphthyl which optionally bears 1 or 2 substituents selected from the group consisting of hydroxy, halogeno, cyano, trifluoromethyl, (1–4C)alkyl and (1–4C)alkoxy;

(u) Q is a heterocyclic moiety containing up to 2 heteroatoms selected from the group consisting of benzofuranyl, quinolyl, tetrahydroquinolyl, isoquinolyl, quinoxalinyl, quinazolinyl, cinnolinyl, indolyl, benzimidazolyl, indazolyl, benzoxazolyl and benzothiazolyl, and Q optionally bears 1 or 2 substituents selected from the group consisting of halogeno, cyano, trifluromethyl, (1–4C)alkyl and (1–4C)alkoxy;

(v) Q is a heterocyclic moiety containing up to 2 heteroatoms selected from the group consisting of benzofuranyl, quinolyl, tetrahydroquinolyl, isoquinolyl, quinoxalinyl, quinazolinyl, cinnolinyl, indolyl, benzimidazolyl, indazolyl, benzoxazolyl, benzothiazolyl, dibenzofuranyl and dibenzothienyl, and Q optionally bears 1 or 2 substituents selected from the group consisting of halogeno, cyano, trifluoromethyl, (1–4C)alkyl and (1–4C)alkoxy;

(w) Q is a heterocyclic moiety containing up to 4 heteroatoms selected from the group consisting of furyl, thienyl, pyridyl, pyrimidinyl, pyrrolyl, pyrrolidinyl, imidazolyl, pyrazolyl, oxazolyl, isoxazolyl, thiazolyl, isothiazolyl, 1,2,3-triazolyl, 1,2,4-triazolyl, oxadiazolyl, thiadiazolyl and tetrazolyl, and Q optionally bears 1 or 2 substituents selected from the group consisting of halogeno, cyano, carboxy, carbamoyl, (1–4C)alkoxycarbonyl, (1–4C)alkyl, (1–4C)alkoxy, N-(1–4C)alkylcarbamoyl and N,N-di-(1–4C) alkylcarbamoyl;

(x) Q is a heterocyclic moiety containing up to 2 heteroatoms selected from the group consisting of thienyl, pyridyl, pyrimidinyl, imidazolyl, pyrazolyl, oxazolyl and thiazolyl, and Q optionally bears 1 or 2 substituents selected from the group consisting of halogeno, (1–4C) alkyl, (1–4C)alkoxy, phenyl, heteroaryl, phenoxy, phenylthio, phenylsulphinyl, phenylsulphonyl, heteroaryloxy, heteroarylthio, heteroarylsulphinyl, heteroarylsulphonyl, benzyl and benzoyl, wherein the heteroaryl substituent or the heteroaryl group in a heteroaryl-containing substituent is selected from the group consisting of thienyl, pyridyl, pyrimidinyl, pyrazolyl, oxazolyl and thiazolyl, and wherein said phenyl, phenyl-containing, heteroaryl or heteroaryl-containing substituent optionally bears 1 or 2 substituents selected from the group consisting of halogeno, (1–4C)alkyl and (1–4C)alkoxy; or (y) Q is a heterocyclic moiety containing up to 2 heteroatoms selected from the group consisting of thienyl, pyridyl, oxazolyl and thiazolyl, and Q bears a substituent selected from the group consisting of phenyl, thienyl, pyridyl, pyrimidinyl, oxazolyl and thiazolyl, which substituent optionally bears 1 or 2 substituents selected from the group consisting of halogeno, (1–4C) alkyl and (1–4C)alkoxy, and Q optionally bears a further substituent selected from the group consisting of halogeno and (1–4C)alkyl;

or a pharmaceutically-acceptable salt thereof.

A preferred compound of the invention is an aminoheterocyclic derivative of the formula I wherein each of $G^1$, $G^2$ and $G^3$ is CH, or each of $G^1$ and $G^2$ is CH and $G^3$ is N, or $G^1$ is N and each of $G^2$ and $G^3$ is CH;

m is 1 or 2 and each $R^1$ is independently selected from hydrogen, amino, fluoro, chloro, bromo, cyano, methyl, ethyl and methoxy;

$M^1$ is a group of the formula

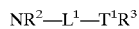

in which $R^2$ and $R^3$ together form an ethylene group, $L^1$ is methylene or ethylene, and $T^1$ is CH or N, and wherein 1 or 2 methylene groups within $L^1$ and the ring formed when $R^2$ and $R^3$ are linked optionally bears a substituent selected from the group consisting of methyl and ethyl;

A is a direct link to the carbonyl group or A is methylene;

$M^2$ is a group of the formula

in which r is 0 or 1, $T^2$ is CH or N, $T^3$ is N, $R^4$ is hydrogen, methyl or ethyl, $R^5$ is hydrogen, methyl or ethyl, or $R^4$ and $R^5$ together form a methylene, ethylene, trimethylene or methylenecarbonyl group, or $R^4$ is an ethylene group which is linked to a methylene group within $L^2$ forming a 5- or 6-membered ring involving $R^4$ and $T^2$, and $L^2$ is methylene, ethylene, trimethylene, methylenecarbonyl or phenylene, and wherein 1 or 2 methylene groups within $L^2$ and the ring formed when $R^4$ and $R^5$ are linked optionally bears a substituent selected from the group consisting of oxo, carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, morpholinocarbonyl, piperazin-1-ylcarbonyl, 4-methylpiperazin-1-ylcarbonyl, methyl, ethyl, carboxymethyl, methoxycarbonylmethyl, ethoxycarbonylmethyl, hydroxymethyl, methoxymethyl and benzyl, and wherein the pyrrolidin-1-ylcarbonyl, piperidinocarbonyl, morpholinocarbonyl, piperazin-1-ylcarbonyl or 4-methylpiperazin-1-ylcarbonyl substituent optionally bears a methyl or ethyl substituent;

$M^3$ is a direct link to X, or $M^3$ is a group of the formula $$L^3\text{—}(NR^6)_s$$

in which s is 1, $R^6$ is hydrogen and $L^3$ is carbonylmethylene or carbonylethylene;

X is thio, sulphinyl, sulphonyl, carbonyl, carbonyloxy or methylene; and Q is phenyl, naphthyl, benzyl, phenethyl, styryl, 2-phenylethynyl, dibenzofuranyl, biphenylyl, pyridylphenyl or pyridylthienyl, and Q optionally bears 1, 2 or 3 substituents selected from the group consisting of hydroxy, amino, fluoro, chloro, bromo, iodo, tyano, trifluoromethyl, nitro, carboxy, carbamoyl, methoxycarbonyl, ethoxycarbonyl, methyl, ethyl, methoxy and ethoxy; or a pharmaceutically-acceptable salt thereof.

A further preferred compound of the invention is an aminoheterocyclic derivative of the formula I wherein each of $G^1$, $G^2$ and $G^3$ is CH, or each of $G^1$ and $G^2$ is CH and $G^3$ is N, or $G^1$ is N and each of $G^2$ and $G^3$ is CH;

m is 1 or 2 and each R is independently selected from hydrogen, amino, chloro, methyl and ethyl;

$M^1$ is a group of the formula $$NR^2\text{—}L^1\text{—}T^1R^3$$

in which $R^2$ and $R^3$ together form an ethylene group, $L^1$ is ethylene, and
$T^1$ is CH or N;

A is a direct link to the carbonyl group or A is methylene;

$M^2$ is a group of the formula $$(T^2R^4)_r\text{—}L^2\text{—}T^3R^5$$

in which r is 0 or 1, is N, $T^3$ is N, $R^4$ is hydrogen, $R^5$ is hydrogen, or $R^4$ and $R^5$ together form an ethylene group, or $R^4$ is an ethylene group which is linked to a methylene group $L^2$ forming a 5- or 6-membered ring involving $R^4$ and $T^2$, and $L^2$ is methylene, ethylene or phenylene, and wherein 1 or 2 methylene groups within $L^2$ and the ring formed when $R^4$ and $R^5$ are linked optionally bears a substituent selected from the group consisting of carboxy, methoxycarbonyl, ethoxycarbonyl, pyrrolidin-1-ylcarbonyl, piperidinocarbonyl, morpholinocarbonyl, piperazin-1-ylcarbonyl, 4-methylpiperazin-1-ylcarbonyl, methyl, ethyl and benzyl, and wherein the pyrrolidin-1-ylcarbonyl, piperidinocarbonyl, morpholinocarbonyl, piperazin-1-ylcarbonyl or 4-methylpiperazin-i-ylcarbonyl substituent optionally bears a methyl or ethyl substituent;

$M^3$ is a direct link to X, or $M^3$ is a group of the formula $$L^3\text{—}(NR^6)_s$$

in which s is 1, $R^6$ is hydrogen and $L^3$ is carbonylmethylene;

X is sulphonyl; and

Q is phenyl, naphthyl, benzyl, phenethyl, styryl, 2-phenylethynyl, dibenzofuranyl, biphenylyl, pyridylphenyl or pyridylthienyl, and Q optionally bears 1 or 2 substituents selected from the group consisting of fluoro, chloro, bromo, iodo, methyl, ethyl, methoxy and ethoxy;

or a pharmaceutically-acceptable salt thereof.

A further preferred compound of the invention is an aminoheterocyclic derivative of the formula Ia wherein each of $G^1$ and $G^2$ is CH;

m is 1 and $R^1$ is hydrogen;

$M^1$ is a group of the formula $$NR^2\text{—}L^1\text{—}T^1R^3$$

in which $R^2$ and $R^3$ together form an ethylene group, $L^1$ is methylene or ethylene, and
$T^1$ is CH or N, and wherein 1 or 2 methylene groups within $L^1$ and the ring formed when $R^2$ and $R^3$ are linked optionally bears a substituent selected from the group consisting of methyl and ethyl;

A is a direct link to the carbonyl group or A is methylene;

$M^2$ is a group of the formula $$(T^2R^4)_r\text{—}L^2\text{—}T^3R^5$$

in which r is 1, $T^2$ is CH or N, $T^3$ is N, $R^4$ is hydrogen, methyl or ethyl, $R^5$ is hydrogen, methyl or ethyl, or $R^4$ and $R^5$ together form an ethylene group, or $R^4$ is an ethylene group which is linked to a methylene group within $L^2$ forming a 5- or 6-membered ring involving $R^4$ and $T^2$, and $L^2$ is methylene, ethylene or trimethylene, and wherein 1 or 2 methylene groups within $L^2$ and the ring formed when $R^4$ and $R^5$ are linked optionally bears a substituent selected from the group consisting of carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, methyl, ethyl and benzyl, and wherein the pyrrolidin-1-ylcarbonyl or piperidinocarbonyl substituent optionally bears a methyl or ethyl substituent;

$M^3$ is a direct link to X, or $M^3$ is a group of the formula $$L^3\text{—}(NR^6)_s$$

in which s is 1, $R^6$ is hydrogen and $L^3$ is carbonylmethylene or carbonylethylene;

X is sulphonyl; and

Q is phenyl, 2-naphthyl or benzyl which optionally bears 1 or 2 substituents selected from the group consisting of fluoro, chloro, bromo and trifluoromethyl;

or a pharmaceutically-acceptable salt thereof.

A further preferred compound of the invention is an aminoheterocyclic derivative of the formula I wherein $G^3$ is CH or N and each of $G^1$ and $G^2$ is CH;

m is 1 and $R^1$ is hydrogen;

$M^1$ is a group of the formula

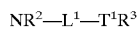

$NR^2—L^1—T^1R^3$ in which $R^2$ and $R^3$ together form an ethylene group, $L^1$ is methylene or ethylene, and $T^1$ is CH or N, and wherein 1 or 2 methylene groups within $L^1$ and the ring formed when $R^2$ and $R^3$ are linked optionally bears a substituent selected from the group consisting of methyl and ethyl;

A is a direct link to the carbonyl group or A is methylene;

$M^2$ is a group of the formula

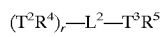

$(T^2R^4)_r—L^2—T^3R^5$ in which r is 1, $T^2$ is CH or N, $T^3$ is N, $R^4$ is hydrogen, methyl or ethyl, $R^5$ is hydrogen, methyl or ethyl, or $R^4$ and $R^5$ together form a methylene, ethylene or trimethylene group, or $R^4$ is an ethylene group which is linked to a methylene group within $L^2$ forming a 5- or 6-membered ring involving R and T, and $L^2$ is methylene, ethylene or trimethylene, and wherein 1 or 2 methylene groups within L and the ring formed when $R^4$ and $R^5$ are linked optionally bears a substituent selected from the group consisting of oxo, carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, morpholinocarbonyl, methyl, ethyl and benzyl, and wherein the pyrrolidin-1-ylcarbonyl or piperidinocarbonyl substituent optionally bears one or two methyl or ethyl substituents;

$M^3$ is a direct link to X, or $M^3$ is a group of the formula

$L^3—(NR^6)_s$ in which s is 1, $R^6$ is hydrogen and $L^3$ is carbonylmethylene or carbonylethylene;

X is sulphonyl; and

Q is 3- or 4-biphenylyl which optionally bears, in the ring attached to X, 1 or 2 substituents selected from the group consisting of hydroxy, fluoro, chloro, bromo, cyano, trifluoromethyl, methyl, ethyl, methoxy and ethoxy and which optionally bears in the terminal phenyl group up to 4 substituents selected from the group consisting of fluoro, chloro, bromo, trifluoromethyl, cyano, trifluoromethoxy, methyl, ethyl, methoxy and ethoxy;

or a pharmaceutically-acceptable salt thereof.

A further preferred compound of the invention is an aminoheterocyclic derivative of the formula I wherein $G^3$ is CH or N and each of $G^1$ and $G^2$ is CH;

m is 1 and $R^1$ is hydrogen;

$M^1$ is a group of the formula

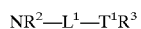

$NR^2—L^1—T^1R^3$ in which $R^2$ and $R^3$ together form an ethylene group, $L^1$ is methylene or ethylene, and $T^1$ is CH or N, and wherein 1 or 2 methylene groups within $L^1$ and the ring formed when $R^2$ and $R^3$ are linked optionally bears a substituent selected from the group consisting of methyl and ethyl;

A is a direct link to the carbonyl group or A is methylene;

$M^2$ is a group of the formula

$(T^2R^4)_r—L^2—T^3R^5$ in which r is 1, $T^2$ is CH or N, $T^3$ is N, $R^4$ is hydrogen, methyl or ethyl, $R^5$ is hydrogen, methyl or ethyl, or $R^4$ and $R^5$ together form a methylene, ethylene or trimethylene group, or $R^4$ is an ethylene group which is linked to a methylene group within $L^2$ forming a 5- or 6-membered ring involving R and T, and $L^2$ is methylene, ethylene or trimethylene, and wherein 1 or 2 methylene groups within $L^2$ and the ring formed when $R^4$ and $R^5$ are linked optionally bears a substituent selected from the group consisting of oxo, carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, morpholinocarbonyl, methyl, ethyl and benzyl, and wherein the pyrrolidin-1-ylcarbonyl or piperidinocarbonyl substituent optionally bears one or two methyl or ethyl substituents;

$M^3$ is a direct link to X, or $M^3$ is a group of the formula

$L^3—(NR^6)_s$ in which s is 1, $R^6$ is hydrogen and $L^3$ is carbonylmethylene or carbonylethylene;

X is sulphonyl; and

Q is benzyl, phenethyl, styryl or 2-phenylethynyl which optionally bears 1, 2 or 3 substituents selected from the group consisting of fluoro, chloro, bromo, cyano, trifluoromethyl, methyl, ethyl, methoxy and ethoxy;

or a pharmaceutically-acceptable salt thereof.

A further preferred compound of the invention is an aminoheterocyclic derivative of the formula Ia wherein each of $G^1$ and $G^2$ is CH;

m is 1 and $R^1$ is hydrogen;

$M^1$ is a group of the formula

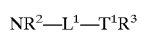

$NR^2—L^1—T^1R^3$ in which $R^2$ and $R^3$ together form an ethylene group, $L^1$ is methylene or ethylene, and $T^1$ is CH or N, and wherein 1 or 2 methylene groups within $L^1$ and the ring formed when $R^2$ and $R^3$ are linked optionally bears a substituent selected from the group consisting of methyl and ethyl;

A is a direct link to the carbonyl group or A is methylene;
M² is a group of the formula

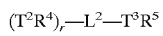

in which r is 1, T² is CH or N, T³ is N, p1 R⁴ is hydrogen, methyl or ethyl, R⁵ is hydrogen, methyl or ethyl, or R⁴ and R⁵ together form an ethylene group, or R⁴ is an ethylene group which is linked to a methylene group within L² forming a 5- or 6-membered ring involving R⁴ and T², and L² is methylene, ethylene or trimethylene, and wherein 1 or 2 methylene groups within L² and the ring formed when R⁴ and R⁵ are linked optionally bears a substituent selected from the group consisting of carboxy, methoxycarbonyl, ethoxycarbonyl, carbamoyl, N-metylcarbamoyl, N,N-dimethylcarbamoyl, pyrrolidin-1-ylcarbonyl, piperidinocarbonyl, methyl, ethyl and benzyl, and wherein the pyrrolidin-1-ylcarbonyl or piperidinocarbonyl substituent optionally bears a methyl or ethyl substituent;

M³ is a direct link to X, or M³ is a group of the formula

in which s is 1, R⁶ is hydrogen and L³ is carbonylmethylene or carbonyl ethylene;

X is sulphonyl; and

Q is 2-thienyl which bears a substituent selected from the group consisting of phenyl, thienyl, pyridyl and pyrimidinyl and wherein said substituents optionally bear 1 or 2 substituents selected from the group consisting of fluoro, chioro, bromo and methyl;

or a pharmaceutically-acceptable salt thereof.

A further preferred compound of the invention is an aminoheterocyclic derivative of the formula I wherein G³ is CH or N and each of G¹ and G² is CH;
m is 1 and R¹ is hydrogen;
M¹ is a group of the formula

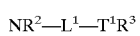

in which R² and R³ together form an ethylene group,
L¹ is methylene or ethylene, and
T¹ is CH or N,
and wherein 1 or 2 methylene groups within L¹ and the ring formed when R² and R³ are linked optionally bears a substituent selected from the group consisting of methyl and ethyl;

A is a direct link to the carbonyl group or A is methylene;
M² is a group of the formula

in which r is 1, T²h is CH or N, T³ is N,
R⁴ is hydrogen, methyl or ethyl, R⁵ is hydrogen, methyl or ethyl, or R⁴ and R⁵ together form an ethylene group, or R⁴ is an ethylene group which is linked to a methylene group within L² forming a 5- or 6-membered ring involving R⁴ and T², and L² is methylene,.ethylene or trimethylene, and wherein 1 or 2 methylene groups within L² and the ring formed when R⁴ and R⁵ are linked optionally bears a substituent selected from the group consisting of carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, morpholinocarbonyl, methyl, ethyl and benzyl, and wherein the pyrrolidin-1-ylcarbonyl or piperidinocarbonyl substituent optionally bears a methyl or ethyl substituent;

M³ is a direct link to X, or M³ is a group of the formula

in which s is 1, R⁶ is hydrogen and L³ is carbonylmethylene or carbonylethylene;

X is sulphonyl; and

Q is 3- or 4-biphenylyl which optionally bears in the terminal phenyl group up to 4 substituents selected from the group consisting of fluoro, chloro, bromo, trifluoromethyl, trifluoromethoxy, methyl and methoxy;

or a pharmaceutically-acceptable salt thereof.

A further preferred compound of the invention is an aminoheterocyclic derivative of the formula I wherein G³ is CH or N and each of G¹ and G² is CH;
m is 1 and R¹ is hydrogen;
M¹ is a group of the formula

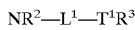

in which R² and R³ together form an ethylene group,
L¹ is methylene or ethylene, and
T¹ is CH or N,
and wherein 1 or 2 methylene groups within and the ring formed when R² and R³ are linked optionally bears a substituent selected from the group consisting of methyl and ethyl;

A is a direct link to the carbonyl group or A is methylene;
M² is a group of the formula

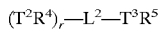

in which r is 1, T² is CH or N, T³ is N,
R⁴ is hydrogen, methyl or ethyl, R⁵ is hydrogen, methyl or ethyl, or R⁴ and R⁵ together form an ethylene group, or R⁴ is an ethylene group which is linked to a methylene group within L² forming a 5- or 6-membered ring involving R⁴ and T², and L² is methylene, ethylene or trimethylene, and wherein 1 or 2 methylene groups within L² and the ring formed when R⁴ and R⁵ are linked optionally bears a substituent selected from the group consisting of carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, morpholinocarbonyl, methyl, ethyl and benzyl, and wherein the pyrrolidin-1-ylcarbonyl or piperidinocarbonyl substituent optionally bears a methyl or ethyl substituent;

M³ is a direct link to X, or M³ is a group of the formula

in which s is 1, R⁶ is hydrogen and L³ is carhonylmethylene or carbonylethylene;

X is sulphonyl; and

Q is phenethyl, styryl or 2-phenylethynyl which optionally bears 1, 2 or 3 substituents selected from the group consisting of fluoro, chloro, bromo, trifluoromethyl, methyl and methoxy;

or a pharmaceutically-acceptable salt thereof.

A further preferred compound of the invention is an amninoheterocyclic derivative of the formula Ia wherein each of $G^1$ and $G^2$ is CH;

m is 1 and $R^1$ is hydrogen;

$M^1$ is a group of the formula $$NR^2—L^1—T^1R^3$$

in which $R^2$ and $R^3$ together form an ethylene group, $L^1$ is ethylene, and
$T^1$ is CH or N;

A is a direct link to the carbonyl group;

$M^2$ is a group of formula $$(T^2R^4)_r—L^2—T^3R^5$$

in which r is 1, $T^2$ is N and $T^3$ is N,
$R^4$ is hydrogen, $R^5$ is hydrogen, or $R^4$ and $R^5$ together form an ethylene group, and
$L^2$ is ethylene,
and wherein 1 methylene group within $L^2$ optionally bears a substituent selected from carboxy, ethoxycarbonyl, N-methylcarbamoyl, piperidinocarbonyl and benzyl;

$M^3$ is a direct link to X, or $M^3$ is a group of the formula $$L^3—(NR^6)_s$$

in which s is 1, $R^6$ is hydrogen and $L^3$ is carbonylmethylene;

X is sulphonyl; and

Q is 2-naphthyl;

or a pharmaceutically-acceptable acid-addition salt thereof.

A further preferred compound of the invention is an aminoheterocyclic derivative of the formula Ia wherein each of $G^1$ and $G^2$ is CH, $G^1$ is N and $G^2$ is CH, or $G^1$ is CH and $G^2$ is N;

m is 1 and $R^1$ is hydrogen;

$M^1$ is a group of the formula $$NR^2—L^1—T^1R^3$$

in which $R^2$ and $R^3$ together form an ethylene group,
$L^1$ is ethylene, and
$T^1$ is CH or N;

A is a direct link to the carbonyl group;

$M^2$ is a group of formula $$(T^2R^4)_r—L^2—T^3R^5$$

in which r is 1, $T^2$ is N and $T^3$ is N,
$R^4$ is hydrogen, $R^5$ is hydrogen, or $R^4$ and $R^5$ together form an ethylene group, and
$L^2$ is ethylene,
and wherein 1 methylene group within $L^2$ optionally bears a substituent selected from carboxy, ethoxycarbonyl, N-methylcarbamoyl, piperidinocarbonyl, methyl and benzyl;

$M^3$ is a direct link to X, or $M^3$ is a group of the formula $$L^3—(NR^6)_s$$

in which s is 1, $R^6$ is hydrogen and $L^3$ is carbonylmethylene;

X is sulphonyl; and

Q is 2-naphthyl which optionally bears 1 or 2 substituents selected from the group consisting of fluoro, chloro, bromo, trifluoromethyl, methyl, methoxy and ethoxy;

or a pharmaceutically-acceptable acid-addition salt thereof.

A further preferred compound of the invention-is an aminoheterocyclic derivative of the formula I wherein each of $G^1$, $G^2$ and $G^3$ is CH;

m is 1 and $R^1$ is hydrogen;

$M^1$ is a group of the formula $$NR^2—L^1—T^1R^3$$

in which $R^2$ and $R^3$ together form an ethylene group,
$L^1$ is ethylene, and
$T^1$ is CH or N;

A is a direct link to the carbonyl group;

$M^2$ is a group of formula $$(T^2R^4)_r—L^2—T^3R^5$$

in which r is 1, $T^2$ is N and $T^3$ is N,
$R^4$ is hydrogen, $R^5$ is hydrogen, or $R^4$ and $R^5$ together form an ethylene group, and
$L^2$ is ethylene,
and wherein 1 methylene group within $L^2$ optionally bears a substituent selected from carboxy, ethoxycarbonyl, N-methylcarbamoyl, piperidinocarbonyl and benzyl;

$M^3$ is a direct link to X, or $M^3$ is a group of the formula $$L^3—(NR^6)_s$$

in which s is 1, $R^6$ is hydrogen and $L^3$ is carbonylmethylene;

X is sulphonyl; and

Q is 4-biphenylyl which bears in the terminal phenyl group 1 or 2 substituents selected from fluoro, chloro, bromo, trifluoromethyl and methyl;

or a pharmaceutically-acceptable acid-addition salt thereof.

A further preferred compound of the invention is an aminoheterocyclic derivative of the formula I wherein each of $G^1$, $G^2$ and $G^3$ is CH, $G^1$ is N and each of $G^2$ and $G^3$ is CH, or $G^3$ is N and each of $G^1$ and $G^2$ is CH;

m is 1 and $R^1$ is hydrogen;

$M^1$ is a group of the formula $$NR^2—L^1—T^1R^3$$

in which $R^2$ and $R^3$ together form an ethylene group,
$L^1$ is ethylene, and
$T^1$ is CH or N;

A is a direct link to the carbonyl group;

$M^2$ is a group of formula

in which r is 1, $T^2$ is N and $T^3$ is N,
$R^4$ is hydrogen, $R^5$ is hydrogen, or $R^4$ and $R^5$ together form an ethylene group, and
$L^2$ is ethylene,
and wherein 1 methylene group within $L^2$ optionally bears a substituent selected from carboxy, ethoxycarbonyl, N-methylcarbamoyl, piperidinocarbonyl, methyl and benzyl;
$M^3$ is a direct link to X, or $M^3$ is a group of the formula

in which s is 1, $R^6$ is hydrogen and $L^3$ is carbonylmethylene;
X is sulphonyl; and
Q is 4-biphenylyl which bears in the terminal phenyl group 1 or 2 substituents selected from fluoro, chloro, bromo, trifluoromethyl and methyl;
or a pharmaceutically-acceptable acid-addition salt thereof.

A further preferred compound of the invention is an aminoheterocyclic derivative of the formula I
wherein each of $G^1$, $G^2$ and $G^3$ is CH;
m is 1 and $R^1$ is hydrogen;
$M^1$ is a group of the formula $$NR^2-L^1-T^1R^3$$

in which $R^2$ and $R^3$ together form an ethylene group,
$L^1$ is ethylene, and
$T^1$ is CH or N;
A is a direct link to the carbonyl group;
$M^2$ is a group of formula

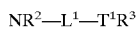

in which r is 1, $T^2$ is N and $T^3$ is N,
$R^4$ is hydrogen, $R^5$ is hydrogen, or $R^4$ and $R^5$ together form an ethylene group, and
$L^2$ is ethylene,
and wherein 1 methylene group within $L^2$ optionally bears a substituent selected from carboxy, ethoxycarbonyl, N-methylcarbamoyl, piperidinocarbonyl and benzyl;
$M^3$ is a direct link to X, or $M^3$ is a group of the formula

in which s is 1, $R^6$ is hydrogen and $L^3$ is carbonylmethylene;
X is sulphonyl; and
Q is styryl which optionally bears 1 or 2 substituents selected from the group consisting of fluoro, chloro, bromo, trifluoromethyl and methyl;
or a pharmaceutically-acceptable acid-addition salt thereof.

A further preferred compound of the invention is an aminoheterocyclic derivative of the formula I
wherein each of $G^1$, $G^2$ and $G^3$ is CH, $G^1$ is N and each of $G^2$ and $G^3$ is CH, or $G^3$ is N and each of $G^1$ and $G^2$ is CH;

m is 1 and $R^1$ is hydrogen;
$M^1$ is a group of the formula $$NR^2-L^1-T^1R^3$$

in which $R^2$ and $R^3$ together form an ethylene group,
$L^1$ is ethylene, and
$T^1$ is CH or N;
A is a direct link to the carbonyl group;
$M^2$ is a group of formula

in which r is 1, $T^2$ is N and $T^3$ is N,
$R^4$ is hydrogen, $R^5$ is hydrogen, or $R^4$ and $R^5$ together form an ethylene group, and
$L^2$ is ethylene,
and wherein 1 methylene group within $L^2$ optionally bears a substituent selected from carboxy, ethoxycarbonyl, N-methylcarbamoyl, piperidinocarbonyl, methyl and benzyl;
$M^3$ is a direct link to X, or $M^3$ is a group of the formula

in which s is 1, $R^6$ is hydrogen and $L^3$ is carbonylmethylene;
X is sulphonyl; and
Q is styryl which optionally bears 1 or 2 substituents selected from the group consisting of fluoro, chioro, bromo, trifluoromethyl and methyl;
or a pharmaceutically-acceptable acid-addition salt thereof.

A specific preferred compound of the invention is the following aminoheterocyclic derivative of the formula I:
2-(2-naphthalenesulphonamido)-N-{1-piperidinocarbonyl-2-[1-(4-pyridyl)-piperidin-4-ylcarbonylamino]ethyl}acetamide,
1-(2-naphthylsulphonyl)-4-[1-(4-pyridyl)piperidin-4-ylcarbonyl]-piperazine,
2-(2-naphthalenesulphonamido)-N-(1-piperidinocarbonyl-2-{2-[1-(4-pyridyl)piperidin-4-yl]acetamido}ethyl)acetamide,
2-(2-naphthalenesulphonamido)-N-(1-piperidinocarbonyl-2-{2-[4-(4-pyridyl)piperazin-1-yl]acetamido}ethyl)acetamide,
ethyl 2-(2-naphthalenesulphonamido)-3-[1-(4-pyridyl)piperidin-4-ylcarbonylamino]propionate,
1-[1-(2-naphthylsulphonyl)piperidin-4-ylcarbonyl]-4-(4-pyridyl)-piperazine or
2-(2-naphthalenesulphonamido)-N-{1-phenyl-3-[1-(4-pyridyl)piperidin-4-ylcarbonylamino]prop-2-yl}acetamide;
or a pharmaceutically-acceptable acid-addition salt thereof.

A further specific preferred compound of the invention is the following aminoheterocyclic derivative of the formula I:
4-[1-(4-pyridyl)piperidin-4-ylcarbonyl]-1-[(E)-styrylsulphonyl]-piperazine,
1-[(E)-4-chlorostyrylsulphonyl]-4-[1-(4-pyridyl)piperidin-4-ylcarbonyl]piperazine,
1-[(E)-4-methylstyrylsulphonyl]-4-[1-(4-pyridyl)piperidin-4-ylcarbonyl]piperazine, 4-[(E)-4-chlorostyrylsulphonyl]-2-methyl-1-[1-(4-pyridyl)piperidin-4-ylcarbonyl]piperazine, 1-(4-biphenylylsulphonyl)-4-[1-(4-pyridyl)piperidin-4-ylcarbonyl]-piperazine, 1- (4'-chloro-4-biphenylylsulphonyl)-4-[1-(4-pyridyl)-piperidin-4-ylcarbonyl]piperazine or 1-[(E)-4-chlorostyrylsulphonyl]-4-[1-(4-pyrimidinyl)piperidin-4-ylcarbonyl]piperazine;

or a pharmaceutically-acceptable acid-addition salt thereof.

A further specific preferred compound of the invention is the following aminoheterocyclic derivative of the formula I:

1-(7-chloronaphth-2-ylsulphonyl)-4-[1-(4-pyridyl)piperidin-4-ylcarbonyl]piperazine, 2-ethoxycarbonyl-4-(2-naphthylsulphonyl)-1-[1-(4-pyridyl)piperidin-4-ylcarbonyl]piperazine or 1-(2-naphthylsulphonyl)-4-[1-(4-pyrimidinyl)piperidin-4-ylcarbonyl]-piperazine;

or a pharmaceutically-acceptable acid-addition salt thereof.

A further specific preferred compound of the invention is the following aminoheterocyclic derivative of the formula I:

1-[(E)-4-fluorostyrylsulphonyl]-4-[1-(4-pyridyl)piperidin-4-ylcarbonyl]piperazine, 1-[(E)-4-bromostyrylsulphonyl]-4-[1-(4-pyridyl)piperidin-4-ylcarbonyl]-piperazine or 1-(4'-bromo-4-biphenylylsulphonyl)-4-[1-(4-pyridyl)piperidin-4-ylcarbonyl]piperazine;

or a pharmaceutically-acceptable acid-addition salt thereof.

A further specific preferred compound of the invention is the following aminoheterocyclic derivative of the formula I:

1-(6-chloronaphth-2-ylsulphonyl)-4-[1-(4-pyridyl)piperidin-4-ylcarbonyl]piperazine, 1-(6-bromonaphth-2-ylsulphonyl)-4-[1-(4-pyridyl)piperidin-4-ylcarbonyl]piperazine, 1-(6-chloronaphth-2-ylsulphonyl)-4-[4-(4-pyridyl)piperazin-1-ylcarbonyl]piperazine, 4-(2-naphthylsulphonyl)-2-piperidinocarbonyl-1-[1-(4-pyridyl)-piperidin-4-ylcarbonyl]piperazine, 4-(6-chloronaphth-2-ylsulphonyl)-2-ethoxycarbonyl-1-[1-(4-pyridyl)-piperidin-4-ylcarbonyl]piperazine, 2-carboxy-4-(6-chloronaphth-2-ylsulphonyl)-1-[1-(4-pyridyl)piperidin-4-ylcarbonyl]piperazine, 1-(6-chloronaphth-2-ylsulphonyl)-4-[1-(4-pyrimidinyl)piperidin-4-ylcarbonyl]piperazine, 4-[1-(2-aminopyrimidin-4-yl)piperidin-4-yldarbonyl]-1-(6-chloronaphth-2-ylsulphonyl)piperazine or 1-(6-chloronaphth-2-ylsulphonyl)-4-[1-(4-pyridazinyl)piperidin-4-ylcarbonyl]piperazine;

or a pharmaceutically-acceptable acid-addition salt thereof.

A further specific preferred compound of the invention is the following aminoheterocyclic derivative of the formula I:

4-(6-bromonaphth-2-ylsulphonyl)-2-ethoxycarbonyl-1-[1-(4-pyridyl)-piperidin-4-ylcarbonyl]piperazine, 4-(6-bromonaphth-2-ylsulphonyl)-2-carboxy-1-[1-(4-pyridyl)piperidin-4-ylcarbonyl]piperazine, 4-(6-bromonaphth-2-ylsulphonyl)-2-morpholinocarbonyl-1-[1-(4-pyridyl)-piperidin-4-ylcarbonyl]piperazine, 4-(6-chloronaphth-2-ylsulphonyl)-2-methoxycarbonyl-1-[1-(4-pyridyl)-piperidin-4-ylcarbonyl]piperazine or 2-carboxy-4-(6-chloronaphth-2-ylsulphonyl)-1-[1-(4-pyridyl)piperidin-4-ylcarbonyl]piperazine;

or a pharmaceutically-acceptable salt thereof.

An aminoheterocyclic derivative of the formula I or of the formula Ia, or a pharmaceutically-acceptable salt thereof, may be prepared by any process known to be applicable to the preparation of structurally-related compounds. Such procedures are provided as a further feature of the invention and are illustrated by the following representative processes in which, unless otherwise stated $G^1$, $G^2$, $G^3$, m, $R^1$, $M^1$, A, $M^2$, $M^3$, X and Q (and any groups defined therein) have any of the meanings defined hereinbefore, provided that when there is an amino, alkylamino, hydroxy or carboxy group in $R^1$, $M^1$, $M^2$, $M^3$ or Q then any such group is protected by a conventional protecting group which may be removed when so desired by conventional means.

Necessary starting materials may be obtained by standard procedures of organic chemistry. The preparation of such starting materials is illustrated within the accompanying Examples; alternatively analogous procedures to those illustrated may be employed by applying no more than the ordinary skill of an organic chemist.

(a) For the production of those compounds of the formula I wherein $M^2$ is a group of the formula

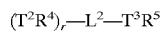

in which $T^2$ is N and r is 1, the reaction, conveniently in the presence of a suitable base, of an acid of the formula II, or a reactive derivative thereof, with an amine of the formula

A suitable reactive derivative of an acid of the formula II is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as N-hydroxybenzotriazole or N-hydroxysuccinimide; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo-[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, -78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

(b) For the production of those compounds of the formula I wherein $M^2$ is a group of the formula

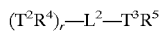
$(T^2R^4)_r—L^2—T^3R^5$ in which $T^3$ is N, and wherein $M^3$ is a direct link to X, the reaction, conveniently in the presence of a suitable base as defined hereinbefore, of an amine of the formula III with a compound of the formula Z—X—Q wherein Z is a displaceable group.

A suitable value for the displaceable group Z is, for example, a halogeno or sulphonyloxy group, for example a fluoro, chloro, bromo, mesyloxy or 4-tolylsulphonyloxy group.

The reaction is conveniently performed in a suitable inert solvent or diluent as defined hereinbefore and at a temperature in the range, for example, 0° C. to 150° C., conveniently at or near ambient temperature.

(c) For the production of those compounds of the formula I wherein $M^1$ is a group of the formula

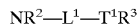
$NR^2—L^1—T^1R^3$ in which $T^1$ is N, and wherein A is a direct link to the carbonyl group, the reaction, conveniently in the presence of a suitable base as defined hereinbefore, of an amine of the formula IV with an acid of the formula

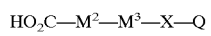
$HO_2C—M^2—M^3—X—Q$ or a reactive derivative thereof as defined hereinbefore.

The reaction is conveniently performed in a suitable inert solvent or diluent as defined hereinbefore and at a temperature in the range, for example, 0° to 150° C., conveniently at or near ambient temperature.

(d) For the production of those compounds of the formula I wherein $M^2$ is a group of the formula

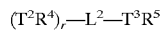
$(T^2R^4)_r—L^2—T^3R^5$ in which $T^3$ is N, and wherein $M^3$ is a group of the formula

$L^3—(NR^6)_s$ in which $L^3$ is carbonylmethylene, the reaction, conveniently in the presence of a suitable base as defined hereinbefore, of an amine of the formula III with an acid of the formula

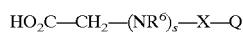
$HO_2C—CH_2—(NR^6)_s—X—Q$ or a reactive derivative thereof as defined hereinbefore.

The reaction is conveniently performed in a suitable inert solvent or diluent as defined hereinbefore and at a temperature in the range, for example, 0° to 150° C., conveniently at or near ambient temperature.

(e) For the production of those compounds of the formula I wherein $M^2$ is a group of the formula

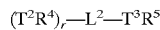
$(T^2R^4)_r—L^2—T^3R^5$ in which $T^3$ is N, and wherein $M^3$ is a direct link to X and X is carbonylamino, the reaction of an amine of the formula III with an isocyanate of the formula

OCN—X—Q

The reaction is conveniently performed in a suitable inert solvent or diluent as defined hereinbefore and at a temperature in the range, for example, 0° to 60° C., conveniently at or near ambient temperature.

(f) The reaction, conveniently in the presence of a suitable base as defined hereinbefore, of a compound of the formula V wherein Z is a displaceable group as defined hereinbefore, with an amine of the formula

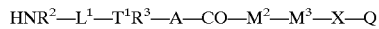
$HNR^2—L^1—T^1R^3—A—CO—M^2—M^3—X—Q$

The reaction is conveniently performed in a suitable inert solvent or diluent as defined hereinbefore and at a temperature in the range, for example, 0° to 150° C., conveniently in the range 15° to 100° C.

(g) For the production of those compounds of the formula I wherein $M^2$, $M^3$ or Q bears a carboxy or carboxy-containing group, the hydrolysis of a compound of the formula I wherein $M^2$, $M^3$ or Q bears a (1–4C)alkoxycarbonyl group.

The hydrolysis reaction may conveniently be carried out in a conventional manner using, for example acidic or basic catalysis. A suitable acid for the acidic hydrolysis of an ester group is, for example, an inorganic acid such as hydrochloric or sulphuric acid. A suitable base for the basic hydrolysis of an ester group is, for example, an alkali or alkaline earth metal hydroxide such as sodium hydroxide or potassium hydroxide.

The reaction is conveniently performed in a suitable solvent or diluent such as an alcohol, for example methanol or ethanol, and at a temperature in the range, for example, 0° to 120° C., conveniently in the range of 15° to 60° C.

(h) For the production of those compounds of the formula I wherein $M^2$, $M^3$ or Q bears a carbamoyl, N-alkylcarbamoyl or N,N-dialkylcarbamoyl group, the reaction of a compound of the formula I wherein $M^2$, $M^3$ or Q bears a carboxy group, or a reactive derivative thereof as defined hereinbefore, with ammonia or an appropriate alkylamine or dialkylamine.

The reaction is conveniently performed in a suitable inert solvent or diluent as defined hereinbefore and at a temperature in the range, for example, 0° to 120° C., conveniently in the range 15° to 60° C.

(i) For the production of those compounds of the formula I wherein Q bears a hydroxy group, the dealkylation of a compound of the formula I wherein Q bears a (1–4C)alkoxy group.

A suitable dealkylating reagent is, for example, any of the many reagents known to effect such a transformation. The reaction may be carried out, for example, using an alkali metal (1–4C)alkylsulphide such as sodium ethanethiolate or, for example, using an alkali metal diarylphosphide such as lithium diphenylphosphide. Alternatively the reaction may conveniently be carried out using a boron or aluminium trihalide such as boron tribromide.

The dealkylation reaction is conveniently performed in a suitable inert solvent or diluent as defined hereinbefore and at a temperature in the range, for example, −80° to 100° C., conveniently in the range 0° to 50° C.

When a pharmaceutically-acceptable salt of a compound of the formula I is required, it may be obtained, for example, by reaction of said compound with a suitable acid or base using a conventional procedure.

When an optically active form of a compound of the formula I is required, it may be obtained, for example, by carrying out one of the aforesaid procedures using an optically active starting material or by resolution of a racemic form of said compound using a conventional procedure.

As stated previously, the compounds of the formula I and of the formula Ia are inhibitors of the enzyme Factor Xa. The effects of this inhibition may be demonstrated using one or more of the standard procedures set out hereinafter:

a) Measurement of Factor Xa Inhibition

An in vitro assay system was carried out based on the method of Kettner et al., *J. Biol. Chem.*, 1990, 265, 18289–18297, whereby various concentrations of a test compound were dissolved in a pH 7.5 buffer containing 0.5% of polyethylene glycol and incubated at 37° C. with human Factor Xa (0.001 Units/ml, 0.3 ml) for 15 minutes. The chromogenic substrate S-2765 (KabiVitum AB, 20 μM) was added and the mixture was incubated at 37° C. for 20 minutes whilst the absorbance at 405 nm was measured. The maximum reaction velocity (Vmax) was determined and compared with that of a control sample containing no test compound. Inhibitor potency was expressed as an $IC_{50}$ value.

b) Measurement of Thrombin Inhibition

The procedure of method a) was repeated except that human thrombin (0.005 Units/ml) and the chromogenic substrate S-2238 (YabiVitum AB) were employed.

c) Measurement of Anticoagulant Activity

An in vitro assay whereby human venous blood was collected and added directly to a sodium citrate solution (3.2 g/100 ml, 9 parts blood to 1 part citrate solution). Blood plasma was prepared by contrifugation (1000 g, 15 minutes) and stored at 2–4° C. Conventional activated partial thromboplastin time (APTT) and prothrombin time (PT) tests were carried out in the presence of various concentrations of a test compound and the concentration of test compound required to double the clotting time, hereinafter referred to as CT2, was determined. In the APTT test, the test compound, blood plasma and APTT reagent were incubated at 37° C. for 3 minutes. Calcium chloride (0.02 M) was added and fibrin formation and the time required for a clot to form were determined. In the PT test, an analogous procedure was followed except that tissue thromboplastin was used in place of APTT reagent.

d) An ex vivo Assay of Anticoagulant Activity

The test compound was administered intravenously or orally to a group of Alderley Park Vistar rats. At various times thereafter animals were anaesthetised, blood was collected and APTT and PT coagulation assays analogous to those described hereinbefore were conducted.

e) An in vivo Measurement of Antithrombotic Activity

Thrombus formation was induced using an analogous method to that described by Vogel et al., *Thromb. Research*, 1989, 54, 399–410. A group of Alderley Park Mistar rats was anaesthetised and surgery was performed to expose the vena cava. Two loose sutures were located, 0.7 cm apart, round the inferior vena cava. Test compound was administered intravenously or orally. At an appropriate time thereafter tissue thromboplastin (1 ml/kg) was administered into the jugular vein and, after 10 seconds, the two sutures were tightened to induce stasis within the ligated portion of vena cava. After 10 minutes the ligated tissue was excised and the thrombus therein was isolated, blotted and weighed.

Although the pharmacological potencies of the compounds of formulae I and Ia vary with structural changes as expected, in general compounds of the formulae I and Ia possess activity at the following concentrations or doses in at least one of the above tests a) to c):

test a): $IC_{50}$ (Factor Xa) in the range, for example, 0.001–25 pH;

test b): $IC_{50}$ (thrombin), for example, greater than 50 μH;

test c): CT2 (PT) in the range, for example, 1–50 μM; CT2 (APTT) in the range, for example, 10–100 μM.

By way of example, the compound of Example 1 as disclosed hereinafter has an $IC_{50}$ of 0.3 pH against Factor Xa in test a), an $IC_{50}$ of greater than 100 μM against thrombin in test b) and a CT2 (PT) of 14 μM and CT2 (APTT) of 62 μM in test c), and shows an increased clotting time following the intravenous administration of a 10 mg/kg dose in test d) and a reduced thrombus weight following the intravenous administration of a 5 mg/kg dose in test e).

By way of further example, the compound of Example 39, Compound No. 2, as disclosed hereinafter has an $IC_{50}$ of 0.012 µM against Factor Xa in test a), an $IC_{50}$ of greater than 100 µM against thrombin in test b), a CT2 (PT) of 1 µM and CT2 (APTT) of 1.8 µM in test c), and shows an increased clotting time following the intravenous administration of a 5 mg/kg dose in test d) and a reduced thrombus weight following the intravenous administration of a 5 mg/kg dose in test d).

By way of further example, the compound of Example 41, Compound No. 3, as disclosed hereinafter has an $IC_{50}$ of 0.01 µM against Factor Xa in test a) and an $IC_{50}$ of 83 µM against thrombin in test b).

By way of further example, the compound of Example 40, Compound No. 5, as disclosed hereinafter has an $IC_{50}$ of 0.003 µM against Factor Xa in test a), an $IC_{50}$ of 34 µM against thrombin in test b), a CT2 (PT) of 0.5 µM and CT2 (APTT) of 1.2 µM in test c), and shows an increased clotting time following the intravenous administration of a 5 mg/kg dose in test d).

By way of further example, the compound of Example 62 as disclosed hereinafter has an $IC_{50}$ of 0.002 µM against Factor Xa in test a), an $IC_{50}$ of >10 µM against thrombin in test b), a CT2 (PT) of 0.7 µM in test c), and shows an increased clotting time following the intravenous administration of a 5 mg/kg dose in test d).

By way of further example, the compound of Example 63 as disclosed hereinafter has an $IC_{50}$ of 0.008 µM against Factor Xa in test a), an $IC_{50}$ of >10 µM against thrombin in test b), a CT2 (PT) of 4.6 µM in test c), and shows an increased clotting time following the intravenous administration of a 5 mg/kg dose in test d) and a reduced thrombus weight following the intravenous administration of a 5 mg/kg dose in test e).

According to a further feature of the invention there is provided a pharmaceutical composition which comprises an aminoheterocyclic derivative of the formula I or of the formula Ia, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an aminoheterocyclic derivative of the formulae I or Ia, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an aminoheterocyclic derivative of the formula I or of the formula Ia, or a pharmaceutically-acceptable salt thereof, for use in a method of treatment of the human or animal body by therapy.

The invention also includes the use of such an active ingredient in the production of a medicament for use in:
(i) producing a Factor Xa inhibitory effect;
(ii) producing an anticoagulant effect;
(iii) producing an antithrombotic effect;
(iv) treating a Factor Xa mediated disease or medical condition;
(v) treating a thrombosis mediated disease or medical condition;
(vi) treating coagulation disorders; and/or
(vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of the formulae I or Ia will naturally vary according to the nature and severity of the medical condition, the age and sex of the animal or patient being treated and the route of administration, according to well known principles of medicine. As mentioned above, compounds of the formulae I or Ia are useful in the treatment or prevention of a variety of medical disorders where anticoagulant therapy is indicated. In using a compound of the formula I for such a purpose, it will generally be administered so that a daily dose in the range, for example, 0.5 to 500 mg/kg body weight is received, given if required in divided doses. In general lower doses will be administered when a parenteral route is employed, for example a dose for intravenous administration in the range, for example, 0.5 to 50 mg/kg body weight will generally be used. For preferred and especially preferred compounds of the invention, in general, lower doses will be employed, for example a daily dose in the range, for example, 0.5 to 10 mg/kg body weight.

Although the compounds of the formulae I and Ia are primarily of value as therapeutic or prophylactic agents for use in warm-blooded animals including man, they are also useful whenever it is required to produce an anticoagulant effect, for example during the ex-vivo storage of whole blood or in the development of biological tests for compounds having anticoagulant properties.

The compounds of the invention may be administered as a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known antihypertensive agent.

The invention will now be illustrated in the following Examples in which, unless otherwise stated:
(i) evaporations were carried out by rotary evaporation in vacuo and work-up procedures were carried out after removal of residual solids by filtration;
(ii) operations were carried out at room temperature, that is in the range 18–25° C. and under an atmosphere of an inert gas such as argon;
(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) the end-products of the formula I have satisfactory microanalyses and their structures were confirmed by nuclear magnetic resonance (NMR) and mass spectral techniques; unless otherwise stated, $CDCl_3$ solutions of the end-products of the formula I were used for the determination of NMR spectral data, chemical shift values were measured on the delta scale; the following abbreviations have been used: s, singlet; d, doublet; t, triplet; m, multiplet;

(vi) intermediates were not generally fully characterised and purity was assessed by thin layer chromatographic, infra-red (IR) or NMR analysis;

(vii) melting points were determined using a Hettler SP62 automatic melting point apparatus or an oil-bath apparatus; melting points for the end-products of the formula I were generally determined after crystallisation from a conventional organic solvent such as ethanol, methanol, acetone, ether or hexane, alone or in admixture; and (viii) the following abbreviations have been used:

| | |
|---|---|
| DMF | N,N-dimethylformamide; |
| THF | tetrahydrofuran; |
| DMSO | dimethylsulphoxide; |
| DMPU | 1,3-dimethyl-3,4,5,6-tetrahydro-2(1H)-pyrimidinone. |

EXAMPLE 1

N-[2-Amino-1-(piperidinocarbonyl)ethyl]-2-(2-naphthalene-sulphonamido)acetamide hydrochloride salt (2.6 g) and triethylamine (3.18 ml) were added in turn to a stirred solution of 1-(4-pyridyl)piperidine-4-carbonyl chloride (1.54 g) in methylene chloride (20 ml) and the mixture was stirred at ambient temperature for 16 hours. The mixture was partitioned between ethyl acetate and water. The organic phase was washed with water, dried ($MgSO_4$) and evaporated. The residue was purified by column chromatography using a 89:10:1 mixture of ethyl acetate, methanol and ammonia as eluent. The material so obtained was triturated under diethyl ether to give 2-(2-naphthalenesulphonamido)-N-{1-piperidinocarbonyl-2-[1-(4-pyridyl)-piperidin-4-ylcarbonylamino]ethyl}acetamide as a foam (1.9 g, 55%);

NMR Spectrum ($CD_3SOCD_3$) 1.37–1.76 (m, 10 H), 3.15–3.5 (m, 10 H), 3.6 (s, 2 H), 4.1–4.2 (d, 2 H), 4.9 (t, 1 H), 7.1 (d, 2 H), 7.6–8.2 (m, 10 H), 8.4 (S, 1 H);

Elemental Analysis

Found C, 60.7; H, 6.5; N, 13.2; $C_{31}H_{38}N_6O_5S$ 0.5 $H_2O$ requires C, 60.5; H, 6.3; N, 13.6%.

The N-[2-amino-1-(piperidinocarbonyl)ethyl]-2-(2-naphthalene-sulphonamido)acetamide used as a starting material was obtained as follows:

N-Hydroxybenzotriazole (10.16 g) and N-(3-dimethylaminopropyl)-N'-ethylcarbodiimide (14.7 g) were added in turn to a stirred solution of $N^2$-benzyloxycarbonyl-DL-asparagine (20 g) in DHF (200 ml) which had been cooled in an ice-bath. The mixture was stirred at 0° to 5° C. for 1 hour. Piperidine (7.4 ml) was added and the mixture was stirred for 16 hours and allowed to warm to ambient temperature. The mixture was concentrated by evaporation. Water (500 ml) was added and the precipitate was isolated and dried. There was thus obtained $N^2$-benzyloxycarbonyl-DL-asparagine piperidide (12 g), m.p. 159–162° C.

After repetition of the reaction, the piperidide so obtained (17 g) was added to a stirred solution of bis (trifluoroacetoxy)iodobenzene (33 g) in a mixture of DHF (100 ml) and water (100 ml). The mixture was stirred at ambient temperature for 20 minutes. Triethylamine (14.2 ml) was added and the mixture was stirred for 16 hours. The mixture was acidified by the addition of 2 N aqueous hydrochloric acid and extracted with ethyl acetate. The aqueous phase was basified to pH 8 by the addition of 2 N aqueous sodium hydroxide solution and extracted with ethyl acetate (3×60 ml). The extracts were combined, washed with water, dried ($MgSO_4$) and evaporated. There was thus obtained 1-[3-amino-2-(benzyloxycarbonylamino) propionyl]piperidine as an oil (8.12 g).

Di-tert-butyl dicarbonate (8.75 g) and triethylamine (7.1 ml) were added in turn to a stirred solution of the piperidine so obtained in methylene chloride (150 ml) and the mixture was stirred at ambient temperature for 16 hours. The mixture was-partitioned between methylene chloride and IN aqueous citric acid solution. The organic phase was washed with water, dried ($MgSO_4$) and evaporated. The residue was purified by column chromatography using a 1:1 mixture of hexane and ethyl acetate as eluent. There was thus obtained 1- [2-(benzyloxycarbonylamino)-3-(tert-butoxycarbonylamino)propionyl]-piperidine as an oil (7.98 g).

A mixture of a portion (4.2 g) of the material so obtained, 10% palladium-on-carbon catalyst (0.3 g) and ethanol (100 ml) was stirred under an atmosphere of hydrogen for 8 hours. The mixture was filtered and the filtrate was evaporated. The residue was triturated under diethyl ether to give 1-[2-amino-3-(tert-butoxycarbonylamino)-propionyl] piperidine (2.3 g), m.p. 87–90° C.

A solution of N-(2-naphthylsulphonyl)glycine (2.93 g)min DMF (20 ml) was added to a stirred mixture of H-hydroxybenzotriazole (1.5 g), N-(3-dimethylaminopropyl)-N-ethylcarbodiimide (2.16 g) and DMF (80 ml) which had been cooled in an ice-bath. The mixture was stirred for 1 hour. A solution of 1-[2-amino-3-(tert-butoxycarbonylamino)-propionyl]piperidine (2.98 g) in DMF (10 ml) was added and the mixture was allowed to warm to ambient temperature and stirred for 16 hours. The mixture was partitioned between methylene chloride and water. The organic phase was washed with water, dried ($MgSO_4$) and evaporated. The residue was purified by column chromatography using ethyl acetate as eluent. There was thus obtained N-[2-(tert-butoxycarbonylamino)-1-(piperidinocarbonyl)ethyl]-2-(2-naphthalenesulphonamido) acetamide (3.2 g), m.p. 95–98° C.

A portion (0.5 g) of the material so obtained was suspended in ethyl acetate (25 ml) and the mixture was cooled in an ice-bath. Hydrogen chloride gas was led into the reaction mixture for 20 minutes. A clear solution was formed followed by the deposition of a precipitate. The solid was isolated and dried. There was thus obtained N-[2-amino-1-(piperidinocarbonyl)ethyl]-2-(2-naphthalene-sulphonamido)acetamide hydrochloride salt (0.34 g);

NMR Spectrum ($CD_3SOCD_3+CD_3CO_2D$) 1.2–1.6 (m, 6 H), 2.7–3.1 (a, 2 H), 3.1–3.25 (t, 2 H), 3.3–3.5 (m, 2 H), 3.6 (s, 2 H), 4.8–5.0 (t, 1 H), 6.5–8.1 (m, 7 H), 8.4 (s, 1 H);

Elemental Analysis

Found C, 50.9; H, 6.3; N, 11.8; $C_{20}H_{26}N_4O_4S$ HCl $H_2O$ requires C, 50.7; H, 6.1; N, 11.8%.

The 1-(4-pyridyl)piperidine-4-carbonyl chloride used as a starting material was obtained as follows:

Oxalyl chloride (0.14 ml) and DHF (2 drops) were added in turn to a stirred solution of 1-(4-pyridyl)piperidine-4-carboxylic acid [*Tetrahedron*, 1988, 44, 7095; 0.21 g] in methylene chloride (20 ml). The mixture was stirred at ambient temperature for 4 hours. The mixture was evaporated and there was thus obtained the required starting material which was used without further purification.

EXAMPLE 2

A solution of 2-naphthylsulphonyl chloride (0.55 g) in methylene chloride (10 ml) was added to a stirred mixture of 1-[1-(4-pyridyl)piperidin-4-ylcarbonyl]piperazine trihydrochloride salt (0.85 g), triethylamine (3.1 ml) and methylene chloride (80 ml) and the resultant mixture was stirred at ambient temperature for 18 hours. The mixture was partitioned between methylene chloride and water. The organic phase was washed with water, dried ($NgSO_4$) and evaporated. The residue was purified by column chromatography using increasingly polar mixtures of methylene chloride and methanol (100:6 to 100:10) as eluent. There was thus obtained 1-(2-naphthylsulphonyl)-4-[1-(4-pyridyl) piperidin-4-ylcarbonyl]piperazine as a solid (0.727 g);

NMR Spectrum ($CD_3SOCD_3$) 1.4–1.65 (m, 4 H), 2.75–3.05 (m, 7 H), 3.5–3.7 (m, 4 H), 3.8–3.95 (m, 2 H), 6.8 (d, 2 H), 7.65–7.8 (m, 3 H), 8.05–8.25 (m, 5 H), 8.45 (d, 1 H);

Elemental Analysis

Found C, 63.4; H, 6.1; N, 11.5; $C_{25}H_{28}N_4O_3S$ 0.5 $H_2O$ requires C, 63.4; H, 6.1; N, 11.8%.

The 1-[1-(4-pyridyl)piperidin-4-ylcarbonyl]piperazine used as a starting material was obtained as follows:

Thionyl chloride (1.6 ml) was added dropwise to a stirred suspension of 1-(4-pyridyl)piperidine-4-carboxylic acid (2.17 g) in methylene chloride (30 ml) and the mixture was stirred at ambient temperature for 1 hour. The mixture was evaporated to give 1-(4-pyridyl)piperidine-4-carbonyl chloride which was used without further purification.

The material so obtained was suspended in methylene chloride (30 ml) and triethylamine (7.8 ml) and a solution of 1-tert-butoxycarbonylpiperazine (2.08 g) in methylene chloride (10 ml) were added in turn. The mixture was stirred at ambient temperature for 4 hours. The mixture was partitioned between methylene chloride and water. The organic phase was washed with water, dried ($MgSO_4$) and evaporated. The residue was purified by column chromatography using increasingly polar mixtures of methylene chloride and methanol as eluent (100:5 to 100:13). There was thus obtained 1-(tert-butoxycarbonyl)-4-[1-(4-pyridyl)piperidin-4-ylcarbonyl]-piperazine (2.38 g).

A saturated solution of hydrogen chloride in diethyl ether (25 ml) was added to a stirred solution of the 1-tert-butoxycarbonylpiperazine so obtained in methylene chloride (120 ml) and the mixture was stirred at ambient temperature for 18 hours. The mixture was evaporated and the residue was triturated under diethyl ether. There was thus obtained 1-[1-(4-pyridyl)piperidin-4-ylcarbonyl]piperazine trihydrochloride salt (2.85 g);

NMR Spectrum ($CD_3SOCD_3$) 1.5–1.9 (m, 4 H), 3.0–3.2 (m, 7 H), 3.6–3.85 (m, 4 H), 4.15–4.3 (m, 2 H), 7.2 (d, 2 H), 8.2 (d, 2 H).

EXAMPLE 3

1,1'-Carbonyldiimidazole (0.089 g) and triethylamine (0.08 ml) were added in turn to a solution of N-[2-amino-1-(piperidino-carbonyl)ethyl-]-2-(2-naphthalenesulphonamido)acetamido hydrochloride salt (0.25 g) in DMF (15 ml) which had been cooled in an ice-bath. The mixture was stirred for 30 minutes. 1-(4-Pyridyl)piperazine (0.089 g) was added and the mixture was stirred at ambient temperature for 16 hours. The mixture was partitioned between ethyl acetate and water. The organic phase was washed with water, dried ($MGgSO_4$) and evaporated. The residue was purified by column chromatography using ethyl acetate as eluent. There-was thus obtained 2-(2-naphthalenesulphonamido)-N-{1-piperidinocarbonyl-2-[4-(4-pyridyl)piperazin-1-ylcarbonylamino]-ethyl}acetamide as a foam (0.118 g);

NMR Spectrum ($CD_3SOCD_3+CD_3CO_2D$) 1.3–1.6 (m, 6 H), 3.0–3.1 (m, 1 H), 3.2–3.6 (m, 15 H), 4.8–4.9 (m, 1 H), 7.0 (d, 2 H), 7.5–7.7 (m, 2 H), 7.75–7.83 (m, 1 H), 7.9–8.1 (m, 3 H), 8.1–8.2 (d, 2 H), 8.4 (s, 1 H);

Elemental Analysis

Found C, 58.9; H, 6.4; N, 15.3; $C_{30}H_{37}N_7O_5S$ 0.25 EtAc requires C, 59.1; H, 6.2; N, 15.6%.

EXAMPLE 4

Using an analogous procedure to that described in Example 1 except that 2-[1-(4-pyridyl)piperidin-4-yl]acetyl chloride hydrochloride salt was used in place of 1-(4-pyridyl)piperidine-4-carbonyl chloride and that the product was purified by high pressure liquid chromatography using a 50:50:0.1 mixture of acetonitrile, water and trifluoroacetic acid as eluent. There was thus obtained 2-(2-naphthalenesulphonamido)-N-(1-piperidinocarbonyl-2-{2-[1-(4-pyridyl)piperidin-4-yl]acetamido}ethyl)acetamide as a foam in 18% yield;

NPR Spectrum ($CD_3SOCD_3+CD_3CO_2D$) 1.0–1.7 (m, 6 H), 1.7–2.1 (m, 8 H), 3.0–3.4 (m, 9 H), 3.5–3.6 (s, 2 H), 4.1–4.2 (d, 2 H), 4.8–4.9 (m, 1 H), 7.05–7.2 (d, 2 H), 7.6–8.2 (m, 8 H), 8.4–8.5 (s, 1 H);

Elemental Analysis

Found C, 52.8; H, 5.4; N, 11.4; $C_{32}H_{40}N_6O_5S$ $CF_3CO_2H$ $H_2O$ requires C, 53.0; H, 5.8; N, 10.9%.

The 2-[1-(4-pyridyl)piperidin-4-yl]acetyl chloride hydrochloride salt used as a starting material was obtained as follows:

Triethyl phosphonoacetate (19.8 ml) was added dropwise to a stirred suspension of sodium hydride (50% dispersion in mineral oil, 4.8 g) in dimethoxyethane (300 ml) which had been cooled in an ice-bath and the mixture was stirred at 0° to 5° C. for 1 hour. 1-Benzyl-4-piperidone (17.85 ml) was added dropwise and the mixture was stirred at ambient temperature for 16 hours. The mixture was partitioned between diethyl ether and water. The organic phase was washed with water and with brine, dried ($MgSO_4$) and evaporated. The residue was purified by column chromatography using a 3:2 mixture of hexane and ethyl acetate. There was thus obtained 1-benzyl-4-(ethoxycarbonylmethylene)piperidine (5.52 g).

A mixture of the material so obtained, 10% palladium-on-carbon catalyst (1 g) and ethanol (250 ml) was stirred under an atmosphere of hydrogen for 6 hours. The mixture was filtered to give ethyl 2-(piperidin-4-yl)acetate as an oil (3.31 g) which was used without further purification;

NMR Spectrum (CDCl$_3$) 1.0–1.2 (m, 2 H), 1.25 (t, 3 H), 1.7 (s, 2 H), 1.9 (m, 1 H), 2.2 (d, 2 H), 2.6 (m, 2 H), 3.05 (m, 2 H), 4.0 (m, 2 H).

A mixture of a portion (3.25 g) of the material so obtained, 4-chloropyridine hydrochloride (2.85 g), triethylamine (5.28 ml) and xylene (100 ml) was stirred and heated to reflux for 16 hours. The mixture was cooled to ambient temperature and filtered. The filtrate was evaporated and the residue was partitioned between methylene chloride and water. The organic phase was washed with water, dried (MgSO$_4$) and evaporated. The residue was purified by column chromatography using a 10:1 mixture of methylene chloride and methanol as eluent. There was thus obtained ethyl 2-[1-(4-pyridyl)piperidin-4-yl]acetate as an oil (2.15 g).

A mixture of the material so obtained, 1N aqueous hydrochloric acid (35.5 ml) and dioxan (100 ml) was stirred and heated to 95° C. for 3 hours. The mixture was evaporated and the residue was freeze-dried to give 2-[1-(4-pyridyl) piperidin-4-yl]acetic acid hydrochloride salt (2.3 g), m.p. 105–108° C.

Using an analogous procedure to that described in the portion of Example 1 which is concerned with the preparation of starting materials, the acetic acid was reacted with oxalyl chloride to give 2-[1-(4-pyridyl)piperidin-4-yl]acetyl chloride hydrochloride salt in quantitative yield.

EXAMPLE 5

Using an analogous procedure to that described in Example 1 except that 2-[4-(4-pyridyl)piperazin-1-yl]acetyl chloride was used in place of 1-(4-pyridyl)piperidine-4-carbonyl chloride. There was thus obtained 2-(2-naphthalenesulphonamido)-N-(1-piperidinocarbonyl-2-{2-[4-(4-pyridyl)piperazin-1-yl]acetamido}ethyl)acetamide as a foam in 6% yield;

NMR Spectrum (CD$_3$SOCD$_3$) 1.3–1.6 (m, 6 H), 2.9–3.05 (s, 2 H), 3.1–3.7 (m, 14 H), 4.8–5.0 (t, 1 H), 7.0–7.2 (d, 2 H), 7.6–8.2 (m, 9 H), 8.4 (s, 1 H);

Elemental Analysis

Found C, 57.4; H, 6.2; N, 14.5; C$_{31}$H$_{39}$N$_7$O$_5$S 1.5 H$_2$O requires C, 57.4; H, 6.5; N, 15.1%.

The 2-[4-(4-pyridyl)piperazin-1-yl]acetyl chloride used as a starting material was obtained as follows:

Sodium hydride (50% dispersion in mineral oil, 1.9 g) was added portionwise to a stirred mixture of 1-(4-pyridyl) piperazine (3 g) and DMF (20 ml) and the mixture was stirred at ambient temperature for 1 hour. Tert-butyl bromoacetate (6.5 ml) was added dropwise and the mixture was stirred for 18 hours. The mixture was partitioned between ethyl acetate and water. The organic phase was washed with water, dried (MgSO$_4$) and evaporated. The residue was purified by column chromatography using a 17:3 mixture of methylene chloride and methanol as eluent. There was thus obtained tert-butyl 2-[4-(4-pyridyl)piperazin-1-yl]acetate as a solid (2.85 g).

A mixture of the material so obtained and trifluoroacetic acid (7 ml) was stirred at ambient temperature for 18 hours. The mixture was evaporated to give 2-[4-(4-pyridyl) piperazin-1-yl]acetic acid in quantitative yield;

NMR Spectrum (CD$_3$SOCD$_3$) 3.35–3.5 (m, 4 H), 3.9–4.05 (m, 4 H), 4.1 (s, 2 H), 7.25 (d, 2 H), 8.35 (d, 2 H).

A mixture of the material so obtained (2.27 g), oxalyl chloride (1.5 ml), DMF (3 drops) and methylene chloride (20 ml) was stirred at ambient temperature for 4 hours. The mixture was evaporated to give 2-[4-(4-pyridyl)piperazin-1-yl]acetyl chloride which was used without further purification.

EXAMPLE 6

Triethylamine (0.77 ml) was added to a stirred mixture of ethyl 2-amino-3-[1-(4-pyridyl)piperidin-4-ylcarbonylamino]propionate dihydrochloride salt (1 g), succinimido 2-(2-naphthalenesulphonamido)-acetate (0.92 g) and methylene chloride (50 ml) which had been cooled in an ice-bath. The mixture was allowed to warm to ambient temperature and was stirred for 4 hours. The mixture was partitioned between methylene chloride and water. The organic phase was washed with water, dried (MgSO$_4$) and evaporated. The residue was purified by column chromatography using a 4:1 mixture of ethyl acetate and methanol as eluent. There was thus obtained N-{1-ethoxycarbonyl-2-[1-(4-pyridyl)-piperidin-4-ylcarbonylamino]ethyl}-2-(2-naphthalenesulphonamido)-acetamide as a foam (0.203 g);

NMR Spectrum (CD$_3$SOCD$_3$) 1.1–1.2 (t, 3 H), 1.4–1.8 (m, 4 H), 2.2–2.4 (m, 1 H), 2.7–3.0 (t, 2 H), 3.5 (s, 2 H), 3.8–4.1 (m, 4 H), 4.2–4.4 (t, 1 H), 6.7–6.8 (d, 2 H), 7.6–8.3 (m, 11 H), 8.4 (s, 1 H);

Elemental Analysis

Found C, 55.7; H, 6.0; N, 11.1; C$_{28}$H$_3$ N$_5$O$_6$S 2 H$_2$O requires C, 55.5; H. 6.1; N, 11.6%.

The ethyl 2-amino-3-[1-(4-pyridyl)piperidin-4-ylcarbonyl-amino]propionate dihydrochloride salt used as a starting material was obtained as follows:

N$^2$-Benzyloxycarbonyl-DL-asparagine (25 g) was added to a stirred solution of bis(trifluroacetoxy)iodobenzene (60.6 g) in a mixture of DXF (350 ml) and water (350 ml). The mixture was stirred at ambient temperature for 15 minutes. Pyridine (15 ml) was added and the mixture was stirred for 16 hours. The mixture was evaporated and the residue was partitioned between water and diethyl ether. The aqueous layer was evaporated to give an oil mixed with a solid. The solid was isolated, washed with diethyl ether and dried. There was thus obtained 3-amino-2-(benzyloxycarbonylamino)propionic acid (6.3 g).

A portion (3 g) of the material so obtained was added to a stirred mixture of thionyl chloride (1.01 ml) and ethanol (100 ml) which had been cooled to −10° C. The mixture was allowed to warm to ambient temperature and was stirred for 16 hours. The mixture was evaporated and the residue was triturated under diethyl ether. There was thus obtained ethyl 3-amino-2-(benzyloxycarbonylamino)propionate hydrochloride salt (3.45 g);

NMR Spectrum (CD$_3$SOCD$_3$) 1.1–1.25 (t, 3 H), 3.0–3.2 (m, 2 H), 4.05–4.2 (q, 2 H), 4.3–4.5 (m, 1 H), 5.1 (s, 2 H), 7.3 (m, 5 H), 7.8–7.9 (d, 1 H), 8.3 (s, 2 H).

Triethylamine (0.7 ml) was added to a stirred mixture of ethyl 3-amino-2-(benzyloxycarbonylamino)propionate hydrochloride salt (0.5 g), 1-(4-pyridyl)piperidine-4-carbonyl chloride (0.45 g) and methylene chloride (20 ml) and the resultant mixture was stirred at ambient temperature for 16 hours. The mixture was partitioned between methylene chloride and water. The organic phase was washed with brine, dried (MgSO$_4$) and evaporated. The residue was purified by column chromatography using increasingly polar mixtures of ethyl acetate and methanol as eluent. There was thus obtained ethyl 2-(benzyloxycarbonylamino)-3-[1-(4-pyridyl)piperidin-4-ylcarbonyl-amino]propionate (0.5 g).

After repetition of the previous step, a mixture of the material so obtained (2 g), 10% palladium-on-carbon catalyst (0.2 g), 1 N aqueous hydrochloric acid (8.8 ml) and ethanol (50 ml) was stirred under an atmosphere of hydrogen for 6 hours. The mixture was filtered and the filtrate was evaporated. There was thus obtained ethyl 2-amino-3-[1-(4-pyridyl)piperidin-4-ylcarbonylamino]propionate dihydrochloride salt (2.48 g);

NMR Spectrum ($CD_3SOCD_3$) 1.2–1.3 (t, 3 H), 1.5–1.7 (m, 2 H), 1.8–2.0 (m, 2 H), 2.6–2.7 (m, 1 H), 3.2–3.4 (t, 2 H), 4.0–4.3 (m, 6 H), 7.15–7.82 (d, 2 H), 8.1–8.2 (d, 2 H), 8.5–8.65 (t, 1 H).

The succinimido 2-(2-naphthalenesulphonamido)acetate used as a starting material was obtained as follows:

A solution of N,N'-dicyclohexylcarbodiimide (4.12 g) in ethyl acetate (50 ml) was cooled to 0° C. and added to a stirred mixture of N-(2-naphthylsulphonyl)glycine (5.3 g), N-hydroxysuccinimide (2.3 g) and ethyl acetate which had been cooled to 0° C. The mixture was stirred at 0° C. for 1 hour, allowed to warm to ambient temperature and stirred for 16 hours. The mixture was recooled to 0° C. for 1 hour and filtered. The filtrate was evaporated and the residue was recrystallised from a mixture of hexane and ethyl acetate. There was thus obtained the required starting material (6.2 g);

NMR Spectrum ($CD_3SOCD_3$) 2.8 (m, 4 H), 4.25 (d, 2 H), 7.6–7.75 (m, 2 H), 7.8–7.9 (m, 1 H), 8.0–8.2 (m, 3 H), 8.45 (s, 1 H), 8.6 (t, 1 H).

EXAMPLE 7

Using an analogous procedure to that described in Example 2, 2-naphthylsulphonyl chloride was reacted with ethyl 2-amino-3-[1-(4-pyridyl)piperidin-4-ylcarbonylamino]propionate dihydrochloride salt to give ethyl 2-(2-naphthalenesulphonamido)-3-[1-(4-pyridyl) piperidin-4-ylcarbonylamino]propionate as a foam in 37% yield;

NMR Spectrum ($CD_3SOCD_3$) 1.1–1.2 (t, 3 H), 1.3–1.7 (m, 4 H), 2.1–2.3 (m, 1 H), 2.7–2.9 (m, 2 H), 3.1–3.9 (m, 6 H), 3.9–4.1 (t, 1 H), 6.7–6.8 (d, 2 H), 7.6–8.2 (m, 11 H), 8.35 (s, 1 H);

Elemental Analysis

Found C, 59.8; H, 6.4; N, 10.3; $C_{26}H_{30}N_4O_5S$ 0.75 $H_2O$ requires C, 59.6; H, 6.0; N, 10.7%.

EXAMPLE 8

A mixture of N-{1-ethoxycarbonyl-2-[1-(4-pyridyl) piperidin-4-ylcarbonylamino]ethyl}-2-(2-naphthalenesulphonamido)acetamide (0.1 g), methylamine (33% solution in ethanol, 0.2 ml) and ethanol (5 ml) was stirred at ambient temperature for 2 hours. The precipitate was isolated and purified by column chromatography using increasingly polar mixtures of ethyl acetate and methanol as eluent. There was thus obtained N-methyl-2-[2-(2-naphthalenesulphonamido)acetamido]-3-[1-(4-pyridyl) piperidin-4-ylcarbonylamino]propionamide (0.01 g);

Elemental Analysis

Found C, 57.6; H, 6.1; N, 13.9; $C_{27}H_{32}N_6O_5$ 0.5 $H_2O$ 0.5 EtOH requires C, 57.5; H, 6.1; N, 14.3%.

EXAMPLE 9

A mixture of N-{1-ethoxycarbonyl-2-[1-(4-pyridyl) piperidin-4-ylcarbonylamino]ethyl}-2-(2-naphthalenesulphonamido)acetamide (0.15 g), 0.1 N aqueous sodium hydroxide solution (5.3 ml) and methanol (3 ml) was stirred at ambient temperature for 2 hours. The basic solution was neutralised by the addition of 0.1 N aqueous hydrochloric acid (5.3 ml) and evaporated. The residue was triturated under diethyl ether. There was thus obtained 2-[2-(2-naphthalenesulphonamido)acetamido]-3-[1-(4-pyridyl)piperidin-4-ylcarbonylamino]propionic acid (0.123 g);

NMR Spectrum ($CD_3SOCD_3$) 1.4–1.65 (m, 2 H), 1.6–1.75 (m, 2 H), 2.3–2.5 (m, 1 H), 2.8–3.0 (t, 2 H), 3.25–3.4 (m, 2 H), 3.85–3.95 (d; 2 H), 4.0–4.15 (m, 1 H), 6.7–6.9 (s, 2 H), 7.6–8.4 (m, 10 H), 8.4 (s, 1 H);

Elemental Analysis

Found C, 46.7; H, 4.5; N, 10.3; $C_{26}H_{29}N_5O_6S$ 2 NaCl $H_2O$ requires C, 46.3; H, 4.6; N, 10.4%.

EXAMPLE 10

Using an analogous procedure to that described in Example 1, 1-(4-pyridyl)piperidine-4-carbonyl chloride was reacted with 1-[3-amino-2-(2-naphthalenesulphonamido) propionyl]piperidine hydrochloride salt to give N-[2-(2-naphthalenesulphonamido)-2-(piperidinocarbonyl)ethyl]-1-(4-pyridyl)-piperidine-4-carboxamide in 17% yield;

Elemental Analyis

Found C, 61.4; H, 6.8; N, 12.1; $C_{29}H_{35}N_5O_4S$ $H_2O$ requires C, 61.3; H, 6.5; N, 12.3%.

The 1-[3-amino-2-(2-naphthalenesulphonamido) propionyl] piperidine hydrochloride salt used as a starting material was obtained as follows:

Triethylamine (3.1 ml) was added to a stirred mixture of 2-naphthylsulphonyl chloride (1.67 g), 1-[2-amino-3-(tert-butoxycarbonylamino)propionyl]piperidine (2 g) and DMF (25 ml) and the mixture was stirred at ambient temperature for 16 hours. The mixture was partitioned between ethyl acetate and water. The organic phase was washed with brine, dried ($MgSO_4$) and evaporated. The residue was purified by column chromatography using increasingly polar mixtures of hexane and ethyl acetate as eluent. There was thus obtained 1-[3- (tert-butoxycarbonylamino)-2-(2-naphthalenesulphonamido)-propionyl]piperidine as a solid (2.6 g).

The compound so obtained was suspended in ethyl acetate and the mixture was cooled in an ice-bath. Hydrogen chloride gas was led into the mixture for 1 hour. A clear solution was formed followed by the deposition of a precipitate which was isolated. There was thus obtained 1-[3-amino-2-(2-naphthalenesulphonamido)propionyl]piperidine hydrochloride salt as a foam (2 g) which was used without further purification.

EXAMPLE 11

Using an analogous procedure to that described in Example 1, 1-(4-pyridyl)piperidine-4-carbonyl chloride was reacted with N-[2-amino-2-(piperidinocarbonyl)ethyl]-2-(2-naphthalenesulphonamido)-acetamide to give 2-(2-naphthalenesulphonamido)-N-{2-piperidino-carbonyl-2-[1-(4-pyridyl)piperidin-4-ylcarbonylamino]ethyl}acetamide in 41% yield, m.p. 200–202° C.;

NMR Spectrum ($CD_3SOCD_3+CD_3CO_2D$) 1.1–1.8 (m, 9 H), 3.0–3.6 (m, 12 H), 4.0–4.2 (m, 2 H), 4.8–5.0 (t, 1 H), 7.0–7.2 (s, 2 H), 7.6–7.8 (m, 2 H), 7.8–7.9 (m, 1 H), 8.0–8.3 (m, 5 H), 8.4–8.5 (s, 1 H);

Elemental Analysis

Found C, 61.1; H, 6.4; N, 13.7; $C_{31}H_{38}N_6O_5S$ requires C, 61.4; H, 6.3; N, 13.9%.

The N-[2-amino-2-(piperidinocarbonyl)ethyl]-2-(2-naphthalene-sulphonamido)acetamide used as a starting material was obtained as follows:

A mixture of 1-[3-amino-2-(benzyloxycarbonylamino) propionyl]-piperidine (2 g), succinimido 2-(2-naphthalenesulphonamido)acetate (2.4 g) and ethyl acetate (25 ml) was stirred at ambient temperature for 12 hours. The mixture was partitioned between ethyl acetate and water. The organic phase was washed with water, dried ($MgSO_4$) and evaporated. The residue was purified by column chromatography using ethyl acetate as eluent. There was thus obtained N-[2-(benzyloxy-carbonylamino)-2-(piperidinocarbonyl)ethyl]-2-(2-naphthalene-sulphonamido)acetamide as a foam (1.83 g).

A mixture of the material so obtained, 10% palladium-on-carbon catalyst (0.3 g) and ethanol (40 ml) was stirred under an atmosphere of hydrogen for 8 hours. The mixture was filtered and the filtrate was evaporated. The residue was purified by column chromatography using a 1:1 mixture of hexane and ethyl acetate as eluent. There was thus obtained N-[2-amino-2-(piperidinocarbonyl)-ethyl]-2-(2-naphthalenesulphonamido)acetamide (0.52 g) which was used without further purification.

EXAMPLE 12

The procedure described in Example 2 was repeated except that 1-naphthylsulphonyl chloride was used in place of 2-naphthylsulphonyl chloride. There was thus obtained 1-(1-naphthylsulphonyl)-4-[1-(4-pyridyl)piperidin-4-ylcarbonyl]piperazine in 52% yield;

NMR Spectrum ($CD_3SOCD_3$) 1.4–1.7 (m, 4 H), 2.75–2.95 (m, 3 H), 3.0–3.2 (m, 4 H), 3.45–3.65 (m, 4 H), 3.8–3.95 (m, 2 H), 6.75 (d, 2 H), 7.6–7.8 (m, 3 H), 8.0–8.2 (m, 4 H), 8.35 (d, 1 H), 8.7 (d, 1 H);

Elemental Analysis

Found C, 62.2; H, 6.1; N, 11.3; $C_{25}H_{28}N_4O_3S$ $H_2O$ requires 62.2; H, 6.2; N, 11.6%.

EXAMPLE 13

N-Methylmorpholine (0.095 g) and isobutyl chloroformate (0.13 g) were added in turn to a stirred suspension of 1-(2-naphthylsulphonyl)piperidine-4-carboxylic acid (0.3 g) in THF (6 ml) which had been cooled to –10° C. The mixture was stirred at –10° C. for 30 minutes. A solution of 1-(4-pyridyl)piperazine (0.155 g) in DhF (3 ml) was added and the mixture was stirred at ambient temperature for 18 hours. The mixture was evaporated and the residue was purified by column chromatography using a 22:3 mixture of methylene chloride and methanol as eluent. There was thus obtained 1-[1-(2-naphthylsulphonyl)piperidin-4-ylcarbonyl]-4-(4-pyridyl)-piperazine as a solid (0.07 g);

NMR Spectrum ($CD_3SOCD_3$) 1.5–1.75 (m, 4 H), 2.3–2.45 (m, 2 H), 2.5–2.65 (m, 1 H), 3.5–3.75 (m, 10 H), 7.05 (d, 2 H), 7.6–7.75 (m, 3 H), 8.0–8.2 (m, 5 H), 8.35 (d, 1 H).

The 1-(2-naphthylsulphonyl)piperidine-4-carboxylic acid used as a starting material was obtained as follows:

A solution of ethyl piperidine-4-carboxylate (1.02 ml) in methylene chloride (5 ml) was added to a stirred mixture of 2-naphthylsulphonyl chloride (1.5 g), triethylamine (4 ml) and methylene chloride (10 ml) which had been cooled to 5° C. The mixture was stirred at ambient temperature for 18 hours. The mixture was evaporated and the residue was partitioned between ethyl acetate and water. The organic phase was washed with 2 N aqueous hydrochloric acid and water, dried ($MgSO_4$) and evaporated. There was thus obtained ethyl 1-(2-naphthylsulphonyl)piperidine-4-carboxylate (1.95 g).

A mixture of the material so obtained, potassium hydroxide (0.62 g) and ethanol (18 ml) was stirred and heated to reflux for 4 hours. The mixture was evaporated and the residue was partitioned between methylene chloride and water. The organic phase was dried ($MgSO_4$) and evaporated. There was thus obtained 1-(2-naphthylsulphonyl) piperidine-4-carboxylic acid (1.35 g);

NMR Spectrum ($CD_3SOCD_3$) 1.5–1.7 (m, 2 H), 1.8–1.95 (m, 2 H), 2.2–2.3 (m, 1 H), 2.45–2.55 (m, 2 H), 3.5–3.6 (m, 2 H), 7.65–7.8 (m, 3 H), 8.05–8.25 (m, 3 H), 8.45 (d, 1 H).

EXAMPLE 14

N,N'-Dicyclohexylcarbodiimide (0.5 g) was added to a stirred mixture of N-(2-amino-3-phenylpropyl)-1-(4-pyridyl)piperidine-4-carboxamide (1.08 g), N-(2-naphthylsulphonyl)glycine (0.85 g) N-hydroxybenzotriazole (0.34 g), N-methylmorpholine (0.71 ml) and DHF (20 ml) which had been cooled to 5° C. The mixture was stirred at ambient temperature for 18 hours. The mixture was evaporated and the residue was purified by column chromatography using increasingly polar mixtures of methylene chloride and methanol (20:1 to 20:3) as eluent. There was thus obtained 2-(2-naphthalenesulphonamido)-N-{1-phenyl-3-[1-(4-pyridyl)piperidin-4-ylcarbonylamino] prop-2-yl}acetamide as a solid (0.52 g);

NMR Spectrum ($CD_3SOCD_3$) 1.5–1.7 (m, 2 H), 1.75–1.9 (m, 2 H), 2.4–2.65 (m, 4 H), 2.9–3.4 (m, 6 H), 3.85–4.0 (m, 1 H), 4.0–4.15 (m, 2 H), 7.0–7.2 (m, 6 H), 7.55–7.65 (m, 3 H), 7.75 (m, 1 H), 7.9–8.1 (m, 5 H), 8.35 (d, 1 H).

The N-(2-amino-3-phenylpropyl)-1-(4-pyridyl) piperidine-4-carboxamide used as a starting material was obtained as follows:

Using an analogous procedure to that described in *J. Chem. Res.* (S), 1992, 391, $N^2$-tert-butoxycarbonyl-DL-phenylalanine was converted in four steps into 1-amino-2-(tert-butoxycarbonylamino)-3-phenylpropane.

Using an analogous procedure to that described in the second paragraph of the portion of Example 2 which is concerned with the preparation of starting materials, 1-(4-pyridyl)piperidine-4-carbonyl chloride was reacted with 1-amino-2-(tert-butoxycarbonylamino)-3-phenylpropane to give N-[2-(tert-butoxycarbonylamino)-3-phenylpropyl]-1-(4-pyridyl)piperidine-4-carboxamide in 39% yield.

A mixture of the material so obtained (0.95 g) and trifluoroacetic acid (2 ml) was stirred at ambient temperature for 18 hours. The mixture was evaporated and the residue was triturated under diethyl ether. There was thus obtained N-(2-amino-3-phenylpropyl)-1-(4-pyridyl)piperidine-4-carboxamide (0.9 g) which was used without further purification;

NMR Spectrum ($CD_3SOCD_3$) 1.5–1.7 (m, 2 H), 1.85–2.0 (m, 2 H), 2.75–3.0 (m, 2 H), 3.1–3.5 (m, 6 H), 4.15–4.3 (m, 2 H), 7.15–7.4 (m, 7 H), 8.2–8.3 (m, 2 H).

EXAMPLE 15

Using an analogous procedure to that described in Example 2 except that DMF was used in place of methylene chloride as the reaction solvent, 1-{2-[4-(4-pyridyl)piperazin-1-yl]acetyl}piperazine was reacted with 2-naphthylsulphonyl chloride to give 1-(2-naphthylsulphonyl)-4-{2-[4-(4-pyridyl)piperazin-1-yl]acetyl}-piperazine in 22% yield;

NMR Spectrum ($CD_3SOCD_3+CD_3CO_2D$) 2.4–2.5 (m, 4 H), 2.9–3.05 (m, 4 H), 3.15 (s, 2 H), 3.3–3.45 (m, 4 H), 3.45–3.65 (m, 4 H), 6.95 (d, 2 H), 7.5–7.75 (m, 3 H), 7.95–8.2 (m, 5 H), 8.4 (s, 1 H);

Elemental Analysis

Found C, 62.1; H, 6.1; N, 14.4; $C_{25}H_{29}N_5O_3S$ requires C, 62.6; H, 6.1; N, 14.6%.

The 1-{2-[4-(4-pyridyl)piperazin-1-yl]acetyl}piperazine used as a starting material was obtained as follows:

N,N'-Dicyclohexylcarbodiimide (0.84 g) was added to a stirred mixture of 2-[4-(4-pyridyl)piperazin-1-yl]acetic acid (1 g), 1-(tert-butoxycarbonyl)piperazine (0.67 g), N-hydroxybenzotriazole (0.382 g), N-methylmorpholine (0.79 ml) and DMF (30 ml) which had been cooled to 5° C. The mixture was stirred at ambient temperature for 18 hours. The mixture was evaporated and the residue was purified by column chromatography using a 17:3 mixture of methylene chloride and methanol as eluent. There was thus obtained 1-(tert-butoxycarbonyl)-4-{2-[4-(4-pyridyl)piperazin-1-yl]acetyl}piperazine as a foam (0.87 g).

A mixture of a portion (0.75 g) of the material so obtained, trifluoroacetic acid (2 ml) and methylene chloride (5 ml) was stirred at ambient temperature for 4 hours. The mixture was evaporated to give 1-{2-[4-(4-pyridyl)piperazin-1-yl]acetyl}piperazine in quantitative yield;

NMR Spectrum ($CD_3SOCD_3$) 3.05–3.25 (m, 4 H), 3.55–3.7 (m, 2 H), 3.7–3.8 (m, 2 H), 3.9–4.1 (m, 4 H), 4.3 (s, 2 H), 7.3 (d, 2 H), 8.4 (d, 2 H), 9.35 (s, 2 H).

EXAMPLE 16

Using an analogous procedure to that described in Example 1, 1-(4-pyridyl)piperidine-4-carbonyl chloride was reacted with N-[3-amino-1-(piperidinocarbonyl)propyl]-2-(2-naphthalenesulphonamido)-acetamide hydrochloride salt to give 2-(2-naphthalenesulphonamido)-N-{1-piperidinocarbonyl-3-[1-(4-pyridyl)piperidin-4-ylcarbonylamino]-propyl}acetamide in 17% yield;

NMR Spectrum (CD3SOCD$_3$) 1.3–1.8 (m, 12 H), 2.3–2.5 (m, 1 H), 2.7–3.1 (m, 4 H), 3.2–3.45 (m, 4 H), 3.5–3.6 (m, 2 H), 3.8–4.0 (m, 2 H), 4.6–4.7 (m, 1 H), 6.7–6.85 (m, 2 H), 7.6–7.8 (m, 3 H), 7.8–7.9 (m, 1 H), 8.0–8.35 (m, 7 H), 8.4 (s, 1 H);

Elemental Analysis

Found C, 59.6; H, 6.6; N, 13.0; $C_{32}H_{40}N_6O_5S$ 1.25 $H_2O$ requires C, 59.8; H, 6.6; N, 13.1%.

The N-[3-amino-1-(piperidinocarbonyl)propyl]-2-(2-naphthalenesulphonamido)acetamide hydrochloride salt used as a starting material was obtained as follows:

1,1'-Carbonyldiimidazole (3.95 g) was added to a stirred solution of $N^2$-benzyloxycarbonyl-DL-glutamine (8.47 g) in DMF (60 ml) and the mixture was stirred at ambient temperature for 15 minutes. The mixture was cooled to 5° C. and piperidine (4.82 ml) was added dropwise. The mixture was allowed to warm to ambient temperature over 1 hour. The mixture was partitioned between ethyl acetate and 2 N aqueous hydrochloric acid. The organic phase was washed with water and with brine, dried ($MgSO_4$) and evaporated. The residue was purified by column chromatography using a 9:1 mixture of ethyl acetate and methanol as eluent. There was thus obtained $N^2$-benzyloxycarbonyl-DL-glutamine piperidide (4.78 g), m.p. 136–138° C.

Using analogous procedures to those described in the second, third and fourth paragraphs of the portion of Example 1 which is concerned with the preparation of starting materials, the DL-glutamine piperidide was converted into 1-[2-amino-4-(tert-butoxycarbonylamino)-butyryl]piperidine in 14% yield.

1,1'-Carbonyldiimidazole (0.31 g) was added to a stirred solution of N-(2-naphthylsulphonyl)glycine (0.446 g) in DMF (5 ml) and the mixture was stirred at ambient temperature for 30 minutes. The mixture was cooled to 5° C. and 1-[2-amino-4-(tert-butoxycarbonylamino)-butyryl]piperidine (0.546 g) was added. The mixture was stirred at ambient temperature for 6 hours. The mixture was partitioned between ethyl acetate and 1 H aqueous citric acid solution. The organic phase was washed with water and with brine, dried ($MgSO_4$) and evaporated. The residue was purified by column chromatography using a 1:1 mixture of methylene chloride and ethyl acetate as eluent. There was thus obtained N-[3-(tert-butoxycarbonylamino)-1-(piperidinocarbonyl)propyl]-2-(2-naphthalenesulphonamido)acetamide as a solid (0.607 g).

The material so obtained was suspended in ethyl acetate (50 ml) and the mixture was cooled in an ice-bath. Hydrogen chloride gas was led into the mixture for 5 minutes. A clear solution was obtained followed by the deposition of a precipitate. The mixture was evaporated to give N-[3-amino-1-(piperidinocarbonyl)propyl]-2-(2-naphthalenesulphonamido)acetamide hydrochloride salt (0.528 g) which was used without further purification.

EXAMPLE 17

N-(3-Dimethylaminopropyl)-N'-ethylcarbodiimide hydrochloride salt (0.575 g) was added to a stirred mixture of (3 S)-3-(2-naphthalenesulphonamido)-3-(piperidinocarbonyl)propionic acid (1.17 g), N-hydroxybenzotriazole (0.405 g), triethylamine (0.417 ml) and DEF (10 ml) and the mixture was stirred at ambient temperature for 30 minutes. 1-(4-Pyridyl)piperazine (0.489 g) was added and the mixture was stirred at ambient temperature for 16 hours. The mixture was partitioned between ethyl acetate and water. The organic phase was washed with water and with brine, dried ($MgSO_4$) and evaporated. The residue was purified by column chromatography using increasingly polar mixtures of methylene chloride and methanol as eluent. There was thus obtained 1-[(3 S)-3-(2-naphthalenesulphonamido)-3-(piperidinocarbonyl)-propionyl]-4-(4-pyridyl)piperazine as a solid (0.407 g);

NMR Spectrum ($CDCl_3$) 0.8–1.1 (m, 2 H), 1.2–1.5 (m, 4 H), 2.5–2.8 (m, 2 H), 3.0–3.2 (m, 1 H), 3.2–3.45 (m, 7 H), 3.5–3.7 (m, 3 H), 3,75–3.9 (m, 1 H), 4.6–4.7 (m, 1 H), 6.2–6.4 (m, 1 H), 6.6–6.65 (m, 2 H), 7.5–8.0 (m, 6 H), 8.3–8.4 (m, 2 H), 8.43 (m, 1 H);

Elemental Analysis

Found C, 60.0; H, 6.0; N, 12.3; $C_{28}H_{33}N_5O_4S$ 0.3 $CH_2Cl_2$ requires C, 60.4; H, 6.0; N, 12.4%.

The (3 S)-3-(2-naphthalenesulphonamido)-3-(piperidinocarbonyl)propionic acid used as a starting material was obtained as follows:

$N^2$-(tert-butoxycarbonyl)-L-aspartic acid $O^4$-benzyl ester (16.2 g) was added portionwise to a stirred mixture of 1,1'-carbonyldiimidazole (8.1 g) in DhF (100 ml). The resultant mixture was stirred at ambient temperature for 30 minutes. The mixture was cooled in an ice-bath and piperidine (6 ml) was added dropwise. The mixture was stirred and allowed to warm to ambient temperature over 3 hours. The mixture was partitioned between ethyl acetate and 2 N aqueous hydrochloric acid. The organic phase was washed with water, dried (MgSO$_4$) and evaporated. The residue was purified by column chromatography using ethyl acetate as eluent. There was thus obtained N$^2$-(tert-butoxycarbonyl)-L-aspartic 1-piperidide O$^4$-benzyl ester (17.9 g).

A portion (4.5 g) of the material so obtained was dissolved in ethyl acetate (75 ml) and the solution was cooled in an ice-bath. Hydrogen chloride gas was led into the solution for 20 minutes. The mixture was evaporated to give L-aspartic 1-piperidide O$^4$-benzyl ester hydrochloride salt (3.6 g);

NMR Spectrum (CDCl$_3$) 1.3–1.8 (m, 6 H), 3.05–3.3 (m, 2 H), 3.4–3.6 (m, 4 H), 4.9–5.0 (m, 1 H), 5.15 (s, 2 H), 7.3–7.4 (a, 5 H), 8.5–8.8 (m, 3 H).

A portion (2.63 g) of the material so obtained was reacted with 2-naphthylsulphonyl chloride (2 g) using an analogous procedure to that described in Example 2. There was thus obtained benzyl (3 S)-3-(2-naphthalenesulphonamido)-3-(piperidinocarbonyl)propionate as an oil (2.96 g, 82%).

A mixture of the material so obtained, 10% palladium-on-carbon catalyst (0.2 g) and ethanol (25 ml) was stirred under an atmosphere of hydrogen for 6 hours. The mixture was filtered and the filtrate was evaporated. There was thus obtained (3 S)-3-(2-naphthalenesulphonamido)-3-(piperidinocarbonyl)propionic acid as a foam (2.2 g, 86%);

NMR Spectrum (CDCl$_3$) 0.8–1.1 (m, 1 H), 1.1–1.5 (m, 5 H), 2.4–2.7 (m, 2 H), 3.0–3.4 (m, 4 H), 4.7 (t, 1 H), 5.3–5.7 (m, 2 H), 7.5–7.7 (m, 2 H), 7.75–8.0 (m, 4 H), 8.45 (5, 1 H).

EXAMPLE 18

1,1'-Carbonyldiimidazole (0.307 g) was added to a solution of (3 S)-3-[2-(2-naphthalenesulphonamido)acetamido]-3-(piperidinocarbonyl)-propionic acid (0.85 g) in DMF (10 ml) and the mixture was stirred at ambient temperature for 30 minutes. 1-(4-Pyridyl)piperazine (0.309 g) was added and the mixture was stirred at ambient temperature for 16 hours. The mixture was partitioned between ethyl acetate and water. The organic phase was washed with water and with brine, dried (HgSO$_4$) and evaporated. The residue was purified by column chromatography using increasingly polar mixtures of methylene chloride and methanol as eluent. The material so obtained was recrystallised from acetonitrile. There was thus obtained 2-(2-naphthalenesulphonamido)-N-{(1 S)-1-(piperidinocarbonyl)-2-[4-(4-pyridyl)piperazin-1-ylcarbony]ethyl}-acetamide (0.201 g, 17%), m.p. 201–203° C.;

NMR Spectrum (CDCl$_3$+CD$_3$CO$_2$D) 1.2–1.6 (m, 6 H), 2.1–2.3 (m, 1 H), 2.7–2.9 (m, 1 H), 3.1–4.8 (m, 14 H), 4.9–5.0 (m, 1 H), 7.0 (d, 2 H), 7.6–7.75 (m, 2 H), 7.8–7.85 (m, 1 H), 7.9–8.15 (m, 3 H), 8.2–8.3 (m, 2 H), 8.4 (s, 1 H);

Elemental Analysis

Found C, 59.9; H, 6.2; N, 14.1; C$_{30}$H$_{36}$N$_6$O$_5$S 0.5 H$_2$O requires C, 59.9; H, 6.2; N, 14.0%.

The (3 S)-3-[2-(2-naphthalenesulphonamido)acetamido]-3-(piperidinocarbonyl)propionic acid used as a starting material was obtained as follows:

1,1'-Carbonyldiimidazole (0.81 g) was added to a stirred mixture of N-(2-naphthylsulphonyl)glycine (1.33 g) and DMF (10 ml) and the mixture was stirred at ambient temperature for 30 minutes. L-Aspartic 1-piperidide O$^4$-benzyl ester hydrochloride salt (1.63 g) and triethylamine (0.87 ml) was added in turn and the mixture was stirred at ambient temperature for 16 hours. The mixture was partitioned between ethyl acetate and water. The organic phase was washed with water and with brine, dried (MgSO$_4$) and evaporated. The residue was Apurified by column chromatography using a 3:2 mixture of methylene chloride and ethyl acetate as eluent. There was thus obtained benzyl (3 S)-3-[2-(2-naphthalenesulphonamido)acetamido]-3-(piperidinocarbonyl)-propionate as a foam (1.59 g).

A mixture of a portion (1.44 g) of the material so obtained, 10% palladium-on-carbon catalyst (0.2 g) and ethanol (30 ml) was stirred under an atmosphere of hydrogen for 6 hours. The mixture was filtered and the filtrate was evaporated. The residue was purified by column chromatography using ethyl acetate as eluent. There was thus obtained (3 S)-3-[2-(2-naphthalenesulphonamido)acetamido]-3-(piperidino-carbonyl)propionic acid as an oil (0.858 g);

NMR Spectrum (CDCl$_3$) 1.4–1.7 (m, 6 H), 2.4–2.8 (m, 2 H), 3.4–3.6 (m, 4 H), 3.6–3.8 (m, 2 H), 5.1–5.35 (m, 1 H), 6.5–6.6 (m, 2 H), 7.5–7.7 (m, 2 H), 7.8–8.0 (m, 5 H), 8.4 (s, 1 H).

EXAMPLE 19

Using an analogous procedure to that described in Example 1, 1-(4-pyridyl)piperidine-4-carbonyl chloride was reacted with 1-[-3-amino-2-(benzyloxycarbonylamino)propionyl]piperidine to give N-[2-(benzyloxycarbonylamino)-2-(piperidinocarbonyl)ethyl]-1-(4-pyridyl)piperidine-4-carboxamide in 44% yield;

NMR Spectrum 1.5–2.0 (m, 10 H), 2.2–2.4 (m, 1 H), 2.8–3.0 (m, 2 H), 3.2–3.35 (m, 1 H), 3.4–3.7 (m, 5 H), 3.8–3.95 (m, 2 H), 4.7–4.8 (m, 1 H), 5.2 (s, 2 H), 6.0–6.2 (m, 1 H), 6.2–6.4 (m, 1 H), 6.6–6.7 (m, 2 H), 7.3–7.4 (m, 5 H), 8.2–8.3 (m, 2 H);

Elemental Analysis

Found C, 63.1; H, 7.4; N, 13.3; C$_{27}$H$_{34}$N$_5$O$_4$H$_2$O requires C, 63.4; H, 7.2; N, 13.7%.

EXAMPLE 20

A mixture of 3-(2-naphthalenesulphonamido)propionic acid [prepared by the reaction of 2-naphthylsulphonyl chloride and 3-aminopropionic acid; 0.163 g], N-hydroxysuccinimide (0.067 g), N-(3-dimethylaminopropyl)-N'-ethylcarbodiimide (0.112 g) and DHF (10 ml) was stirred at ambient temperature for 30 minutes. A solution of as N-[2-amino-2-(piperidinocarbonyl)ethyl]-1-(4-pyridyl)piperidine-4-carboxamide (0.21 g) in DMF (2 ml) was added and the mixture was stirred at ambient temperature for 16 hours. The mixture was evaporated and the residue was partitioned between methylene chloride and water. The organic phase was washed with 2 N aqueous sodium hydroxide solution and with water, dried (MgSO$_4$) and evaporated. The residue was purified by column chromatography using increasingly polar mixtures of ethyl acetate and methanol as eluent. There was thus obtained 3-(2-naphthalenesulphonamido)-N-{1-(piperidinocarbonyl)-2-[1-(4-pyridyl)piperidin-4-ylcarbonylamino]ethyl}propionamide (0.14 g), m.p. 201–203° C.;

NMR Spectrum (CD$_3$SOCD$_3$) 1.2–1.6 (m, 10 H), 2.1–2.3 (m, 3 H), 2.6–2.8 (m, 2 H), 2.9 (t, 2 H), 3.0–3.1 (m, 1 H), 3.3–3.5 (m, 3 H), 3.7–3.9 (m, 2 H), 4.7–4.8 (m, 1 H), 6.6–6.7 (m, 2 H), 7.5–7.7 (m, 3 H), 7.7–7.8 (m, 2 H), 7.9–8.2 (m, 6 H), 8.35 (m, 1 H);

Elemental Analysis

Found C, 61.2; H, 6.4; N, 12.8; $C_{32}H_{40}N_6O_5S$ 0.5 EtAc requires C, 61.4; H, 6.6; N, 12.7%.

The N-[2-amino-2-(piperidinocarbonyl)ethyl]-1-(4-pyridyl)-piperidine-4-carboxamide used as a starting material was obtained as follows:

A mixture of N-[2-(benzyloxycarbonylamino)-2-(piperidinocarbonyl)ethyl]-1-(4-pyridyl)piperidine-4-carboxamide (1.37 g), 10% palladium-on-carbon catalyst (0.2 g) and ethanol was stirred under an atmosphere of hydrogen for 1 hour. The mixture was filtered and the filtrate was evaporated. There was thus obtained the required starting material in 91% yield.

EXAMPLE 21

Using an analogous procedure to that described in Example 2, N-[2-amino-2-(piperidinocarbonyl)ethyl]-1-(4-pyridyl)piperidine-4-carboxamide was reacted with naphthalene-2-carbonyl chloride to give N-{1-(piperidinocarbonyl)-2-[1-(4-pyridyl)piperidin-4-ylcarbonylamino]-ethyl}naphthalene-2-carboxamide in 85% yield;

NMR Spectrum ($CDCl_3$) 1.5–2.1 (m, 1 H), 2.3–2.4 (m, 1 H), 2.8–3.0 (m, 2 H), 3.4–4.0 (m, 8 H), 5.15–5.25 (m, 1 H), 6.6 (m, 1 H), 6.85 (m, 1 H), 7.5–7.7 (m, 2 H), 7.8–8.0 (m, 5 H), 8.2 (d, 2 H), 8.35 (s, 1 H);

Elemental Analysis

Found C, 67.6; H, 7.0; N, 13.0; $C_{30}H_{35}N_5O_3$ $H_2O$ requires C, 67.8; H, 7.0; N, 13.1%.

EXAMPLE 22

A solution of 4-tolyl isocyanate (0.133 g) in methylene chloride (5 ml) was added dropwise to a stirred solution of N-[2-amino-2-(piperidinocarbonyl)ethyl]-1-(4-pyridyl) piperidine-4-carboxamide (0.359 g) in methylene chloride (10 ml). The mixture was stirred at ambient temperature for 2 hours. The precipitate was isolated and purified by column chromatography using a 9:1 mixture of methylene chloride and methanol as eluent. There was thus obtained N-{2-piperidinocarbonyl-2-[3-(4-tolyl)ureido]ethyl}-1-(4-pyridyl)-piperidine-4-carboxamide (0.13 g), m.p. 252–253° C.;

NMR Spectrum ($CD_3SOCD_3$) 1.4–1.8 (m, 10 H), 2.2 (s, 3 H), 2.25 (m, 1 H), 2.7–2.9 (m, 2 H), 3.05–3.25 (m, 2 H), 3.35–3.5 (m, 2 H), 3.5–3.6 (m, 2 H), 3.75–4.0 (m, 2 H), 4.8–5.0 (m, 1 H), 6.3 (d, 1 H), 6.7 (m, 2 H), 7.0 (d, 2 H), 7.25 (d, 2 H), 7.95 (m, 1 H), 8.05–8.15 (m, 1 H), 8.7 (s, 1 H);

Elemental Analysis

Found C, 65.8; H, 7.4; N, 16.9; $C_{27}H_{６}N_6O_3$ requires C, 65.8; H, 7.4; N, 17.1%.

EXAMPLE 23

Using an analogous procedure to that described in Example 2, 2-amino-N-{1-piperidinocarbonyl-2-[1-(4-pyridyl)piperidin-4-ylcarbonylamino]ethyl}acetamide hydrochloride salt was reacted with 4-toluenesulphonyl chloride to give N-{1-piperidinocarbonyl-2-[1-(4-pyridyl) piperidin-4-ylcarbonylamino]ethyl}-2-(4-toluenesulphonamido)aceta mide in S0 yield as a foam;

NMR Spectrum ($CD_3SOCD_3$) 1.3–1.8 (m, 10 H), 2.2–2.4 (m, 4 H), 2.7–2.9 (m, 2 H), 3.0–3.2 (m, 1 H), 3.3–3.6 (m, 12 H), 3.8–4.0 (m, 2 H), 4.8–4.95 (m, 1 H), 6.7–6.8 (m, 2 H), 7.35 (d, 2 H), 7.6–7.7 (m, 2 H), 8.05–8.2 (m, 2 H), 8.25 (d, 2 H).

The 2-amino-N-{1-piperidinocarbonyl-2-[1-(4-pyridyl)-piperidin-4-ylcarbonylamino]ethyl}acetamide hydrochloride salt used as a starting material was obtained as follows:

2-(tert-Butoxycarbonylamino)acetic acid N-hydroxysuccinimide ester [obtained by the reaction of that acid and N-hydroxysuccinimide in the presence of dicyclohexyl-carbodiimide, 0.272 g] was added to a stirred solution of b-[2-amino-2-(piperidinocarbonyl)ethyl]-1-(4-pyridyl)piperidine-4-carboxamide (0.359 g) in methylene chloride (5 ml). The mixture was stirred at ambient temperature for 16 hours. The mixture was partitioned between methylene chloride and 2 N aqueous sodium hydroxide solution. The organic phase was washed with water, dried ($MgSO_4$) and evaporated. The material so obtained was suspended in methylene chloride (25 ml) and hydrogen chloride gas was led into the solution for 5 minutes. A clear solution was obtained followed by the deposition of a precipitate. The mixture was evaporated to give the required starting material.

EXAMPLE 24

1,1'-Carbonyldiimidazole (0.11 g) was added to a stirred solution of 2-(2-naphthalenesulphonamido)acetic acid (0.182 g) in DMF (2 ml) which had been cooled to 5° C. The mixture was stirred at 5° C. for 30 minutes. A solution of 1-[4-amino-4-(piperidinocarbonyl)butyryl]-4-(4-pyridyl) piperazine (0.247 g) in DMF (3 ml) was added and the mixture was stirred at ambient temperature for 16 hours. The mixture was partitioned between ethyl acetate and water. The organic phase was washed with water, dried ($MgSO_4$) and evaporated. The residue was purified by column chromatography using a 95:5:0.5 mixture of ethvi acetate, methanol and aqueous ammonium hydroxide as eluent. There was thus obtained 2-(2-naphthaleneulphonamido)-N-{1-piperidinocarbonyl-3-[4-(4-pyridyl)piperazin-1-ylcarbonyl]propyl}acetamide (0.14 g);

NMR Spectrum ($CD_3SOCD_3$) 1.4–1.7 (m, 7 H), 1.8–1.95 (m, 1 H), 2.1–2.4 (m, 2 H), 3.2–3.6 (m, 14 H), 4.65–5.75 (m, 1 H), 6.8 (d, 2 H), 7.6–7.75 (m, 2 H), 7.8–7.9 (m, 1 H), 7.9–8.2 (m, 7 H), 8.45 (s, 1 H).

The 1-[4-amino-4-(piperidinocarbonyl)butyryl]-4-(4-pyridyl)-piperazine used as a starting material was obtained as follows:

A solution of piperidine (0.85 g) in methylene chloride (5 ml) was added dropwise to a solution of $N^2$-benzyloxycarbonyl-DL-glutamic anhydride [*J. Chem. Soc.,* 1950, 1954; 2.63 g] in methylene chloride (20 ml) which had been cooled to 0° C. The mixture was stirred at 0° C. for 1 hour. The mixture was extracted with ethyl acetate. The extract was acidified by the addition of concentrated hydrochloric acid, washed with water, dried ($MgSO_4$) and evaporated. The residue was purified by column chromatography using increasingly polar mixtures of ethyl acetate, acetic acid and methanol as eluent (99:1:0 to 99:1:5). There was thus obtained $N^2$-benzyloxycarbonyl-DL-glutamic $C^1$-piperidide (0.78 g), m.p. 92–93° C.

A portion (0.7 g) of the material so obtained was dissolved in DMF (10 ml) and cooled in an ice-bath. 1,1'-Carbonyldiimidazole (0.325 g) was added and the mixture was stirred at 5° C. for 30 minutes. A solution of 1-(4-pyridyl)piperazine (0.327 g) in DMF (2 ml) was added and the mixture was stirred at ambient temperature for 3 hours. The mixture was partitioned between ethyl acetate and water. The organic phase was washed with water, dried (MgSO$_4$) and evaporated. There was thus obtained 1-[4-(benzyloxycarbonylamino)-4-(piperidinocarbonyl)-butyryl]-4-(4-pyridyl)piperazine (0.55 g).

A portion (0.4 g) of the material so obtained, 10% palladium-on-carbon catalyst (0.1 g) and ethanol (20 ml) was stirred under an atmosphere of hydrogen for 6 hours. The mixture was filtered and the filtrate was evaporated. There was thus obtained 1-[4-amino-4-(piperidinocarbonyl)butyryl]-4-(4-pyridyl)piperazine (0.26 g);

NMR Spectrum (CDCl$_3$+CD$_3$SOCD$_3$) 1.4–1.7 (m, 6 H), 1.9–2.1 (m, 1 H), 2.3–2.6 (m, 2 H), 2.7–2.8 (m, 1 H), 3.2–3.8 (m, 12 H), 6.65 (d, 2 H), 8.3 (d, 2 H).

EXAMPLE 25

Using an analogous procedure to that described in Example 1, 2-[4-(4-pyridyl)piperazin-1-yl]acetyl chloride was reacted with N-(3-aminopropyl)naphthalene-2-sulphonamide to give N-[3-(2-naphthalene-sulphonamido)propyl]-2-[4-(4-pyridyl)piperazin-1-yl]acetamide in 34% yield;

NMR Spectrum (CD$_3$SOCD$_3$) 1.5–1.7 (m, 2 H), 2.75–2.9 (t, 2 H), 2.9–3.0 (s, 2 H), 3.1–3.25 (t, 2 H), 3.4–3.6 (m, 8 H), 7.6–7.9 (m, 6 H), 8.0–8.2 (m, 4 H), 8.4 (s, 1 H), 8.7–8.8 (d, 2 H);

Elemental Analysis

Found C, 61.6; H, 6.25; N, 15.0; C$_{24}$H$_{29}$N$_5$O$_3$S requires C, 61.2; H, 6.2; N, 14.8%.

The N-(3-aminopropyl)naphthalene-2-sulphonamide used as a starting material was obtained by the reaction of 2-naphthylsulphonyl chloride (2 g) and 1,3-diaminopropane (2.95 ml) in methylene chloride (25 ml) solution at ambient temperature for 16 hours.

EXAMPLE 26

Using an analogous procedure to that described in Example 1, 1-(4-pyridyl)piperidine-4-carbonyl chloride was reacted with N-(piperidin-4-yl)naphthalene-2-sulphonamide hydrochloride salt to give 4-(2-naphthalenesulphonamido)-1-[1-(4-pyridyl)piperidin-4-ylcarbonyl]-piperidine in 28% yield;

NMR Spectrum (CD$_3$SOCD$_3$) 1.1–1.4 (m, 2 H), 1.5–1.8 (m, 6 H), 2.6–2.8 (m, 1 H), 2.85–3.3 (m, 6 H), 3.7–3.9 (m, 1 H), 4.0–4.2 (m, 4 H), 6.9–7.1 (d, 2 H), 7.5–7.7 (m, 2 H), 7.8–8.1 (m, 6 H), 8.4 (s, 1 H);

Elemental Analysis

Found C, 62.7; H, 6.5; N, 11.0; C$_{26}$H$_{30}$N$_4$O$_3$S 0.5 H$_2$O requires C, 64.1; H, 6.3; N, 11.4%.

The N-(piperidin-4-yl)naphthalene-2-sulphonamide hydrochloride salt used as a starting material was obtained as follows:

A mixture of 4-amino-1-benzylpiperidine (1.8 ml), 2-naphthylsulphonyl chloride (2 g), triethylamine (3.7 ml) and methylene chloride (25 ml) was stirred at ambient temperature for 16 hours. The mixture was partitioned between ethyl acetate and water. The organic phase was washed with water, dried (MgSO$_4$) and evaporated. The residue was purified by column chromatography using increasingly polar mixtures of ethyl acetate and methanol as eluent. There was thus obtained N-(1-benzylpiperidin-4-yl)naphthalene-2-sulphonamide (2.98 g).

A mixture of a portion (0.5 g) of the material so obtained and methylene chloride (20 ml) was cooled in an ice-bath and 1-chloroethyl chloroformate (0.2 ml) was added. The mixture was stirred overnight at ambient temperature. The mixture was evaporated. The residue was dissolved in methanol (5 ml) and the solution was heated to reflux for 3 hours. The mixture was evaporated and the residue was purified by column chromatography using increasingly polar mixtures of ethyl acetate and methanol as eluent. There was thus obtained N-(piperidin-4-yl)naphthalene-2-sulphonamide hydrochloride salt (0.2 g);

NMR Spectrum (CD$_3$SOCD$_3$) 1.5–1.8 (m, 4 H), 2.75–2.9 (m, 2 H), 3.05–3.2 (m, 2 H), 3.25–3.4 (m, 1 H), 7.6–7.7 (m, 2 H), 7.8–7.9 (m, 1 H), 7.9–8.15 (m, 3 H), 8.4 (s, 1 H).

EXAMPLE 27

Using an analogous procedure to that described in Example 2, 3-amino-1-[1-(4-pyridyl)piperidin-4-ylcarbonyl]pyrrolidine hydrochloride salt was reacted with 2-naphthylsulphonyl chloride to give 3-(2-naphthalenesulphonamido)-1-[1-(4-pyridyl)piperidin-4-ylcarbonyl]pyrrolidine in 37% yield;

NMR Spectrum (CD$_3$SOCD$_3$+CD$_3$CO$_2$D) 1.5–2.0 (m, 6 H), 2.75–2.9 (m, 1 H), 3.1–4.0 (m, 7 H), 4.0–4.3 (m, 2 H), 7.0–7.1 (m, 2 H), 7.6–7.7 (m, 2 H), 7.9–8.0 (m, 1 H), 8.0–8.2 (m, 5 H), 8.5 (d, 1 H);

Elemental Analysis

Found C, 56.8; H, 5.5; N, 10.3; C$_{25}$H$_{28}$N$_4$SO$_3$ 2 H$_2$O 0.5 CH$_2$Cl$_2$ requires C, 56.4; H, 6.1; N, 10.3%.

The 3-amino-1-[1-(4-pyridyl)piperidin-4-ylcarbonyl]-pyrrolidine hydrochloride salt used as a starting material was obtained as follows:

Using an analogous procedure to that described in Example 1, 1-(4-pyridyl)piperidine-4-carbonyl chloride was reacted with 3-(tert-butoxycarbonylamino)pyrrolidine to give 3-(tert-butoxycarbonylamino)-1-[1-(4-pyridyl)piperidin-4-ylcarbonyl]pyrrolidine in 41% yield.

The material so obtained was treated with hydrogen chloride gas using an analogous procedure to that disclosed in the last paragraph of the portion of Example 1 which is concerned with the preparation of starting materials. There was thus obtained 3-amino-1-[1-(4-pyridyl)piperidin-4-ylcarbonyl]pyrrolidine hydrochloride salt in quantitative yield;

NMR Spectrum (CD$_3$SOCD$_3$) 1.5–1.8 (m, 2 H), 1.75–2.4 (m, 4 H), 2.8–3.0 (m, 1 H), 3.25–4.0 (m, 7 H), 4.2–4.4 (d, 2 H), 7.7 (d, 2 H), 8.1–8.3 (d, 2 H), 8.5–8.7 (m, 2 H).

EXAMPLE 28

The procedure described in Example 2 was repeated except that 8-chloronaphth-2-ylsulphonyl chloride was used in place of 2-naphthylsulphonyl chloride. There was thus obtained 1-(8-chloronaphth-2-ylsulphonyl)-4-[1-(4-pyridyl)piperidin-4-ylcarbonyl]piperazine in 74% yield;

NNR Spectrum (CD$_3$SOCD$_3$+CD$_3$CO$_2$D) 1.35–1.7 (m, 4 H), 2.85–3.15 (m, 7 H), 3.5–3.7 (m, 4 H), 3.95–4.1 (m, 2 H), 7.0 (d, 2 H), 7.75 (t, 1 H), 7.85–7.95 (m, 2 H), 8.1–8.2 (m, 3 H), 8.3 (d, 1 H), 8.55 (s, 1 H);

Elemental Analysis

Found C, 59.4; H. 5.5; N, 10.9; $C_{25}H_{27}ClN_4O_3S$ 0.5 $H_2O$ requires C, 59.1; H, 5.5; N, 11.0%.

EXAMPLE 29

Using an analogous procedure to that described in Example 2, 2-naphthylsulphonyl chloride was reacted with 3-ethoxycarbonyl-1-[1-(4-pyridyl)piperidin-4-ylcarbonyl]piperazine to give 2-ethoxycarbonyl-1-(2-naphthylsulphonyl)-4-[1-(4-pyridyl)piperidin-4-ylcarbonyl]piperazine in 31% yield;

NMR Spectrum $(CD_3SOCD_3, 100° C.)$ 1.05 (t, 3 H), 1.5–1.8 (m, 4 H), 2.9–3.25 (m, 5 H), 3.35–3.5 (m, 2 H), 3.7–4.15 (m, 7 H), 5.5–5.7 (m, 2 H), 6.75–6.95 (m, 2 H), 7.6–7.85 (m, 3 H), 8.0–8.15 (m, 5 H), 8.45 (d, 1 H);

Elemental Analysis

Found C, 60.4; H, 6.1; N, 10.1; $C_{28}H_{32}N_4O_5S$ $H_2O$ requires C, 60.6; H, 6.1; N, 10.1%.

The 3-ethoxycarbonyl-1-[1-(4-pyridyl)piperidin-4-ylcarbonyl]-piperazine used as a starting material was obtained as follows:

Using an analogous procedure to that described in Example 1, 1-(4-pyridyl)piperidine-4-carbonyl chloride was reacted with ethyl 1-benzylpiperazine-2-carboxylate (*Helv. Chim. Acta*, 1962, 45, 2383) to give 1-benzyl-2-ethoxycarbonyl-4-[1-(4-pyridyl)piperidin-4-ylcarbonyl]-piperazine in 67% yield.

A mixture of the material so obtained (0.667 g), trifluoroacetic acid (2 ml), 10% palladium-on-carbon catalyst (0.15 g) and methanol (20 ml) was stirred under 7 atmospheres pressure of hydrogen for 48 hours. The mixture was filtered and evaporated. The residue was partitioned between methylene chloride and a saturated aqueous sodium bicarbonate solution. The organic phase was washed with water, dried ($MgSO_4$) and evaporated. The residue was triturated under diethyl ether to give the required starting material in quantitative yield;

NMR Spectrum $(CD_3SOCD_3)$ 1.2–1.4 (m, 3H), 1.8–2.0 (m, 4H), 2.7–3.55 (m, 8H), 3.6–3.85 (m, 2H), 3.9–4.05 (m, 2H), 4.15–4.3 (m, 2H), 6.75 (d, 2H), 8.3 (d, 2H).

EXAMPLE 30

Using an analogous procedure to that described in Example 1, 1-1-(4-pyridyl)piperidine-4-carbonyl chloride hydrochloride salt was reacted with N-(2-aminoethyl)-2-(2-naphthalenesulphonamido)acetamide hydrochloride salt to give 2-(2-naphthalenesulphonamido)-N-{2-[1-(4-pyridyl)piperidin-4-ylcarbonylamino]ethyl}acetamide in 49% yield, m.p. 107–109° C.;

NMR Spectrum $(CD_3SOCD_3)$ 1.4–1.6 (m, 4H), 2.2–2.4 (m, 1H), 2.7–2.9 (m, 2H), 2.9–3.1 (m, 4H), 3.2–3.4 (m, 2H), 3.6–4.0 (m, 2H), 6.7–6.8 (d, 2H), 7.6–8.2 (m, 11H), 8.4 (s, 1H);

Elemental Analysis Found C, 59.7; H, 5.9; N, 14.1; $C_{25}H_{29}N_5O_4S$ 0.4$H_2O$ requires C, 59.7; H, 5.9; N, 13.9%.

The N-(2-aminoethyl)-2-(2-naphthalenesulphonamido)acetamide hydrochloride salt used as a starting material was obtained as follows:

1,1'-Carbonyldiimidazole (1.62 g) was added to a stirred solution of N-(2-naphthylsulphonyl)glycine (2.65 g) in DMF (20 ml) and the mixture was stirred at ambient temperature for 20 minutes. The mixture was cooled to 5° C. and a solution of 2-(N-tert-butoxycarbonylamino)ethylamine (1.6 g) in DHF (5 ml) was added. The mixture was stirred at ambient temperature for 2 hours. The mixture was evaporated and the residue was partitioned between ethyl acetate and 1M aqueous citric acid solution. The organic phase was washed with water, dried ($MgSO_4$) and evaporated. The residue was purified by column chromatography using increasingly polar mixtures of methylene chloride and ethyl acetate as eluent. There was thus obtained N-[2-(tert-butoxycarbonylamino)ethyl]-2-(2-naphthalenesulphonamido)acetamide (2.3 g), m.p. 150–152° C.

A portion (2 g) of the material so obtained was suspended in ethyl acetate and the mixture was cooled to 5° C. Hydrogen chloride gas was led into the mixture for 10 minutes to give a clear solution followed by the deposition of a precipitate. The solid was isolated, washed with diethyl ether and dried. There was thus obtained the required starting material (1.37 g);

NMR Spectrum $(CD_3SOCD_3)$ 2.7–2.9 (m, 2H), 3.15–3.3 (m, 2H), 3.4–3.5 (d, 2H), 7.6–7.9 (m, 3H), 7.9–8.3 (m, 8H), 8.45 (d, 1H).

EXAMPLE 31

Using an analogous procedure to that described in Example 3, N-(2-aminoethyl)-2-(2-naphthalenesulphonamido)acetamide hydrochloride salt, 1,1'-carbonyldiimidazole and 1-(4-pyridyl)piperazine were reacted to give 2-(2-naphthalenesulphonamido)-N-{2-[4-(4-pyridyl)piperazin-1-ylcarbonylamino]ethyl}acetamide in 10% yield;

NMR Spectrum $(CD_3SOCD_3+CD_3CO_2D)$ 3.1–3.2 (m, 4H), 3.4–3.6 (m, 6H), 3.6–3.7 (m, 4H), 7.1 (d, 2H), 7.6–7.75 (m, 2H), 7.8–7.9 (m, 1H), 8.0–8.05 (m, 1H), 8.1–8.2 (m, 4H), 8.4 (s, 1H);

Elemental Analysis Found C, 56.4; H, 5.9; N, 15.5; $C_{24}H_{28}N_6O_4S$ 0.5$H_2O$ 0.5 EtAc requires C, 56.8; H, 6.0; N, 15.3%.

EXAMPLE 32

Triethylamine (0.686 ml) was added to a stirred solution of 4-chloropyrimidine hydrochloride (0.151 g), 2-(2-naphthalenesulphonamido)-N-[2-(piperidin-4-ylcarbonylamino)ethyl]-acetamide hydrochloride salt (0.453 g) and ethanol (10 ml) and the mixture was stirred at ambient temperature for 4 days. The mixture was partitioned between ethyl acetate and water. The organic phase was washed with water, dried ($MgSO_4$) and evaporated. The residue was recrystallised from acetonitrile. There was thus obtained 2-(2-naphthalenesulphonamido)-N-{2-[1-(4-pyrimidinyl)piperidin-4-ylcarbonylamino]ethyl}acetamide (0.08 g), m.p. 178–179° C.;

NMR Spectrum $(CD_3SOCD_3)$ 1.3–1.6 (m, 2H), 1.65–1.85 (m, 2H), 2.3–2.45 (m, 1H), 2.8–3.05 (m, 6H), 3.4 (d, 2H), 4.3–4.5 (m, 2H), 6.8 (d, 1H), 7.3–7.8 (m, 3H), 7.8–7.95 (m, 2H), 8.0 (m, 2H), 8.1–8.2 (m, 3H), 8.4–8.5 (m, 2H);

Elemental Analysis Found C, 57.6; H, 5.7; N, 16.6; $C_{24}H_{28}N_6O_4S$ requires C, 58.0; H, 5.7; N, 16.9%.

The 2-(2-naphthalenesulphonamido)-N-[2-(piperidin-4-ylcarbonylamino)ethyl]acetamide used as a starting material was obtained as follows:

N-Hydroxybenzotriazole (0.135 g) and N-(3-dimethylaminopropyl)-N'-ethylcarbodiimide (0.191 g) were added in turn to a stirred solution of 1-(tert-butoxycarbonyl)piperidine-4-carboxylic acid (0.229 g) in DMF (10 ml) which had been cooled to 0° C. The mixture was stirred at 0° C. for 30 minutes. A solution of N-(2-aminoethyl)-2-(2-naphthalenesulphonamido)acetamide hydrochloride salt (0.343 g) in DMF (5 ml) was added, followed by triethylamine (0.101 g). The resultant mixture was allowed to warm to ambient temperature and was stirred for 3 hours. The mixture was partitioned between ethyl acetate and water. The organic phase was washed in turn with 2N aqueous hydrochloric acid, a saturated aqueous sodium bicarbonate solution and brine, dried ($MgSO_4$) and evaporated. There was thus obtained N-{2-[1-(tert-butoxycarbonyl)piperidin-4-ylcarbonylamino]ethyl}-2-(2-naphthalenesulphonamido)acetamide (0.192 g), m.p. 176–178° C.

The tert-butoxycarbonyl group was removed using an analogous procedure to that described in the last paragraph of the portion of Example 30 which is concerned with the preparation of starting materials. There was thus obtained 2-(2-naphthalenesulphonamido)-N-[2-(piperidin-4-ylcarbonylamino)ethyl]acetamide hydrochloride salt in 96% yield.

EXAMPLE 33

The procedure described in Example 32 was repeated except that 2-amino-4-chloropyrimidine hydrochloride salt was used in place of 4-chloropyrimidine hydrochloride salt. There was thus obtained N-{2-[1-(2-aminopyrimidin-4-yl)piperidin-4-ylcarbonylamnino]ethyl}-2-(2-naphthalenesulphonamido)acetamide in 53% yield, m.p. 197–199° C.;

NMR Spectrum ($CD_3SOCD_3$) 1.3–1.55 (m, 2H), 1.6–1.8 (m, 2H), 2.2–2.4 (m, 1H), 2.7–2.9 (m, 2H), 2.9–3.1 (m, 4H), 3.4 (s, 2H), 4.2–4.4 (m, 2H), 5.9 (s, 2H), 6.0 (d, 1H), 7.6–7.8 (m, 4H), 7.8–7.95 (m, 2H), 7.95–8.2 (m, 4H), 8.45 (s, 1H);

Elemental Analysis Found C, 55.9; H, 5.6; N, 19.1; $C_{24}H_{29}N_7O_4S$ requires C, 56.3; H, 5.7; N, 19.2%.

EXAMPLE 34

The procedure described in Example 32 was repeated except that 2-amino-4-chloro-6-methylpyrimidine hydrochloride was used in place of 4-chloropyrimidine hydrochloride and that the reaction mixture was heated to 80° C. for 16 hours. There was thus obtained N-{2-[1-(2-amino-6-methylpyrimidin-4-yl)piperidin-4-ylcarbonylamino]ethyl}-2-(2-naphthalenesulphonamido)acetamide in 38% yield, m.p. 225–226° C.; NMR Spectrum 1.3–1.5 (m, 2H), 1.6–1.8 (m, 2H), 2.05 (s, 3H), 2.2–2.4 (m, 1H), 2.7–2.9 (m, 2H), 2.95–3.1 (m, 4H), 3.45 (s, 2H), 4.2–4.4 (m, 2H), 5.8 (s, 2H), 5.9 (s, 1H), 7.6–7.75 (m, 3H), 7.8–8.0 (m, 2H), 8.0–8.2 (m, 4H), 8.45 (s, 1H);

Elemental Analysis Found C, 57.1; H, 6.0; N, 18.4; $C_{25}H_{31}N_7O_4S$ requires C, 56.9; H, 5.9; N, 18.4%.

EXAMPLE 35

Using an analogous procedure to that described in Example 18, 4-[2-(2-naphthalenesulphonamido)acetamido]butyric acid was reacted with 1-(4-pyridyl)piperazine to give 2-(2-naphthalenesulphonamido)-N-{3-[4-(4-pyridyl)piperazin-1-ylcarbonyl]propyl}acetamide in 21% yield as a foam;

NMR Spectrum ($CD_3SOCD_3$) 1.45–1.65 (m, 2H), 2.3 (t, 2H), 2.9–3.1 (m, 2H), 3.2–3.4 (m, 4H), 3.5–3.65 (m, 4H), 6.8 (m, 2H), 7.6–7.75 (m, 4H), 8.0–8.3 (m, 6H), 8.45 (s, 1H);

Elemental Analysis Found C, 57.7; H, 6.1; N, 12.7; $C_{25}H_{29}N_5O_4S$ $H_2O$ 0.5EtAc requires C, 58.2; H, 6.3; N, 12.6%.

The 4-[2-(2-naphthalenesulphonamido)acetamido]butyric acid used as a starting material was obtained as follows:

Using an analogous procedure to that described in the first paragraph of the portion of Example 30 which is concerned with the preparation of starting materials, N-(2-naphthylsulphonyl)glycine was reacted with methyl 4-aminobutyrate to give methyl 4-[2-(2-naphthalenesulphonamido)acetamido]butyrate in 56% yield.

The material so obtained was hydrolysed using an analogous procedure to that described in Example 9. There was thus obtained the required starting material in 79% yield, m.p. 187–189° C.;

NMR Spectrum ($CD_3SOCD_3+CD_3CO_2D$) 1.5–1.7 (m, 2H), 2.15 (t, 2H), 3.0 (t, 2H), 3.5 (s, 2H), 7.6–7.8 (m, 2H), 7.8–7.9 (m, 1H), 7.95–8.2 (m, 3H), 8.5 (s, 1H).

EXAMPLE 36

N-(3-Dimethylaminopropyl)-N'-ethylcarbodiimide (0.21 g) was added to a stirred mixture of N-(2-naphthylsulphonyl)glycine (0.265 g), 1-(4-pyridyl)piperazine (0.169 g) and DMF (10 ml) which had been cooled to 5° C. The mixture was stirred at ambient temperature for 3 hours. The mixture was partitioned between ethyl acetate and water. The organic phase was washed with water, dried ($MgSO_4$) and evaporated. The residue was purified by column chromatography using a 19:1 mixture of methylene chloride and methanol as eluent. There was thus obtained N-[4-(4-pyridyl)piperazin-1-ylcarbonylmethyl]naphthalene-2-sulphonamide (0.126 g), m.p. 182–184° C.;

NMR Spectrum ($CD_3SOCD_3$) 3.1–3.6 (m, 8H), 3.8–3.9 (m, 2H), 6.7–6.8 (m, 2H), 7.6–7.75 (m, 2H), 7.75–7.9 (m, 2H), 8.0–8.2 (m, 5H), 8.45 (s, 1H);

Elemental Analysis Found C, 61.0; H. 5.3; N, 13.5; $C_{21}H_{22}N_4O_3S$ requires C, 61.4; H, 5.4; N, 13.5%.

EXAMPLE 37

Using an analogous procedure to that described in Example 36, 4-(2-naphthalenesulphonamido)butyric acid was reacted with 1-(4-pyridyl)piperazine to give N-{3-[4-(4-pyridyl)piperazin-1-ylcarbonyl]propyl}naphthalene-2-sulphonamide in 15% yield as a foam;

NMR Spectrum ($CD_3SOCD_3$) 1.7–1.9 (m, 2H), 2.3–2.4 (t, 2H), 2.95–3.05 (m, 2H), 3.2–3.3 (m, 4H), 3.4–3.5 (m, 2H), 3.6–3.75 (m, 2H), 5.4–5.6 (d, 1H), 6.5–6.6 (m, 2H), 7.5–7.65 (mi, 2H), 7.75–8.0 (m, 4H), 8.2–8.3 (m, 2H), 8.35 (s, 1H).

The 4-(2-naphthalenesulphonamido)butyric acid used as a starting material was obtained as follows:

Using an analogous procedure to that described in Example 2, 2-naphthylsulphonyl chloride was reacted with methyl 4-aminobutyrate to give methyl 4-(2-naphthalenesulphonamido)butyrate in 94% yield.

The material so obtained was hydrolysed using an analogous procedure to that described in Example 9. There was thus obtained the required starting material in 88% yield, m.p. 123–125° C.;

NMR Spectrum ($CDCl_3$) 1.7–1.9 (m, 2H), 2.35 (t, 2H), 2.9–3.1 (m, 2H), 6.3–6.5 (m, 1H), 7.5–7.7 (m, 2H), 7.8–8.1 (m, 4H), 8.4 (s, 1H).

EXAMPLE 38

A solution of 5-(2-pyridyl)thien-2-ylsulphonyl chloride [Chem. Abs., 1983, 98, 215349; 0.162 g] in methylene chloride (5 ml) was added to a stirred mixture of 1-[1-(4-pyridyl)piperidin-4-ylcarbonyl]piperazine (0.314 g), triethylamine (0.9 ml) and methylene chloride (15 ml). The resultant mixture was stirred at ambient temperature of 18 hours. The mixture was partitioned between methylene chloride and water. The organic phase was washed with water, dried (MgSO$_4$) and evaporated. The residue was purified by column chromatography using increasingly polar mixtures of methylene chloride and methanol as eluent. There was thus obtained 1-[1-(4-pyridyl)piperidin-4-ylcarbonyl]-4-[5-(2-pyridyl)thien-2-ylsulphonyl]piperazine (0.231 g, 74%);

NMR Spectrum (CD$_3$SOCD$_3$) 1.4–1.7 (m, 4H), 2.8–3.1 (m, 7H), 3.55–3.75 (m, 4H), 3.85–3.95 (m, 2H), 6.8 (d, 2H), 7.35–7.45 (m, 1H), 7.65 (d, 1H), 7.9–8.0 (m, 2H), 8.05–8.15 (m, 3H), 8.55–8.6 (m, 1H);

Elemental Analysis Found C, 57.2; H, 5.5; N, 13.9; C$_{24}$H$_{27}$N$_5$O$_3$S$_2$ 0.25H$_2$O requires C, 57.4; H, 5.5; N, 14.0%.

EXAMPLE 39

Using an analogous procedure to that described in Example 2, 1-[1-(4-pyridyl)piperidin-4-ylcarbonyl]piperazine was reacted with the appropriate (E)-styrenesulphonyl chloride. There were thus obtained the (E)-styrenes disclosed in Table I, the structures of which were confirmed by NMR spectroscopy. Unless otherwise stated, the appropriate (E)-styrenesulphonyl chlorides were obtained from the corresponding styrenes using an analogous procedure to that described in Note b. below Table I.

TABLE I

| Example 39 Compound No. | R | m.p. (° C.) | Yield (%) |
| --- | --- | --- | --- |
| 1[a] | hydrogen | gum | 27 |
| 2[b] | 4-chloro | 172–173 | 32 |
| 3[c] | 4-methyl | 223–226 | 42 |
| 4[d] | 2-methyl | 148–149 | 37 |
| 5[e] | 4-fluoro | 125–126 | 55 |
| 6[f] | 2-chloro | foam | 39 |
| 7[g] | 3-chloro | foam | 49 |
| 8[h] | 3,4-dichloro | foam | 33 |
| 9[i] | 4-bromo | foam | 54 |
| 10[j] | 4-trifluoromethyl | foam | 30 |

Notes a. The product gave the following NMR signals (CD$_3$SOCD$_3$) 1.45–1.8 (m, 4H), 2.95–3.25 (m, 7H), 3.5–3.75 (m, 4H), 4.12 (m, 2H), 7.05 (d, 2H), 7.38 (m, 5H), 7.75 (m, 2H), 8.2 (d, 2H).

b. The product gave the following NMR signals (CD$_3$SOCD$_3$) 1.4–1.65 (m, 4H), 2.8–3.0 (m, 3H), 3.12 (m, 4H), 3.65 (m, 4H), 3.92 (m, 2H), 6.8 (d, 2H), 7.4 (d, 2H), 7.5 (d, 2H), 7.8 (d, 2H), 8.15 (d, 2H).

The 4-chlorostyrenesulphonyl chloride used as a starting material was obtained as follows:

Sulphuryl chloride (1.37 ml) was added dropwise to DMF (1.55 ml) which was stirred and cooled to a temperature in the range 0 to 5° C. The mixture was stirred at ambient temperature for 30 minutes. 4-Chlorostyrene (1.2 ml) was added and the mixture was stirred and heated to 90° C. for 3.5 hours. The mixture was cooled to ambient temperature and poured onto a mixture (25 ml) of ice and water. The precipitate so formed was isolated, washed with water and dried. There was thus obtained 4-chloro-β-styrenesulphonyl chloride (1.8 g);

NMR Spectrum (CD$_3$SOCD$_3$) 6.95 (m, 2H), 7.4 (a, 2H), 7.55 (d, 2H).

c. The product gave the following NMR signals (CD$_3$SOCD$_3$) 1.4–1.85 (m, 4H), 2.3 (s, 3H), 2.95–3.3 (m, 7H), 3.6 (m, 4H), 4.07 (mu, 2H), 7.0 (m, 3H), 7.25 (m, 3H), 7.5 (d, 2H), 8.05 (d, 2H).

d. The product gave the following NMR signals (CD$_3$SOCD$_3$) 1.45–1.75 (m, 4H), 2.4 (s, 3H), 2.85–3.25 (m, 7H), 3.55–3.75 (m, 4H), 3.92 (m, 2H), 6.8 (d, 2H), 7.1–7.4 (m, 4H), 7.68 (m, 2H), 8.15 (d, 2H).

e. The product gave the following NMR signals (CD$_3$SOCD$_3$) 1.45–1.75 (m, 4H), 2.85–3.0 (m, 3H), 3.05–3.2 (m, 4H), 3.5–3.75 (m, 4H), 3.92 (m, 2H), 6.85 (d, 2H), 7.2–7.5 (m, 4H), 7.85 (m, 2H), 8.15 (d, 2H).

f. The product gave the following NMR signals (CD$_3$SOCD$_3$) 1.45–1.75 (m, 4H), 2.85–2.95 (m, 3H), 3.05–3.25 (m, 4H), 3.55–3.75 (m,.4H), 3.92 (m, 2H), 6.8 (d, 2H), 7.4–7.7 (m, 5H), 8.0 (m, 1H), 8.1 (d, 2H).

g. The product gave the following NMR signals (CD$_3$SOCD$_3$) 1.45–1.75 (m, 4H), 2.85–3.0 (m, 3), 3.0–3.2 (m, 4H), 3.55–3.75 (m, 4H), 3.92 (m, 2H), 6.8 (d, 2H), 7.4–7.5 (m, 4H), 7.72 (m, 1H), 7.93 (m, 1H), 8.15 (d, 2H).

h. The product gave the following NMR signals (CD$_3$SOCD$_3$+CD$_3$CO$_2$D) 1.5–1.9 (m, 4H), 3.0–3.3 (m, 7H), 3.55–3.75 (m, 4H), 4.15 (m, 2H), 7.1 (d, 2H), 7.4 (d, 2H), 7.7 (m, 2H), 8.1 (s, 1H), 8.15 (d, 2H).

i. The product gave the following NMR signals (CD$_3$SOCD$_3$+CD$_3$CO$_2$D) 1.55–1.85 (m, 4H), 3.0–3.35 (m, 7H), 3.6–3.75 (m, 4H), 4.17 (m, 2H), 7.1 (d, 2H), 7.15–7.5 (m, 2H), 7.65 (m, 4H), 8.15 (d, 2H).

j. The product gave the following NMR signals (CD$_3$SOCD$_3$+CD$_3$CO$_2$D) 1.5–1.85 (m, 4H), 3.0–3.3 (m, 7H), 3.55–3.75 (m, 4H), 4.15 (m, 2H), 7.1 (d, 2H), 7.5 (m, 2H), 7.8 (d, 2H), 7.95 (d, 2H), 8.15 (d, 2H).

EXAMPLE 40

Using an analogous procedure to that described in Example 2, 1-[1-(4-pyridyl)piperidin-4-ylcarbonyl]piperazine was reacted with the appropriate 2-naphthalenesulphonyl chloride. There were thus obtained the compounds disclosed in Table II, the structures of which were confirmed by NMR spectroscopy. Unless otherwise stated, the appropriate naphthylsulphonyl chlorides were obtained from the corresponding naphthalenes using an analogous procedure to that described in Note c. below Table III in Example 41.

TABLE II

| Example 40 Compound No. | R | m.p. (° C.) | Yield (%) |
| --- | --- | --- | --- |
| 1[a] | 4-chloro | 199–203 | 38 |
| 2[b] | 7-chloro | glass | 18 |
| 3[c] | 7-ethoxy | glass | 13 |
| 4[d] | 6,7-dimethoxy | glass | 30 |

TABLE II-continued

[Structure: pyridyl-N-piperidine-CO-N-piperazine-N-SO2-naphthyl-R, with positions 4 and 6 labeled on naphthyl]

| Example 40 Compound No. | R | m.p. (° C.) | Yield (%) |
|---|---|---|---|
| 5[e] | 6-chloro | 115 (decomposes) | 82 |
| 6[f] | 6-bromo | 142–145 | 81 |
| 7[g] | 6-methoxy | gum | 28 |
| 8[h] | 7-methoxy | glass | 29 |
| 9[i] | 6-fluoro | 108–111 (decomposes) | 73 |

Notes a. The product gave the following NMR signals (CD$_3$SOCD$_3$) 1.35–1.65 (m, 4H), 2.75–2.9 (m, 3H), 3.0–3.15 (m, 4H), 3.6 (m, 4H), 3.85 (m, 2H), 6.75 (d, 2H), 7.9 (m, 3H), 8.1 (d, 2H), 8.35 (t, 2H), 8.5 (s, 1H).

b. The product gave the following NMR signals (CD$_3$SOCD$_3$) 1.35–1.65 (m, 4H), 2.8–3.05 (m, 7H), 3.5–3.7 (m, 4H), 3.8–3.9 (m, 2H), 6.75 (d, 2H), 7.78 (m, 2H1), 8.15 (m, 4H), 8.45 (d, 1H).

c. The product gave the following NMR signals (CD$_3$SOCD$_3$) 1.35–1.7 (m, 4H), 1.45 (t, 3H), 2.8–3.05 (m, 7H), 3.3 (m, 2H), 3.5–3.7 (m, 4H), 3.83 (m, 2H), 4.2 (m, 2H), 6.85 (d, 2H), 7.35 (m, 1H), 7.58 (m, 2H), 7.95–8.15 (m, 4H), 8.3 (d, 1H).

d. The product gave the following NMR signals (CD$_3$SOCD$_3$) 1.35–1.65 (m, 4H), 2.75–3.0 (m, 7H), 3.5–3.7 (m, 4H), 3.85 (m, 2H), 3.95 (s, 6H), 6.75 (d, 2H), 7.5 (s, 1H), 7.6 (m, 2H), 7.95 (d, 1H), 8.1 (m, 2H), 8.25 (s, 1H).

e. The product gave the following NMR signals (CD$_3$SOCD$_3$+CD$_3$CO$_2$D) 1.45–1.8 (m, 4H), 2.9–3.1 (m, 5H), 3.22 (m, 2H), 3.55–3.75 (m, 4H), 4.1 (m, 2H), 7.05 (d, 2H), 7.65–7.85 (m, 2H), 8.1–8.25 (m, 5H), 8.45 (s, 1H); and the following analytical data: Found C, 58.9; H, 5.3; N, 10.9; C$_{25}$H$_{27}$ClN$_4$O$_3$S 0.2CH$_2$Cl$_2$ requires C, 58.7; H, 5.3; N, 10.9%.

The 6-chloro-2-naphthylsulphonyl chloride used as a starting material was obtained as follows:

A solution of sodium nitrite (2.7 g) in water (5 ml) was added during 2 hours to a stirred mixture of 6-amino-2-naphthalenesulphonic acid (8.8 g), dilute aqueous hydrochloric acid (2.8% weight/volume, 20 ml) and water (15 ml) which had been cooled to 0° C. The mixture was stirred at 0° C. for 30 minutes and then poured onto a stirred suspension of cuprous chloride (3.96 g) in dilute aqueous hydrochloric acid (2.8%, 20 ml). The mixture was stored at ambient temperature for 18 hours. The mixture was evaporated to give 6-chloro-2-naphthalenesulphonic acid which was used without further purification.

The material was suspended in DMF (40 ml) and cooled to 5° C. Thionyl chloride (8.6 ml) was added dropwise and the mixture was stirred at 5° C. for 3 hours. The mixture was poured onto ice and extracted with methylene chloride. The organic solution was dried (MgSO$_4$) and evaporated. The residue was purified by column chromatography using a 20:1 mixture of hexane and ethyl acetate as eluent. There was thus obtained 6-chloro-2-naphthylsulphonyl chloride (2.49 g);

NMR Spectrum (CD$_3$SOCD$_3$) 7.45 (m, 1H), 7.8 (m, 1H), 7.85 (d, 1H), 8.05 (m, 2H), 8.2 (s, 1H).

f. The product gave the following NMR signals (CD$_3$SOCD$_3$) 1.35–1.65 (m, 4H), 2.75–3.05 (m, 7H), 3.5–3.7 (m, 4H), 3.87 (m, 2H), 6.8 (d, 2H), 7.85 (m, 2H), 8.05–8.25 (m, 4H), 8.4 (d, 1H), 8.5 (d, 1H).

The 6-bromo-2-naphthylsulphonyl chloride used as a starting material was obtained in 22% yield from 6-amino-2-naphthalenesulphonic acid using an analogous procedure to that described in Note e above except that hydrobromic acid and cuprous bromide were used in place of hydrochloric acid and cuprous chloride respectively. The material gave the following NMR signals (CD$_3$SOCD$_3$) 7.65 (m, 1H), 7.75–8.0 (m, 3H), 8.15–8.2 (m, 2H).

g. The product gave the following NMR signals (CD$_3$SOCD$_3$, 100° C.) 1.48–1.73 (m, 4H), 2.75–3.02 (m, 3H), 3.06–3.11 (t, 4H), 3.56 (t, 4H), 3.76 (t, 1H), 3.81 (t, 1H), 3.95 (s, 3H), 6.7 (d, 2H), 7.32 (m, 1H), 7.44 (m, 1H), 7.71 (m, 1H), 8.03 (m, 2H), 8.12 (d, 2H), 8.31 (d, 1H).

The 6-methoxy-2-naphthylsulphonyl chloride used as a starting material was obtained as follows:

A mixture of sodium 6-hydroxy-2-naphthylsulphonate (5 g) and DMSO (100 ml) was added to a stirred suspension of sodium hydride (60% dispersion in mineral oil, 1 g) in DMSO (20 ml) and the mixture was stirred at ambient temperature for 30 minutes. The mixture was cooled to 10° C. and methyl iodide (22 ml) was added dropwise. The mixture was allowed to warm to ambient temperature and was stirred for 2 hours. The mixture was poured into acetone and the precipitate was isolated and washed in turn with acetone and diethyl ether. There was thus obtained sodium 6-methoxy-2-naphthylsulphonate (3.3 g).

Thionyl chloride (0.82 ml) was added to a stirred solution of a portion (0.96 g) of the material so obtained in DMF (10 ml). The mixture was stirred at ambient temperature for 2 hours. The mixture was poured onto ice. The precipitate was isolated and dried. There was thus obtained 6-methoxy-2-naphthylsulphonyl chloride (0.7 g) which was used without further purification.

h. The product gave the following NMR signals (CD$_3$SOCD$_3$) 1.4–1.65 (m, 4H), 2.75–3.0 (m, 7H), 3.5–3.7 (m, 4H), 3.88 (m, 2H), 6.75 (d, 2H), 7.35–7.65 (m, 3H), 7.95–8.1 (m, 4H), 8.35 (s, 1H).

The 7-methoxy-2-naphthylsulphonyl chloride used as a starting material was obtained from sodium 7-hydroxy-2-naphthylsulphonate using analogous procedures to those described in Note g above.

i. The product gave the following NMR signals (CD$_3$SOCD$_3$+CD$_3$CO$_2$D) 1.45–1.8 (m, 4H), 2.9–3.1 (m, 5H), 3.22 (m, 2H), 3.55–3.75 (m, 4H), 4.12 (m, 2H), 7.1 (d, 2H), 7.57 (m, 1H), 7.75–7.9 (m, 2H), 8.15 (m, 2H), 8.3 (m, 1H), 8.5 (d, 1H).

The 6-fluoro-2-naphthylsulphonyl chloride used as a starting material was obtained as follows:

6-Amino-2-naphthalenesulphonic acid (5.41 g) was added portionwise during 10 minutes to a stirred suspension of nitrosonium tetrafluoroborate (3;12 g) in methylene chloride (100 ml) which had been cooled to 5° C. The mixture was stirred at 5° C. for 2 hours and at ambient temperature for 18 hours. The mixture was evaporated and 1,2-dichlorobenzene (100 ml) was added to the residue. The mixture was stirred and heated to 150° C. for 2 hours. The mixture was cooled to 5° C. and thionyl chloride (3.6 ml) and DHF (10 ml) were added. The mixture was stirred at ambient temperature for 18 hours. The mixture was partitioned between methylene chloride and water. The organic phase was dried (MgSO$_4$) and evaporated. The residue was purified by column chromatography using a 9:1 mixture of hexane and ethyl acetate as eluent. There was thus obtained 6-fluoro-2-naphthylsulphonyl chloride (1.53 g);

NMR Spectrum (CD$_3$SOCD$_3$) 7.4 (m, 1H), 7.65–7.9 (m, 3H), 8.05 (m, 2H), 8.2 (d, 1H).

EXAMPLE 41

Using an analogous procedure to that described in Example 2, 1-[1-(4-pyridyl)piperidin-4-ylcarbonyl] piperazine was reacted with the appropriate benzenesulphonyl chloride. There were thus obtained the compounds disclosed in Table III, the structures of which were confirmed by NMR spectroscopy.

TABLE III

| Example 41 Compound No. | R | m.p. (° C.) | Yield (%) |
|---|---|---|---|
| 1[a] | 4-bromo | glass | 67 |
| 2[b] | 4-phenyl | glass | 64 |
| 3[c] | 4-(4-chlorophenyl) | glass | 61 |

Notes a. The product gave the following NMR signals (CD$_3$SOCD$_3$) 1.4–1.7 (m, 4H), 2.8–3.0 (m, 7H), 3.5–3.7 (m, 4H), 3.8–3.95 (m, 2H), 6.75 (d, 2H), 7.65 (d, 2H), 7.85 (d, 2H), 8.12 (broad s, 2H).

b. The product gave the following NMR signals (CD$_3$SOCD$_3$) 1.35–1.37 (m, 4H), 2.8–3.0 (m, 7H), 3.5–3.7 (m, 4H), 3.88 (m, 2H), 6.8 (d, 2H), 7.5 (m, 3H), 7.78 (m, 4H), 7.95 (d, 2H), 8.1 (d, 2H).

c. The product gave the following NMR signals (CD$_3$SOCD$_3$+CD$_3$CO$_2$D) 1.55–1.8 (m, 4H), 2.8–3.05 (m, 3H), 3.15 (t, 4H), 3.6 (t, 4H), 3.85 (m, 2H), 6.75 (d, 2H), 7.55 (d, 2H), 7.75 (d, 2H), 7.9 (d, 2H), 8.15 (d, 2H).

The 4'-chloro-4-biphenylylsulphonyl chloride used as a starting material was obtained as follows:

Chlorosulphonic acid (9 ml) was added dropwise to a stirred solution of 4-chlorobiphenyl (21 g) in chloroform (200 ml) and the mixture was stirred at ambient temperature for 30 minutes. The precipitate was isolated and washed with chloroform (50 ml). There was thus obtained 4'-chloro-4-biphenylylsulphonic acid (26.8 g).

Thionyl chloride (0.85 ml) was added dropwise to a stirred solution of 4'-chloro-4-biphenylylsulphonic acid (1.7 g) in DMF (120 ml) which had been cooled to 5° C. The mixture was stirred at ambient temperature for 3 hours. The mixture was poured into water and the resultant precipitate was isolated, dissolved in diethyl ether, dried (MgSO$_4$) and re-isolated by evaporation of the solvent. There was thus obtained 4'-Chloro-4-biphenylylsulphonyl chloride (0.7 g) which was used without further purification.

EXAMPLE 42

Using an analogous procedure to that described in Example 2, 1-[1-(4-pyridyl)piperidin-4-ylcarbonyl] piperazine was reacted with dibenzofuran-3-sulphonyl chloride to give 1-(dibenzofuran-3-ylsulphonyl)-4-[1-(4-pyridyl)piperidin-4-ylcarbonyl]piperazine as a glassy solid in 75% yield;

NMR Spectrum (CD$_3$SOCD$_3$) 1.35–1.75 (m, 4H), 2.8–3.1 (m, 7H), 3.6–3.8 (m, 4H), 3.9–4.0 (m, 2H), 6.8 (d, 21H), 7.67 (m, 2H), 7.85–8.2 (m, 5H), 8.5 (d, 1H), 8.75 (d, 1H);

Elemental Analysis Found C, 62.8; H, 5.5; N, 10.8; C$_{27}$H$_{28}$N$_4$O$_4$S 0.5H$_2$O requires C, 63.1; H, 5.7; N, 10.9%.

EXAMPLE 43

A mixture of 2-ethoxycarbonyl-1-(2-naphthylsulphonyl)-4-[1-(4-pyridyl)piperidin-4-ylcarbonyl]piperazine, 2N aqueous sodium hydroxide solution (0.37 ml) and methanol (4 ml) was stirred at ambient temperature for 3 hours. The mixture was evaporated. The residue was dissolved in water (4 ml) and acidified by the addition of glacial acetic acid. The resultant precipitate was washed with water, dried and triturated under diethyl ether. There was thus obtained 1-(2-naphthylsulphonyl)-4-[1-(4-pyridyl)piperidin-4-ylcarbonyl]-piperazine-2-carboxylic acid (0.082 g), m.p. 188–193° C.;

NMR Spectrum (CD$_3$SOCD$_3$+CD$_3$CO$_2$D) 1.45–1.8 (m, 4H), 2.9–3.4 (m, 5H), 3.78 (m, 1H), 4.1 (m, 2H), 4.5 (m, 2H), 7.1 (d, 2H), 7.6–7.9 (m, 3H), 8.0–8.2 (m, 5H), 8.45 (d, 1H);

Elemental Analysis Found C, 59.6; H, 5.7; N, 10.3; C$_{26}$H$_{28}$N$_4$O$_5$S 0.75H$_2$O requires C, 59.8; H, 5.7; N, 10.7%.

EXAMPLE 44

Using an analogous procedure to that described in Example 1, 1-(4-pyridyl)piperidine-4-carbonyl chloride was reacted with ethyl 1-(2-naphthylsulphonyl)piperazine-3-carboxylate to give 2-ethoxycarbonyl-4-(2-naphthylsulphonyl)-1-[1-(4-pyridyl)piperidin-4-ylcarbonyl] piperazine as a glassy solid in 9% yield;

NMR Spectrum (CD$_3$SOCD$_3$) 1.3 (t, 3H), 1.65–2.1 (m, 4H), 2.5 (m, 2H), 2.78 (m, 1H), 3.05 (m, 2H), 3.6–3.95 (m, 5H), 4.2 (m, 2H), 4.4 (m, 1H), 5.07 (m, 1H), 5.3 (m, 1H), 6.65 (d, 2H), 7.7 (m, 3H), 7.98 (m, 3H), 8.2 (d, 2H), 8.35 (d, 1H);

Elemental Analysis Found C, 62.3; H, 6.5; N, 10.8; C$_{28}$H$_{32}$N$_4$O$_5$S requires C, 62.7; H, 6.1; N, 10.4%.

The ethyl 1-(2-naphthylsulphonyl)piperazine-3-carboxylate used as a starting material was prepared as follows:

Using an analogous procedure to that described in Example 2, ethyl 1-benzylpiperazine-2-carboxylate was reacted with 2-naphthylsulphonyl chloride to give ethyl 1-benzyl-4-(2-naphthylsulphonyl)piperazine-2-carboxylate in 93% yield.

1-Chloroethyl chloroformate (1.5 ml) was added to a solution of ethyl 1-benzyl-4-(2-naphthylsulphonyl) piperazine-2-carboxylate (2.44 g) in 1,2-dichloroethane (50 ml) and the mixture was stirred and heated to reflux for 48 hours. The mixture was evaporated and the residue was triturated under hexane. Methanol (50 ml) was added to the resultant gum and the mixture was heated to reflux for 2 hours. The mixture was evaporated and the residue was partitioned between methylene chloride and water. The organic phase was dried (MgSO$_4$) and evaporated. The residue was purified by column chromatography using increasingly polar mixtures of methylene chloride and methanol as eluent. There was thus obtained ethyl 1-(2-naphthylsulphonyl)piperazine-3-carboxylate as a gum (1.55 g);

NMR Spectrum (CDCl$_3$) 1.3 (t, 3H), 2.65–3.0 (m, 3H), 3.5 (m, 2H), 3.75 (m, 1H), 4.2 (q, 2H), 7.7 (m, 3H), 7.98. (m, 3H), 8.35 (d, 1H).

EXAMPLE 45

Using an analogous procedure to that described in Example 14, 1-(4-pyridyl)piperazine was reacted with 1-(2-naphthylsulphonyl)piperidine-3-carboxylic acid to give 1-[1-(2-naphthylsulphonyl)-piperidin-3-ylcarbonyl]-4-(4-pyridyl)piperazine as a foam in 25% yield;

NMR Spectrum (CD$_3$SOCD$_3$) 0.95–1.75 (m, 6H), 2.3–2.45 (m, 2H), 2.6 (m, 1H), 3.5–3.75 (m, 8H), 7.05 (d, 2H), 7.6–7.75 (m, 3H), 8.1 (m, 5H), 8.4 (s, 1H).

The 1-(2-naphthylsulphonyl)piperidine-3-carboxylic acid used as a starting material was obtained as follows:

Using an analogous procedure to that described in Example 2, ethyl piperidine-3-carboxylate was reacted with 2-naphthylsulphonyl chloride to give ethyl 1-(2-naphthylsulphonyl)piperidine-3-carboxylate in 62% yield.

A mixture of the material so obtained (1.33 g), potassium hydroxide (0.43 g) and ethanol (17 ml) was stirred and heated to 80° C. for 4 hours. The mixture was evaporated. The residue was dissolved in water (5 ml) and the solution was acidified by the addition of 2N aqueous hydrochloric acid. The resultant precipitate was isolated, washed with water and dried. There was thus obtained 1-(2-naphthylsulphonyl)piperidine-3-carboxylic acid (0.81 g);

NMR Spectrum (CD$_3$SOCD$_3$) 1.45–1.64 (m, 2H), 1.8–1.95 (m, 2H), 2.25 (m, 1H), 2.5 (m, 2H), 3.58 (m, 2H), 7.72 (m, 3H), 8.15 (m, 3H), 8.45 (d, 1H).

EXAMPLE 46

Using an analogous procedure to that described in Example 1 except that DMF was used in place of methylene chloride as the reaction solvent, 1-(4-pyridyl)piperidine-4-carbonyl chloride was reacted with 1-(2-naphthylmethyl)-2-oxopiperazine trifluoroacetate salt to give 1-(2-naphthylmethyl)-2-oxo-4-[-(4-pyridyl)piperidin-4-ylcarbonyl]piperazine in 18% yield;

NMR Spectrum (CD$_3$SOCD$_3$) 1.45–1.75 (m, 4H), 2.85–3.05 (m, 3H), 3.3 (m, 2H), 3.65–4.4 (m, 6H), 4.75 (s, 2H), 6.8 (d, 2H), 7.5 (m, 3H), 7.8 (s, 1H), 7.9 (d, 2H), 8.1 (d, 2H);

Elemental Analysis Found C, 70.6; H, 6.7; N, 12.5; C$_{26}$H$_{28}$N$_4$O$_2$ 0.8H$_2$O requires C, 70.5; H, 6.7; N, 12.6%.

The 1-(2-naphthylmethyl)-2-oxopiperazine trifluoroacetate salt used as a starting material was obtained as follows:

Di-tert-butyl pyrocarbonate (7.75 g) was added portionwise to a stirred mixture 2-oxopiperazine (3.23 g), potassium carbonate (4.46 g), tert-butudol (15 ml) and water (15 ml). The mixture was stirred at ambient temperature for 2 hours. The mixture was extracted with ethyl acetate. The organic phase was dried and evaporated. The residue was recrystallised from ethyl acetate. There was thus obtained 4-tert-butoxycarbonyl-2-oxopiperazine (5.31 g), m.p. 157–159° C.

Sodium hydride (60% dispersion in mineral oil, 0.145 g) was added portionwise to a stirred mixture of 4-tert-butoxycarbonyl-2-oxopiperazine (0.5 g) and DMF (15 ml) which had been cooled to 5° C. The mixture was stirred at that temperature for 1.5 hours. A solution of 2-bromomethylnaphthalene (0.552 g) in DMF (3 ml) was added dropwise. The mixture was allowed to warm to ambient temperature and was stirred for 18 hours. The mixture was partitioned between methylene chloride and water. The organic phase was dried (MgSO$_4$) and evaporated. The residue was purified by column chromatography using a 3:2 mixture of hexane and ethyl acetate as eluent.

There was thus obtained 4-tert-butoxycarbonyl-1-(2-naphthylmethyl)-2-oxopiperazine as a gum (0.41 g).

A mixture of the material so obtained, trifluoroacetic acid (1.5 ml) and methylene chloride (10 ml) was stirred at ambient temperature for 18 hours. Water (0.5 ml) was added and the mixture was evaporated. There was thus obtained 1-(2-naphthylmethyl)-2-oxopiperazine trifluoroacetate salt (0.4 g) which was used without further purification;

NMR Spectrum (CD$_3$SOCD$_3$) 3.4–3.5 (m, 4H), 3.9 (s, 2H), 4.8 (s, 2H), 7.4–7.6 (m, 3H), 7.8–8.0 (m, 4H).

EXAMPLE 47

Using an analogous procedure to that described in Example 20, 2-[2-(2-naphthalenesulphonamido)acetamido]-3-[1-(4-pyridyl)piperidin-4-ylcarbonylamino]propionic acid was reacted with 4-methylpiperidine to give N-{1-(4-methylpiperidin-1-ylcarbonyl)-2-[1-(4-pyridyl)piperidin-4-ylcarbonylamino]ethyl}-2-(2-naphthalenesulphonamido)acetamide in 22% yield.

EXAMPLE 48

Using an analogous procedure to that described in Example 20, 2-[2-(2-naphthalenesulphonamido)acetamido]-3-[1-(4-pyridyl)piperidin-4-ylcarbonylamino]propionic acid was reacted with morpholine to give N-{1-morpholinocarbonyl-2-[1-(4-pyridyl)piperidin-4-ylcarbonylamino]-ethyl}-2-(2-naphthalenesulphonamido)acetamide in 36% yield.

EXAMPLE 49

Using an analogous procedure to that described in Example 1, 1-(4-pyridyl)piperidine-4-carbonyl chloride was reacted with 1-(2-naphthylsulphonyl)-1,4-diazepane to give 1-(2-naphthylsulphonyl)-4-[1-(4-pyridyl)piperidin-4-ylcarbonyl]-1,4-diazepane in 42% yield, m.p. 178–180° C.;

NMR Spectrum (CD$_3$SOCD$_3$+CD$_3$CO$_2$D) 1.5–2.0 (m, 6H), 3.15 (m, 1H), 3.3–3.6 (m, 5H), 3.65 (m, 2H), 3.75 (m, 2H), 3.85 (m, 1H), 4.28 (m, 2H), 7.25 (m, 1H), 7.75–8.0 (m, 3H), 8.15–8.4 (m, 5H), 8.6 (d, 1H);

Elemental Analysis Found C, 64.5; H, 6.2; N, 11.8; C$_{26}$H$_{30}$N$_4$O$_3$S 0.25H$_2$O requires C, 64.6; H, 6.3; N, 11.6%.

The 1-(2-naphthylsulphonyl)-1,4-diazepane used as a starting material was obtained as follows:

A solution of 2-naphthylsulphonyl chloride (2.26 g) in methylene chloride (5 ml) was added to a stirred solution of 1,4-diazepane (otherwise known as homopiperazine, 5 g) in methylene chloride (50 ml) which had been cooled to 5° C. The mixture was stirred at ambient temperature for 2 hours. The mixture was partitioned between ethyl acetate and 2N aqueous hydrochloric acid. The aqueous layer was basified to pH13 by the addition of 10N aqueous sodium hydroxide solution and extracted with ethyl acetate. The organic phase was washed with water, dried (MgSO$_4$) and evaporated to give the required starting material in 96% yield;

NMR Spectrum (CD$_3$SOCD$_3$) 1.6–1.75 (m, 2H), 2.6–2.8 (m, 4H), 3.2–3.4 (m, 4H), 7.6–7.9 (m, 3H), 8.0–8.3 (m, 3H), 8.5 (s, 1H).

EXAMPLE 50

A mixture of 1-(4-pyridyl)piperazine (0.136 g), 2,4,5-trichlorophenyl 4-(2-naphthylsulphonyl)piperazine-1-carboxylate (0.2 g) and DMF (2 ml) was stirred and heated to 80° C. for 24 hours. The mixture was cooled to ambient temperature and partitioned between ethyl acetate and water.

The organic phase was washed with brine, dried (MgSO$_4$) and evaporated. The residue was purified by column chromatography using a 19:1 mixture of methylene chloride and methanol as eluent. The oil so obtained was triturated under diethyl ether. There was thus obtained 1-(2-naphthylsulphonyl)-4-[4-(4-pyridyl)-piperazin-1-ylcarbonyl]piperazine (0.139 g, 73%), m.p. 210–212° C.;

NMR Spectrum (CD$_3$SOCD$_3$) 2.9–3.05 (m, 4H), 3.1–3.4 (m, 12H), 6.7 (d, 2H), 7.7 (m, 3H), 8.1–8.3 (m, 5H), 8.45 (s, 1H);

Elemental Analysis Found C, 61.4; H, 6.0; N, 14.7; C$_{24}$H$_{27}$N$_5$O$_3$S requires C, 61.9; H, 5.9; N, 15.0%.

The 2,4,5-trichlorophenyl 4-(2-naphthylsulphonyl)piperazine-1-carboxylate used as a starting material was obtained as follows:

2,4,5-Trichlorophenyl chloroformate (0.26 g) was added dropwise to a stirred mixture of 1-(2-naphthylsulphonyl)piperazine hydrochloride salt (0.63 g), triethylamine (0.41 g) and methylene chloride (10 ml). The mixture was stirred at ambient temperature for 18 hours. The mixture was partitioned between ethyl acetate and 2N aqueous hydrochloric acid. The organic phase was washed with water and with brine, dried (MgSO$_4$) and evaporated. The residue was purified by column chromatography using a 1:1 mixture of hexane and methylene chloride as eluent. There was thus obtained the required starting material (0.32 g);

NMR Spectrum (CD$_3$SOCD$_3$) 3.0–3.2 (m, 4H), 3.5–3.8 (m, 4H), 7.65–7.8 (m, 4H), 7.9 (s, 1H), 8.05 (m, 1H), 8.2 (m, 2H), 8.45 (s, 1H).

The 1-(2-naphthylsulphonyl)piperazine hydrochloride salt used as a starting material was obtained as follows:

A solution of 2-naphthylsulphonyl chloride (6.12 g) in methylene chloride (20 ml) was added dropwise to a stirred mixture of 1-tert-butoxycarbonylpiperazine (5 g), triethylamine (5.63 ml) and methylene chloride (50 ml) which had been cooled in an ice-bath. The mixture was stirred at 5° to 10° C. for 4 hours. The mixture was partitioned between ethyl acetate and 1M aqueous citric acid solution. The organic phase was washed with water and with brine, dried (MgSO$_4$) and evaporated. There was thus obtained 1-(tert-butoxycarbonyl)-4-(2-naphthylsulphonyl)piperazine as a solid (4.84 g), m.p. 174–176° C.

A portion (0.25 g) of the material so obtained as suspended in ethyl acetate (20 ml) and the mixture was cooled in an ice-bath. Hydrogen chloride gas was led into the mixture for 20 minutes. The mixture was evaporated. There was thus obtained 1-(2-naphthylsulphonyl)piperazine hydrochloride salt (0.21 g);

NMR Spectrum (CD$_3$SOCD$_3$) 3.1–3.3 (m, 8H), 7.7–7.85 (m, 3H), 8.1 (d, 1H), 8.15–8.2 (m, 2H), 8.5 (s, 1H), 9.2–9.4 (s, 1H).

EXAMPLE 51

Using an analogous procedure to that described in Example 1, 1-(4-pyridyl)piperidine-4-carbonyl chloride was reacted with (2RS,5SR)-2,5-dimethyl-1-(2-naphthylsulphonyl)piperazine to give (2RS,5SR)-2,5-dimethyl-1-(2-naphthylsulphanyl)-4-[1-(4-pyridyl)-piperidin-4-ylcarbonyl)piperazine in 13% yield;

NMR Spectrum (CDCl$_3$) 0.85–1.03 (m, 3H), 1.1–1.4 (m, 2H), 1.65–2.1 (m, 4H), 2.65 (m, 1H), 2.90 (m, 2H), 3.18 (m, 1H), 3.58 (m, 2H), 3.89 (m, 2H), 4.25 (m, 2H), 6.62 (d, 2H), 7.7 (m, 3H), 7.95 (m, 3H), 8.25 (d, 2H), 8.39 (s, 1H);

Elemental Analysis Found C, 58.7; H, 6.2; N, 9.5; C$_{27}$H$_{32}$N$_4$O$_3$S 0.9CH$_2$Cl$_2$ requires C, 58.5; H, 6.0; N, 9.8%.

The (2RS,5SR)-2,5-dimethyl-1-(2-naphthylsulphonyl)piperazine used as a starting material was obtained in 50% yield by the reaction of (2RS,5SR)-2,5-dimethylpiperazine and 2-naphthylsulphonyl chloride using an analogous procedure to that described in Example 2.

EXAMPLE 52

Using an analogous procedure to that described in Example 1, 1-(4-pyridyl)piperidine-4-carbonyl chloride was reacted with 3-methyl-1-(2-naphthylsulphonyl)piperazine to give 3-methyl-1-(2-naphthylsulphonyl)-4-[1-(4-pyridyl)piperidin-4-ylcarbonyl]piperazine in 32% yield;

NMR Spectrum (CD$_3$SOCD$_3$, 100° C.) 1.5–1.75 (m, 4H), 2.45–2.7 (m, 3H), 3.19 (m, 1H), 3.57 (m, 1H), 3.75 (m, 3H), 4.06 (d, 1H), 4.52 (m, 1H), 6.65 (d, 2H), 7.6–7.79 (m, 3H), 8.0–8.15 (m, 5H), 8.38 (s, 1H);

Elemental Analysis Found C, 64.1; H, 6.4; N, 11.3; C$_{26}$H$_{30}$N$_4$O$_3$S 0.25 EtOAc 0.15H$_2$O requires C, 64.4; H, 6.47; N, 11.1%.

The 3-methyl-1-(2-naphthylsulphonyl)piperazine used as a starting material was obtained in quantitative yield by the reaction of 2-methylpiperazine and 2-naphthylsulphonyl chloride using an analogous procedure to that described in Example 2.

EXAMPLE 53

Using an analogous procedure to that described in Example 2, 3-methyl-1-[1-(4-pyridyl)piperidin-4-ylcarbonyl]piperazine was reacted with 2-naphthylsulphonyl chloride. The reaction mixture was evaporated and the residue was partitioned between ethyl acetate and 2N aqueous hydrochloric acid. The aqueous layer was basified to pH14 by the addition of 10N aqueous sodium hydroxide solution and extracted with ethyl acetate. The organic phase was dried (MgSO$_4$) and evaporated. There was thus obtained 2-methyl-1-(2-naphthylsulphonyl)-4-[1-(4-pyridyl)piperidin-4-ylcarbonyl]piperazine in 96% yield;

NMR Spectrum (CD$_3$SOCD$_3$, 100° C.) 1.5–1.75 (m, 4H), 2.75–3.3 (m, 6H), 3.6–4.2 (m, 6H), 6.7 (d, 2H), 7.61–7.84 (m, 3H), 8.0–8.16 (m, 5H), 8.45 (s, 1H);

Elemental Analysis Found C, 63.2; H, 6.5; N, 11.1; C$_{26}$H$_{30}$N$_4$O$_3$S 0.8H$_2$O requires C, 63.2; H, 6.5; N, 11.3%.

The 3-methyl-1-1-(4-pyridyl)piperidin-4-ylcarbonyl]-piperazine used as a starting material was obtained in 39% yield by the reaction of 1-(4-pyridyl)piperidine-4-carbonyl chloride and 2-methylpiperazine using an analogous procedure to that described in Example 1.

EXAMPLE 54

Using an analogous procedure to that described in Example 1, 1-(4-pyridyl)piperidine-4-carbonyl chloride was reacted with 1-[(E)-4-chlorostyrylsulphonyl]-3-methylpiperazine. The reaction mixture was evaporated and the residue was partitioned between ethyl acetate and 2N aqueous hydrochloric acid. The aqueous layer was basified to pH14 by the addition of 10N aqueous sodium hydroxide solution and extracted with ethyl acetate. The organic phase was dried (MgSO$_4$) and evaporated. The residue was purified by column chromatography using increasingly polar mixtures of ethyl acetate and methanol as eluent. There was thus obtained 4-[(E)-4-chlorostyrylsulphonyl]-2-methyl-1-[1-(4-pyridyl)piperidin-4-ylcarbonyl]piperazine in 24% yield;

NMR Spectrum (CD$_3$SOCD$_3$, 100° C.) 1.24 (d, 3H), 1.6–1.8 (m, 4H), 2.7 to 3.05 (m, 5H), 3.22 (m, 1H), 3.45 (m, 1H), 3.62 (m, 1H), 3.84 (m, 2H), 4.12 (m, 1H), 4.6 (m, 1H), 6.71 (d, 2H), 7.14 (d, 1H), 7.42 (d, 1H), 7.4–7.7 (m, 4H), 8.15 (d, 2H);

Elemental Analysis Found C, 57.6; H, 6.2; N, 10.5; $C_{24}H_{29}ClN_4O_3$ 0.5EtOAc 0.5$H_2O$ requires C, 57.6; H, 6.3; N, 10.3%.

The 1-[(E)-4-chlorostyrylsulphonyl]-3-methylpiperazine used as a starting material was obtained in 35% yield by the reaction of 2-methylpiperazine and (E)-4-chlorostyrylsulphonyl chloride using an analogous procedure to that described in Example 2.

EXAMPLE 55

A mixture of 4-chloropyrimidine hydrochloride (0.151 g), 1-(2-naphthylsulphonyl)-4-(4-piperidinylcarbonyl)piperazine (0.387 g), triethylamine (0.202 g) and ethanol (5 ml) was stirred and heated to reflux for 1 hour. The mixture was evaporated and the residue was purified by column chromatography using a 19:1 mixture of methylene chloride and methanol as eluent. The solid so obtained was recrystallised from acetonitrile. There was thus obtained 1-(2-naphthylsulphonyl)-4-[1-(4-pyrimidinyl)piperidin-4-ylcarbonyl]piperazine (0.135 g, 29%), m.p. 203–205° C.;

NMR Spectrum ($CD_3SOCD_3$) 1.38 (m, 2H), 1.63 (m, 2H), 2.8–3.1 (m, 7H), 3.5–3.8 (m, 4H), 4.3 (m, 2H), 6.75 (d, 1H), 7.7–7.85 (m, 3H), 8.05–8.3 (m, 4H), 8.45 (m, 2H);

Elemental Analysis Found C, 61.4; H, 5.9; N, 15.1; $C_{24}H_{27}N_5O_3S$ 0.2$H_2O$ requires C, 61.5; H, 5.85; N, 14.9%.

The 1-(2-naphthylsulphonyl)-4-(4-piperidinylcarbonyl)piperazine used as a starting material was obtained as follows:

A solution of di-tert-butyl dicarbonate (10.9 g) in methylene chloride (50 ml) was added dropwise to a stirred mixture of ethyl piperidine-4-carboxylate (7.85 g), triethylamine (10.1 g) and methylene chloride (100 ml) which was cooled in an ice-bath to a temperature in the range 5 to 10° C. The mixture was stirred at 5° C. for 1 hour. The mixture was evaporated and the residue was partitioned between diethyl ether and a 1M aqueous citric acid solution. The organic phase was washed with water and with brine, dried ($MgSO_4$) and evaporated. There was thus obtained ethyl 1-tert-butoxycarbonylpiperidine-4-carboxylate as an oil.

A mixture of the material so obtained, 2N aqueous sodium hydroxide solution (50 ml) and methanol (125 ml) was stirred at ambient temperature for 1 hour. The mixture was concentrated by evaporation of the bulk of the methanol and the residue was partitioned between diethyl ether and 1H aqueous citric acid solution. The organic phase was washed with water and with brine, dried ($MgSO_4$) and evaporated. There was thus obtained 1-tert-butoxycarbonylpiperidine-4-carboxylic acid (10.6 g, 92%).

N-(3-Dimethylaminopropyl)-N'-ethylcarbodiimide (2.5 g) was added to a stirred mixture of 1-(2-naphthylsulphonyl)piperazine [3.61 g; obtained by partitioning the corresponding piperazine hydrochloride salt between diethyl ether and 10N aqueous sodium hydroxide solution and drying ($MgSO_4$) and evaporating the organic phase], 1-tert-butoxycarbonylpiperidine-4-carboxylic acid (3 g) and DHF (40 ml) which had been cooled in an ice-bath. The mixture was stirred at ambient temperature for 18 hours. The mixture was partitioned between ethyl acetate and water. The organic phase was washed with water and with brine, dried ($MgSO_4$) and evaporated. The residue was purified by column chromatography using ethyl acetate as eluent. There was thus obtained 1-(2-naphthylsulphonyl)-4-(1-tert-butoxycarbonylpiperidin-4-ylcarbonyl)piperazine (3.79 g, 59%), m.p. 195–197° C.

A mixture of a portion (1 g) of the material so obtained and trifluoroacetic acid (5 ml) was stirred at ambient temperature for 2 hours. The mixture was partitioned between methylene chloride and 2N aqueous sodium hydroxide solution. The organic phase was washed with water, dried ($MgSO_4$) and evaporated. There was thus obtained 1-(2-naphthylsulphonyl)-4-(4-piperidinylcarbonyl)piperazine (0.61 g, 77%);

NMR Spectrum ($CD_3SOCD_3$) 1.2–1.5 (m, 4H), 2.4–2.7 (m, 3H), 2.8–3.1 (m, 6H), 3.5–3.7 (m, 4H), 7.6–7.8 (m, 3H), 8.0–8.3 (m, 3H), 8.4 (s, 1H).

EXAMPLE 56

A mixture of 2-amino-4-chloro-6-methylpyrimidine (0.143 g), 1-(2-naphthylsulphonyl)-4-(4-piperidinylcarbonyl)piperazine (0.387 g), triethylamine (0.101 g) and ethanol (5 ml) was stirred and heated to reflux for 18 hours. The mixture was cooled to ambient temperature and partitioned between ethyl acetate and water. The organic phase was washed with water, dried ($MgSO_4$) and evaporated. The residue was triturated under diethyl ether. There was thus obtained 4-[1-(2-amino-6-methylpyrimidin-4-yl)piperidin-4-ylcarbonyl]-1-(2-naphthylsulphonyl)piperazine (0.29 g, 58%);

NMR Spectrum ($CD_3SOCD_3$) 1.2–1.45 (m, 2H), 1.55 (m, 2H), 2.05 (s, 3H), 2.8 (m, 3N), 2.9–3.2 (m, 4H), 3.5–3.7 (m, 4H), 4.23 (m, 2H), 5.95 (d, 3H), 7.7–7.85 (m, 3H), 8.2 (m, 3H), 8.45 (s, 1H);

Elemental Analysis Found C, 60.1; H, 6.4; N, 16.6; $C_{25}H_{30}N_6O_3S$ 0.3$H_2O$ requires C, 60.1; H, 6.1; N, 16.8%.

EXAMPLE 57

A mixture of succinimido 1-(4-pyrimidinyl)piperidine-4-carboxylate (0.326 g), 1-[(E)-4-chlorostyrylsulphonyl]piperazine (0.4 g) and DMF (5 ml) was stirred at ambient temperature for 16 hours. The mixture was partitioned between ethyl acetate and water. The organic phase was washed with water, dried ($MgSO_4$) and evaporated. The residue was purified by column chromatography using a 49.1 mixture of methylene chloride and methanol as eluent. The material so obtained was recrystallised from acetonitrile. There was thus obtained 1-[(E)-4-chlorostyrylsulphonyl]-4-[1-(4-pyrimidinyl)piperidin-4-ylcarbonyl]piperazine (0.133 g, 22%), m.p. 209–210° C.;

NMR Spectrum ($CD_3SOCD_3$) 1.3–1.6 (m, 2H), 1.7 (m, 2H), 2.9–3.2 (m, 7H), 3.5–3.8 (m, 4H), 4.4 (m, 2H), 6.8 (d, 1H), 7.4 (m, 4H), 7.8 (d, 2H), 8.15 (d, 1H), 8.45 (s, 1H);

Elemental Analysis Found C, 55.2; H, 5.5; N, 14.7; $C_{22}H_{26}ClN_5O_3S$ requires C, 55.5; H, 5.5; N, 14.7%.

The succinimido 1-(4-pyrimidinyl)piperidine-4-carboxylate used as a starting material was obtained as follows:

Using an analogous procedure to that described in Example 32, 4-chloropyrimidine hydrochloride was reacted with ethyl piperidine-4-carboxylate to give ethyl 1-(4-pyrimidinyl)piperidine-4-carboxylate in 46% yield.

A mixture of the material so obtained (0.5 g), 2N aqueous hydrochloric acid (5 ml) and THF (15 ml) was stirred and heated to reflux for 18 hours. The mixture was evaporated and the residue was washed with ethyl acetate. There was thus obtained 1-(4-pyrimidinyl)piperidine-4-carboxylic acid hydrochloride salt (0.49 g, 95%);

NMR Spectrum ($CD_3SOCD_3$) 1.6 (m, 2H), 2.0 (m, 2H), 2.7 (m, 1H), 3.4 (m, 2H), 4.5 (broad s, 2H), 7.2 (d, 1H), 8.3 (d, 1H), 8.8 (s, 1H).

A mixture of the acid so obtained, N-hydroxysuccinimide (0.29 g), triethylamine (0.61 g), N-(3-dimethylaminopropyl)-N'-ethylcarbodiimide (0.48 g) and DMSO (10 ml) was stirred at ambient temperature for 5 hours. The mixture was partitioned between ethyl acetate and water. The organic phase was washed with water, dried (MgSO$_4$) and evaporated. There was thus obtained succinimido 1-(4-pyrimidinyl)piperidine-4-carboxylate which was used without further purification.

The 1-[(E)-4-chlorostyrylsulphonyl]piperazine used as a starting material was obtained in 42% yield by the reaction of piperazine and (E)-4-chlorostyrylsulphinyl chloride using an analogous procedure to that described in Example 2.

EXAMPLE 58

Using an analogous procedure to that described in Example 1, 1-(4-pyridyl)piperidine-4-carbonyl chloride was reacted with 1-(4'-methylbiphenyl-4-ylsulphonyl)piperazine to give 1-(4'-methylbiphenyl-4-ylsulphonyl)-4-[1-(4-pyridyl)piperidin-4-ylcarbonyl]piperazine in 67% yield, m.p. 213–217° C.;

NMR Spectrum (CD$_3$SOCD$_3$+CD$_3$CO$_2$D) 1.6–1.85 (m, 4H), 2.35 (s, 3H), 2.98 (m, 1H), 3.05–3.3 (m, 6H), 3.55–3.65 (m, 4H), 3.95 (m, 2H), 6.95 (d, 2H), 7.3 (d, 2H), 7.55 (d, 2H), 7.8 (m, 4H), 8.05 (d, 2H);

Elemental Analysis Found C, 65.0; H, 6.3; N, 10.8; C$_{28}$H$_{32}$N$_4$O$_3$S 0.66H$_2$O requires C, 65.1; H, 6.5; N, 10.8%.

The 1-(4'-methylbiphenyl-4-ylsulphonyl)piperazine used as a starting material was prepared as follows:

A solution of 4-iodophenylsulphonyl chloride (5 g) in methylene chloride (150 ml) was added dropwise to a stirred solution of piperazine (7.1 g) in methylene chloride (50 ml) which had been cooled in an ice bath. The mixture was stirred at ambient temperature for 14 hours. The mixture was extracted with 2N aqueous hydrochloric acid. The aqueous solution was washed with ethyl acetate, basified by the addition of 2N aqueous sodium hydroxide solution and extracted with ethyl acetate. The organic extract was washed with water, dried (MgSO$_4$) and evaporated. There was thus obtained 1-(4-iodophenylsulphonyl)piperazine (4.6 g) which was used without further purification.

A mixture of the material so obtained (0.5 g), 4-tolylboronic acid (0.19 g), 2M aqueous sodium carbonate solution (7.8 ml), tetrakis-(triphenylphosphine)palladium (O) (0.1 g), ethanol (15 ml) and toluene (21 ml) was stirred and heated to reflux for 5 hours. The mixture was cooled to ambient temperature and partitioned between ethyl acetate and water. The organic phase was washed with water, dried (MgSO$_4$) and evaporated. There was thus obtained 1-(4'-methylbiphenyl-4-ylsulphonyl)piperazine (0.43 g);

NMR Spectrum (CD$_3$SOCD$_3$) 2.35 (s, 3H), 2.7–2.9 (m, 8H), 7.35 (d, 2H), 7.65 (d, 2H), 7.8 (d, 2H), 7.95 (d, 2H).

EXAMPLE 59

Using an analogous procedure to that described in Example 1, 1-(4-piperidine-4-carbonyl chloride was reacted with the appropriate 1-(phenylsulphonyl)piperazine. There were thus obtained the compounds disclosed in Table IV, the structures of which were confirmed by NMR spectroscopy. Unless otherwise stated, the appropriate 1-(phenylsulphonyl)piperazine was obtained from 1-(4-iodophenylsulphonyl)piperazine using an analogous procedure to that described in the last paragraph of the portion of Example 58 which is concerned in the preparation of starting materials.

TABLE IV

| Example 59 Compound No. | R | m.p. (° C.) | Yield (%) |
|---|---|---|---|
| 1[a] | 4-(4-bromophenyl) | 203–207 | 54 |
| 2[b] | 4-(3,5-dichlorophenyl) | gum | 13 |
| 3[c] | 3-(4-chlorophenyl) | foam | 12 |
| 4[d] | 3-phenyl | gum | 12 |
| 5[e] | 4-iodo | glass | 79 |
| 6[f] | 4-(4-ethoxycarbonylphenyl) | gum | 5 |
| 7[g] | 4-(4-cyanophenyl) | gum | 3 |
| 8[h] | 3-(3,5-dichlorophenyl) | gum | 18 |
| 9[i] | 4-(4-nitrophenyl) | gum | 27 |
| 10[j] | 4-(4-chloro-2-nitrophenyl) | gum | 19 |

Notes a. The product gave the following NMR signals (CD$_3$SOCD$_3$+CD$_3$CO$_2$D) 1.6–1.85 (m, 4H), 2.98 (m, 1H), 3.05–3.3 (m, 6H), 3.55–3.65 (m, 4H), 3.93 (m, 2H), 6.9 (d, 2H), 7.55–7.65 (m, 4H), 7.8–7.9 (m, 4H), 8.1 (d, 2H).

The 1-(4'-bromobiphenyl-4-ylsulphonyl)piperazine used as a starting material was obtained from 4-bromobiphenyl. That compound was converted into 4'-bromo-4-biphenylylsulphonyl chloride using analogous procedures to those described in Note c below Table III in Example 41. The material so obtained was reacted with piperazine using an analogous procedure to that described in Example 2. The required starting material gave the following NMR signals (CD$_3$SOCD$_3$) 2.7–2.8 (m, 4H), 2.8–2.9 (m, 4H), 7.75 (d, 4H), 7.8 (d, 2H), 7.95 (d, 2H).

b. The product gave the following NMR signals (CD$_3$SOCD$_3$) 1.5–1.75 (m, 4H), 2.8–3.15 (m, 7H), 3.55–3.65 (m, 4H), 3.8 (m, 2H), 6.7 (d, 2H), 7.55 (t, 1H), 7.7 (d, 2H), 7.8–7.95 (m, 4H), 8.1 (d, 2H).

The starting material 1-(3',5'-dichlorobiphenyl-4-ylsulphonyl)piperazine gave the following NMR signals (CD$_3$SOCD$_3$) 2.7–2.8 (m, 4H), 2.8–2.9 (m, 4H), 7.65 (t, 1H), 7.75–7.85 (m, 4H), 8.0 (d, 2H).

c. The product gave the following NMR signals (CD$_3$SOCD$_3$) 1.55–1.75 (m, 4H), 2.7–3.05 (m, 3H), 3.05–3.15 (m, 4H), 3.55–3.6 (m, 4H), 3.6–3.75 (m, 2H), 6.7 (d, 2H), 7.5 (d, 2H), 7.65–7.8 (m, 4H), 7.92 (m, 2H), 8.1 (d, 2H).

The starting material 1-(4'-chlorobiphenyl-3-ylsulphonyl)-piperazine was obtained by the reaction of 1-(3-bromophenylsulphonyl)piperazine (obtained by the reaction of piperazine and 3-bromophenylsulphonyl chloride) and 4-chlorophenylboronic acid using an analogous procedure to that described in the last paragraph of the portion of Example 58 which is concerned with the preparation of starting materials. The required starting material gave the following NMR signals (CD$_3$SOCD$_3$) 2.7–2.8 (m, 4H), 2.8–2.9 (m, 4H), 7.6 (d, 2H), 7.7–7.8 (m, 5H), 8.05 (m, 1H).

d. The product gave the following NMR signals (CD$_3$SOCD$_3$) 1.6–1.8 (m, 4H), 2.98 (m, 1H), 3.1–3.3 (m, 6H), 3.55–3.65 (m, 4H), 3.95 (m, 2H), 6.95 (d, 2H), 7.4–7.55 (m, 3H), 3.65–3.8 (m, 4H), 7.92 (m, 2H), 8.1 (d, 2H).

e. The product gave the following NMR signals (CD$_3$SOCD$_3$) 1.41–1.64 (m, 4H), 2.82–2.91 (m, 7H), 3.54–3.62 (m, 4H), 3.89 (d, 2H), 6.78 (d, 2H), 7.49 (d, 2H), 8.02 (d, 2H), 8.10 (d, 2H).

f. The product gave the following NMR signals ($CD_3SOCD_3$) 1.28–1.68 (m, 7H), 2.76–3.07 (m, 7H), 3.49–3.75 (m, 4H), 3.8–4.07 (d, 2H), 4.42–4.43 (m, 2H), 6.76 (d, 2H), 7.8–8.2 (m, 10H).

The starting material 1-(4'-ethoxycarbonylbiphenyl-4-ylsulphonyl)piperazine was obtained as follows:

A mixture of 1-(4-iodophenylsulphonyl)piperazine (5 g), bis(tributyltin) (11 ml), tetrakis(triphenylphosphine) palladiun(O) (0.16 g) and toluene (200 ml) was stirred and heated to 120° C. for 36 hours. The mixture was cooled to ambient temperature and filtered. The filtrate was evaporated and the residue was purified by column chromatography using increasingly polar mixtures of methylene chloride and methanol as eluent. The material so obtained was dissolved in a mixture of methylene chloride (20 ml), methanol (5 ml) and water (0.2 ml). Potassium fluoride (3 g) was added and the mixture was stirred at ambient temperature for 1 hour. The mixture was partitioned between methylene chloride and water. The organic phase was washed with water, dried ($MgSO_4$) and evaporated. There was thus obtained [4-(piperazin-1-ylsulphonyl)phenyl]tributyltin (1.5 g).

A mixture of the material so obtained, ethyl 4-iodobenzoate (1.6 g), tetrakis(triphenylphosphine)palladium(O) (0.034 g) and toluene (50 ml) was stirred and heated to reflux for 72 hours. The mixture was evaporated and the solid residue was washed with a 97:3 mixture of methylene chloride and methanol. There was thus obtained 1-(4'-ethoxycarbonylbiphenyl-4-ylsulphonyl)piperazine (0.76 g);

NMR Spectrum ($CD_3SOCD_3$) 1.3–1.43 (t, 3H), 3.07–3.37 (d, 8H), 4.27–4.44 (m, 2H), 7.65–7.97 (m, 4H), 7.97–8.15 (m, 4H).

g. The product gave the following NMR signals ($CD_3SOCD_3$, 100° C.) 1.57–1.78 (m, 4H), 2.79–3.08 (m, 3H), 3.08–3.18 (t, 4H), 3.55–3.68 (t, 4H), 3.75–3.82 (t, 1H), 3.85 (t, 1H), 6.74 (d, 2H), 7.85–8.02 (m, 8H), 8.14 (m, 2H).

The 1-(4'-cyanobiphenyl-4-ylsulphonyl)piperazine used as a starting material was obtained by the reaction of [4-(piperazin-1-ylsulphonyl)phenyl]tributyltin and 4-iodobenzonitrile using an analogous procedure to that described in Note f immediately above.

h. The product gave the following NMR signals ($CD_3SOCD_3$, 100° C.) 1.53–1.8 (m, 4H), 2.65–3.08 (m, 3H), 3.08–3.20 (t, 4H), 3.54–3.65 (t, 4H), 3.84 (t, 1H), 3.90 (t, 1H), 6.75–6.85 (d, 2H), 7.58 (t, 1H), 7.7–7.9 (m, 4H), 7.95–8.08 (m, 2H), 8.08–8.18 (m, 2H).

The 1-(3',5'-dichlorobiphenyl-3-ylsulphonyl)piperazine used as a starting material was obtained as follows:

Using analogous procedures to those described in the portion of Example 58 which is concerned with the preparation of starting materials, piperazine was reacted with 3-bromophenylsulphonyl chloride to give 1-(3-bromophenylsulphonyl)piperazine which, in turn, was reacted with 3,5-dichlorophenylboronic acid to give 1-(3',5'-dichlorobiphenyl-3-ylsulphonyl)piperazine in 29% yield;

NMR Spectrum ($CD_3SOCD_3$, 100° C.) 2.7–2.85 (m, 4H), 2.95–3.05 (m, 4H), 7.58 (t, 1H), 7.68–7.85 (m, 4H), 7.91–8.05 (m, 2H).

i. The product gave the following NMR signals ($CD_3SOCD_3$; 100° C.) 1.5–1.75 (m, 4H), 2.75–3.04 (m, 5H), 3.05–3.17 (t, 4H), 3.53–3.65 (t, 4H), 3.75 (t, 1H), 3.81 (t, 1H), 6.69 (d, 2H), 7.88 (d, 2H), 7.93–8.04 (d, 4H), 8.1 (d, 2H), 8.3 (d, 2H).

The 1-(4'-nitrobiphenyl-4-ylsulphonyl)piperazine used as a starting material was obtained by the reaction of [4-(piperazin-1-ylsulphonyl)phenyl]tributyltin and 1-iodo-4-nitrobenzene using an analogous procedure to that described in Note f immediately above.

j. The product gave the following NMR signals ($CD_3SOCD_3$; 100° C.) 1.53–1.77 (m, 4H), 2.61–3.06 (m, 3H), 3.11 (t, 4H), 3.58 (t, 4H), 3.75 (t, 1H), 3.86 (t, 1H), 6.73 (d, 2H), 7.58 (d, 3H), 7.82 (m, 4H), 8.12 (d, 2H).

The 1-(4'-chloro-2'-nitrobiphenyl-4-ylsulphonyl)piperazine used as a starting material was obtained by the reaction of [4-(piperazin-1-ylsulphonyl)phenyl]tributyltin and 2-bromo-5-chloro-1-nitrobenzene using an analogous procedure to that described in Note f immediately above.

EXAMPLE 60

Using an analogous procedure to that described in Example 1, 1-(4-pyridyl)piperidine-4-carbonyl chloride was reacted with 1-[4-(2-pyridyl)phenylsulphonyl]piperazine to give 1-[4-(2-pyridyl)phenylsulphonyl]-4-[1-(4-pyridyl)piperidin-4-ylcarbonyl]piperazine in 54% yield, m.p. 224–226° C.;

NMR Spectrum ($CD_3SOCD_3$) 1.35–1.65 (m, 4H), 2.75–3.05 (m, 7H), 3.5–3.7 (m, 4H), 3.88 (m, 2H), 6.75 (d, 2H), 7.45 (m, 1H), 7.8–8.0 (m, 3H), 8.05–8.15 (m, 3H), 8.35 (d, 2H), 8.72 (m, 1H);

Elemental Analysis Found C, 62.7; H, 5.9; N, 14.0; $C_{26}H_{29}N_5O_3S$ $0.5H_2O$ requires C, 62.4; H, 6.0; N, 14.0%.

The 1-[4-(2-pyridyl)phenylsulphonyl]piperazine used as a starting material was obtained as follows:

A mixture of 1-(4-iodophenylsulphonyl)piperazine (0.48 g), (2-pyridyl)tributyltin (1.18 g), tetrakis(triphenylphosphine)-palladium(O) (0.1 g) and toluene (15 ml) was stirred and heated to reflux for 18 hours. The mixture was evaporated and the residue was purified by column chromatography using increasingly polar mixtures of methylene chloride and methanol as eluent. There was thus obtained 1-[4-(2-pyridyl)phenylsulphonyl]piperazine (0.439 g);

NMR Spectrum ($CD_3SOCD_3$) 2.65–2.8 (m, 4H), 2.8–2.9 (m, 4H), 7.45 (m, 1H), 7.8–8.1 (m, 3H), 8.35 (d, 2H), 8.73 (m, 1H).

EXAMPLE 61

A mixture of 2-ethoxycarbonyl-4-(2-naphthylsulphonyl)-1-[1-(4-pyridyl)piperidin-4-ylcarbonyl]piperazine (0.67 g), 2N aqueous sodium hydroxide solution (2.5 ml) and methanol (10 ml) was stirred at ambient temperature for 3 hours. The mixture was evaporated and the residue was dissolved in water (10 ml). The solution was acidified by the addition of acetic acid. The precipitate was isolated and dried. There was thus obtained 2-carboxy-4-(2-naphthylsulphonyl)-1-[1-(4-pyridyl)piperidin-4-ylcarbonyl]piperazine (0.47 g), m.p. 225°–228° C. (decomposes);

NMR Spectrum ($CD_3SOCD_3$+$CD_3CO_2D$, 100° C.) 1.55–1.9 (m, 4H), 2.45–2.55 (m, 1H), 2.65–2.75 (m, 1H), 2.9–3.05 (m, 1H), 3.1–3.4 (m, 3H), 3.7 (m, 1H), 3.92 (m, 2H), 4.07 (m, 1H), 4.25 (m, 1H), 4.98 (m, 1H), 6.9 (d, 2H), 7.6–7.8 (m, 3H), 7.95–8.2 (m, 5H), 8.4 (d, 1H).

Elemental Analysis Found C, 58.4; H, 5.8; N, 10.3; $C_{26}H_{28}N_4O_5S$ $1.5H_2O$ requires C, 58.3; H, 5.8; N, 10.45%.

EXAMPLE 62

Using an analogous procedure to that described in Example 1, 1-(4-pyridyl)piperidine-4-carbonyl chloride was reacted with ethyl 1-(6-chloronaphth-2-ylsulphonyl) piperazine-3-carboxylate to give 4-(6-chloronaphth-2-ylsulphonyl)-2-ethoxycarbonyl-1-[1-(4-pyridyl)-piperidin-4-ylcarbonyl]piperazine in 37% yield;

NMR Spectrum ($CD_3SOCD_3$, 100° C.) 1.2 (t, 3H), 1.5–1.8 (m, 4H), 2.6 (m, 1H), 2.8 (m, 1H), 2.85–3.05 (m, 4H), 3.65–3.85 (m, 3H), 4.05–4.25 (m, 4H), 5.1 (m, 1H), 6.7 (d, 2H), 7.65 (m, 1H), 7.8 (m, 1H), 8.1–8.25 (m, 5H), 8.45 (d, 1H);

Elemental Analysis Found C, 58.5; H, 5.6; N, 9.6; $C_{28}H_{31}ClN_4O_5S$ requires C, 58.9; H, 5.5; N, 9.8%.

The ethyl 1-(6-chloronaphth-2-ylsulphonyl)piperazine-3-carboxylate used as a starting material was obtained in 78% yield from ethyl 1-benzylpiperazine-2-carboxylate and 6-chloronaphth-2-ylsulphonyl chloride using analogous procedures to those described in the portion of Example 44 which is concerned with the preparation of starting materials.

EXAMPLE 63

Using an analogous procedure to that described in Example 61, 4-(6-chloronaphth-2-ylsulphonyl)-2-ethoxycarbonyl-1-[1-(4-pyridyl)-piperidin-4-ylcarbonyl]piperazine was hydrolysed to give 2-carboxy-4-(6-chloronaphth-2-ylsulphonyl)1-[1-(4-pyridyl)piperidin-4-ylcarbonyl]-piperazine in 90% yield, m.p. 215–220° C. (decomposes);

NMR Spectrum ($CD_3SOCD_3$, 100° C.) 1.5–1.8 (m, 4H), 2.7–3.05 (m, 5H), 3.6–3.85 (m, 4H), 4.1 (m, 1H), 4.25 (m, 1H), 4.95 (m, 1H), 6.7 (d, 2H), 7.65 (m, 1H), 7.8 (m, 1H), 8.05–8.25 (m, 5H), 8.45 (d, 1H);

Elemental Analysis Found C, 56.7; H, 5.0; N, 9.9; $C_{26}H_{27}ClN_4O_5S$ $0.5H2O$ requires C, 56.6; H, 5.1; N, 10.15%.

EXAMPLE 64

A mixture of 2-carboxy-4-(2-naphthylsulphonyl)-1-[1-(4-pyridyl)piperidin-4-ylcarbonyl]piperazine (0.11 g), piperidine (0.064 ml), N-hydroxybenzotriazole (0.029 g), N,N-dicyclohexylcarbodiimide (0.054 g), DHF (2 ml) and DMSO (2 ml) was stirred at ambient temperature for 18 hours. The mixture was partitioned between methylene chloride and water. The organic phase was dried ($MgSO_4$) and evaporated. The residue was purified by column chromatography using increasingly polar mixtures of methylene chloride and methanol as eluent. There was thus obtained 4-(2-naphthylsulphonyl)-2-piperidinocarbonyl-1-[1-(4-pyridyl)piperidin-4-ylcarbonyl]piperazine as a glass (0.063 g);

NMR Spectrum ($CD_3SOCD_3+CD_3CO_2D$, 100° C.) 1.2–1.8 (m, 10H), 2.7–3.05 (m, 3H), 3.12 (m, 2H), 3.25–3.4 (m, 5H), 3.65 (m, 1H), 3.75–4.0 (m, 4H), 5.2 (m, 1H), 6.85 (d, 2H), 7.6–7.75 (m, 3H), 7.95–8.1 (m, 5H), 8.35 (d, 1H);

Elemental Analysis Found C, 63.6; H, 7.0; N, 12.0; $C_{31}H_{37}N_5O_4S$ $0.5H_2O$ requires C, 63.7; H, 6.5; N, 12.0%.

EXAMPLE 65

A mixture of 1-(2-naphthylsulphonyl)-4-[1-(4-pyridyl)-piperidin-4-ylcarbonyl]piperazine-2-carboxylic acid (0.121 g) and thionyl chloride (0.2 ml) was stirred at ambient temperature for 1 hour. The mixture was evaporated and methylene chloride (8 ml) and piperidine (0.23 ml) were added in turn to the residue. The mixture was stirred at ambient temperature for 2 hours. The mixture was partitioned between methylene chloride and water. The organic phase was dried ($MgSO_4$) and evaporated. The residue was purified by column chromatography using increasingly polar mixtures of methylene chloride and methanol as eluent. There was thus obtained 1-(2-naphthylsulphonyl)-2-piperidinocarbonyl-4-[(4-pyridyl)piperidin 4-ylcarbonyle piperazine as a glass (0.061 g);

NMR Spectrum ($CD_3SOCD_3+CD_3CO_2D$) 1.2–1.8 (m, 10H), 2.9–3.3 (m, 6H), 3.45–3.75 (m, 4H), 3.9–4.2 (m, 4H), 4.47 (m, 1H), 5.0 (m, 1H), 6.8 (d, 2H), 7.68 (m, 3H), 8.0–8.2 (m, 5H), 8.35 (d, 1H);

Elemental Analysis Found C, 62.5; H, 6.4; N, 11.7; $C_{31}H_{37}N_5O_4S$ $H_2O$ requires C, 62.7; H, 6.6; N, 11.8%.

EXAMPLE 66

Using an analogous procedure to that described in Example 1, 1-(4-pyridyl)piperidine-4-carbonyl chloride was reacted with 2-benzyl-1-(2-naphthylsulphonyl)piperazine to give 2-benzyl-1-(2-naphthylsulphonyl)-4-[1-(4-pyridyl) piperidin-4-ylcarbonyl]piperazine in 70% yield; m.p. 186–188° C.;

NMR Spectrum ($CD_3SOCD_3$) 1.6 (m, 4H), 2.7 (m, 3H), 3.0 (m, 4H), 3.9 (m, 4H), 4.2 (d, 2H), 6.6 (d, 3H), 7.2 (d, 5H), 7.7 (m, 3H), 8.1 (m, 5H), 8.5 (s, 1H).

Elemental Analysis Found C, 67.9; H, 6.3; N, 9.8; $C_{32}H_{34}N_4O_3S$ $0.6H_2O$ requires C, 68.0; H, 6.3; N, 9.9%.

The 2-benzyl-1-(2-naphthylsulphonyl)piperazine used as a starting material was obtained as follows:

N-Methylimorpholine (3.12 ml) was added to a stirred mixture of N-tert-butoxycarbonyl-DL-phenylalanine (3 g), N-benzylglycine ethyl ester (2.18 g), N-hydroxybenzotriazole (1.26 g) and DHF (50 ml) which had been cooled to 0° C. The mixture was stirred at 0° C. for 30 minutes and at ambient temperature for 16 hours. The mixture was filtered and the filtrate was evaporated. The residue was partitioned between ethyl acetate and water. The organic phase was washed with water, dried ($MgSO_4$) and evaporated. The residue was purified by column chromatography using a 5:1 mixture of hexane and ethyl acetate as eluent to give a solid (3.7 g).

A mixture of the material so obtained and a 4H solution of hydrogen chloride in diethyl ether was stirred at ambient temperature for 16 hours. The mixture was evaporated to give phenylalanyl-N-benzylglycine ethyl ester (2.65 g);

NMR Spectrum ($CD_3SOCD_3$) 1.2 (m, 2H), 3.1 (t, 2H), 3.6 (m, 4H), 4.1 (m, 2H), 4.6 (m, 2H), 7.2 (m, 10H), 8.4 (s, 2H).

A mixture of a portion (0.5 g) of the material so obtained, N-methylmorpholine (0.15 g) and a 0.1M solution of acetic acid in sec-butanol (25 ml) was stirred and heated to reflux for 3 hours. The mixture was evaporated and the residue was partitioned between methylene chloride and water. The organic phase was washed with water, dried ($MgSO_4$) and evaporated. The residue was purified by column chromatography using increasingly polar mixtures of methylene chloride and methanol as eluent. There was thus obtained 1,3-dibenzyl-2,5-dioxopiperazine (0.29 g), m.p. 173–174° C.

After repetition of the previous reaction, a mixture of 1,3-dibenzyl-2,5-dioxopiperazine (1.6 g), boron trifluoride diethyl ether complex (0.1 g) and THF (5 ml) was stirred and heated to reflux for 15 minutes. The mixture was cooled to ambient temperature and borane dimethyl sulphide complex (0.04 ml) was added dropwise. The mixture was stirred at ambient temperature for 30 minutes. The mixture was evaporated and the residue was heated to 100° C. for 5 minutes. A 6N aqueous hydrochloric acid solution (1 ml)

was added and the mixture was heated to reflux for 1 hour. The mixture was cooled to 0° C. and a 6N aqueous sodium hydroxide solution (1.5 ml) was added. The mixture was partitioned between methylene chloride and a saturated aqueous potassium carbonate solution. The organic phase was washed with water, dried (MgSO$_4$) and evaporated. The residue was purified by column chromatography using increasingly polar mixtures of methylene chloride and methanol as eluent. There was thus obtained 1,3-dibenzylpiperazine (0.29 g).

A solution of the material so obtained in methylene chloride (3 ml) was added dropwise to a stirred mixture of 2-naphthylsulphonyl chloride (0.257 g), triethylamine (0.7 ml) and methylene chloride (5 ml) which had been cooled to 0° C. The mixture was stirred at ambient temperature for 16 hours. The mixture was evaporated and the residue was partitioned between methylene chloride and water. The organic phase was washed with water, dried (MgSO$_4$) and evaporated. The residue was purified by column chromatography using increasingly polar mixtures of methylene chloride and methanol as eluent. There was thus obtained 2,4-dibenzyl-1-(2-naphthylsulphonyl)piperazine (0.37 g);

NMR Spectrum (CD$_3$SOCD$_3$) 1.8 (m, 2H), 2.6 (m, 3H), 3.1 (m, 2H), 3.45 (d, 1H), 3.75 (d, 1H), 4.1 (s, 1H), 6.95 (m, 2H), 7.1 (m, 3H), 7.25 (s, 5H), 7.75 (m, 3H), 8.1 (m, 3H), 8.5 (s, 1H).

A mixture of the material so obtained, 10% palladium-on-carbon catalyst (0.23 g) and methylene chloride (50 ml) was stirred under an atmosphere of hydrogen for 24 hours. The mixture was filtered and the filtrate was evaporated. The residue was purified by column chromatography using a 99:1 mixture of methylene chloride and methanol as eluent. There was thus obtained 2-benzyl-1-(2-naphthylsulphonyl)piperazine (0.08 g).

NMR Spectrum (CD$_3$SOCD$_3$) 2.4–2.8 (m, 4H), 3.1–3.4 (m, 3H), 3.6 (d, 1H), 4.0 (t, 1H), 7.2 (m, 5H), 7.7 (m, 3H), 8.1 (m, 3H), 8.4 (s, 1H).

EXAMPLE 67

Using an analogous procedure to that described in Example 2, 2-amino-N-{1-piperidinocarbonyl-2-[1-(4-pyridyl)piperidin-4-ylcarbonylamino]ethyl}acetamide hydrochloride salt was reacted with (E)-4-chlorostyrylsulphonyl chloride to give 2-[(E)-4-chlorostyrylsulphonamido]-N -[1-piperidinocarbonyl-2-{1-(4-pyridyl)piperidin-4-ylcarbonylamino]ethyl}acetamide as a gum (0.1 g, 16%);

NMR Spectrum (CDCl$_3$) 1.4–2.1 (m, 10H), 2.45 (m, 1H), 2.6–3.1 (m, 2H), 3.4–4.0 (m, 10I), 5.1 (m, 1H), 6.7 (d, 2H), 6.85 (d, 1H), 6.95 (m, 1H), 7.2–7.55 (m, 6H), 7.65 (d, 1H), 8.22 (m, 2H).

EXAMPLE 68

Using an analogous procedure to that described in Example 2, 2-amino-N-{1-piperidinocarbonyl-2-[1-(4-pyridyl)piperidin-4-ylcarbonylamino}ethyl]acetamide hydrochloride salt was reacted with 3,4-dichlorophenylsulphonyl chloride to give 2-(3,4-dichlorophenylsulphonamido)-N-[1-piperidinocarbonyl-2-[1-(4-pyridyl)piperidin-4-ylcarbonylamino ethyl]acetamide as a gum (0.17 g, 27%);

NMR Spectrum (CD$_3$SOCD$_3$) 1.4–1.8 (m, 12H), 2.35 (m, 1H), 2.88 (m, 2H), 3.02 (m, 3 H), 3.15–3.5 (m, 8H), 3.55 (d, 1H), 3.9 (m, 2H), 4.85 (m, 1H), 6.8 (d, 2H), 7.7–7.9 (m, 3H), 8.0 (d, 1H), 8.05 (d, 1H), 8.15 (, 3H);

Elemental Analysis Found C, 49.9; H, 5.4; N, 12.5; C$_{27}$H$_{34}$Cl$_2$N$_6$O$_5$S0.4CH$_2$Cl$_2$ requires C, 49.9; H, 5.2; N, 12.7%.

EXAMPLE 69

Using an analogous procedure to that described in Example 56, 4-chloropyrimidine was reacted with 1-(6-chloronaphth-2-ylsulphonyl)-4-(4-piperidinylcarbonyl) piperazine. The precipitate which was deposited when the reaction mixture was cooled to ambient temperature was isolated and recrystallised from acetonitrile. There was thus obtained 1-(6-chloronaphth-2-ylsulphonyl)-4-[1-(4-pyrimidinyl)-piperidin-4-ylcarbonyl]piperazine in 60% yield, m.p. 218–219° C.;

NMR Spectrum (CD$_3$SOCD) 1.25–1.5 (m, 2H), 1.62 (m, 2H), 2.8–3.1(m 7H), 3.5–3.75 (m, 4H), 4.32 (m, 2H), 6.75 (m, 1H), 7.7 (m, 1H), 7.85 (m, 1H), 8.15 (d, 1H), 8.2 (d, 1H), 8.28 (m, 3H), 8.45 (s, 1H), 8.5 (s, Elemental Analysis Found C, 57.6; H, 5.3; N, 13.9; C$_{24}$H$_{26}$ClN$_5$O$_3$S requires C, 57.7; H, 5.2; N, 14.0%.

The 1-(6-chloronaphth-2-ylsulphonyl)-4-(4-piperidinylcarbonyl)piperazine used as a starting material was obtained as follows:

Using analogous procedures to those described in two of the paragraphs of the portion of Example 50 which is concerned with the preparation of starting materials, 1-tert-butoxycarbonylpiperazine was reacted with 6-chloronaphth-2-ylsulphonyl chloride to give 1-(6-chloronaphth-2-ylsulphonyl)piperazine hydrochloride salt in 58% yield.

The material so obtained was reacted with 1-tert-butoxycarbonylpiperidine-4-carboxylic acid using analogous procedures to those described in the third and fourth paragraphs of the portion of Example 55 which is concerned with the preparation of starting materials. There was thus obtained 1-(6-chloronaphth-2-ylsulphonyl)-4-(4-piperidinylcarbonyl)piperazine in 63% yield;

NMR Spectrum (CDCl$_3$) 1.5–1.75 (m, 4H), 2.4–2.7 (m, 3H), 3.0–3.2 (m, 6H), 3.5–3.75 (m, 4H), 7.55 (m, 1H), 7.75 (m, 1H), 7.95 (m, 3H), 8.3 (s, 1H).

EXAMPLE 70

Using an analogous procedure to that described in Example 56, 2-amino-4-chloropyrimidine was reacted with 1-(6-chloronaphth-2-ylsulphonyl)-4-(4-piperidinylcarbonyl)piperazine. The precipitate which was deposited on cooling the reaction mixture was isolated, washed with cold ethanol and dried. There was thus obtained 4-[1-(2-aminopyrimidin-4-yl)piperidin-4-ylcarbonyl]-1-(6-chloronaphth-2-ylsulphonyl)piperazine in 73% yield, m.p. 265–267° C.;

NMR Spectrum (CD$_3$SOCD$_3$) 1.0–1.4 (m, 4H), 2.5–2.7 (m, 3H), 2.7–2.9 (m, 4H), 3.3–3.5 (m, 4H), 4.08 (m, 2H), 5.7 (s, 2H), 5.8 (d, 1H), 7.5–7.7 (m, 3H), 7.7 5 (d, 1HH, 8.05 (s, 1H), 8.1 (d, 1H), 8.3 (s, 1H);

Elemental Analysis Found C, 55.9; H. 5.4; N. 15.9; C$_{24}$H$_{27}$ClN$_6$O$_3$S requires C, 56.0; H. 5.3; N. 16.3%.

EXAMPLE 71

Using an analogous procedure to that described in Example 32, 3,4,5-trichloropyridazine was reacted with 1-(6-chloronaphth-2-ylsulphonyl)-4-(4-piperidinylcarbonyl)piperazine. The crude reaction product was purified by column chromatography using increasingly polar mixtures of methylene chloride and ethyl acetate as eluent. There was thus obtained 1-(6-chloronaphth-2-ylsulphonyl)-4-1-(3,4-dichloropyridazin-5-yl)piperidin-4-ylcarbonyl]piperazine in 35% yield;

NMR Spectrum ($CD_3SOCD_3$) 1.5–1.7 (m, 4H), 2.7–2.9 (m, 1H), 2.95–3.1 (m, 6H), 3.5–3.85 (m, 6H), 7.7 (m, 2H), 7.85 (m, 1H), 8.15 (d, 1H), 8.22 (s, 1H), 8.25 (d, 1H), 8.5 (s, 1H), 8.9 (s, 1H).

EXAMPLE 72

A mixture of 1-(6-chloronaphth-2-ylsulphonyl)-4-[1-(3,4-dichloropyridazin-5-yl)piperidin-4-ylcarbonyl]piperazine (0.2 g), 10% palladium-on-carbon catalyst (0.05 g) and ethanol (10 ml) was stirred under an atmosphere of hydrogen gas for 48 hours. The mixture was filtered and the filtrate was evaporated. The residue was purified by column chromatography using increasingly polar mixtures of methylene chloride and methanol as eluant. There was thus obtained 1-(6-chloronaphth-2-ylsulphonyl)-4-[1-(4-pyridazinyl)piperidin-4-ylcarbonyl]piperazine (0.045 g, 25%);

NMR Spectrum ($CD_3SOCD_3$) 1.4–1.7 (m, 4H), 2.6–3.1 (m, 7H), 3.5–3.7 (m, 4H), 3.9–4.0 (m, 2H), 6.85 (m, 1H), 7.7 (m, 1H), 7.82 (m, 1H), 8.15 (d, 1H), 8.27 (m, 2H), 8.5 (s, 1H), 8.55 (d, 1H), 8.9 (d, 1H).

EXAMPLE 73

A mixture of 1-(6-chloronaphth-2-ylsulphonyl)-4-(4-piperidinylcarbonyl)piperazine (0.96 g), triethylamine (0.35 ml) and methylene chloride (10 ml) was added dropwise to a stirred solution of 2,4,6-trichloro-1,3,5-triazine (0.42 g) in methylene chloride (20 ml) which had been cooled to 0° C. The mixture was stirred at 5° C. for 1 hour. The mixture was evaporated and the residue was partitioned between ethyl acetate and water. The organic phase was washed with water, dried ($MgSO_4$) and evaporated. The residue was purified by column chromatography using increasingly polar mixtures of methylene chloride and ethyl acetate as eluent. There was thus obtained 1-(6-chloronaphth-2-ylsulphonyl)-4-[1-(4,6-dichloro-1,3,5-triazin-2-yl)piperidin-4-ylcarbonyl]piperazine (0.96 g, 74%), m.p. 230–233° C.;

NMR Spectrum ($CDCl_3$) 1.7–1.9 (m, 4H), 2.7 (m, 1H), 3.0–3.2 (m, 6H), 3.55–3.85 (m, 4H), 4.73 (m, 2H), 7.6 (m, 1H), 7.75 (m, 1H), 7.95 (m, 3H), 8.3 (m, 1H);

Elemental Analysis Found C, 46.9; H, 3.9; N, 14.4; $C_{23}H_{23}Cl_3N_6O_3S$ 0.25$CH_2Cl_2$ requires C, 47.3; H, 4.0; N, 14.2%.

EXAMPLE 74

A mixture of 1-(4-pyridyl)piperazine (0.163 g), 4-nitrophenyl 4-(6-chloronaphth-2-ylsulphonyl)piperazine-1-carboxylate (0.475 g) in DMF (5 ml) was stirred and heated to 100° C. for 16 hours. The mixture was evaporated and the residue was partitioned between ethyl acetate and 2N aqueous hydrochloric acid. The aqueous layer was basified by the addition of dilute aqueous sodium hydroxide solution and the mixture was extracted with ethyl acetate. The organic extract was dried ($MgSO_4$) and evaporated. The solid so obtained was recrystallised from a mixture of isohexane and ethyl acetate. There was thus obtained 1-(6-chloronaphth-2-ylsulphonyl)-4-[4-(4-pyridyl)piperazin-1ylcarbonyl]piperazine (0.34 g);

NMR Spectrum ($CD_3SOCD_3$) 2.95–3.05 (m, 4H), 3.15–3.3 (m, 12H), 6.75 (m, 2H), 7.75 (m, 1H), 7.8 (m, 4H), 8.1–8.3 (m, 5H), 8.5 (s, 1H);

Elemental Analysis Found C, 57.5; H, 5.3; N, 13.9; $C_{24}H_{26}ClN_5O_3S$ requires C, 57.7; H, 5.2; N, 14.0%.

The 4-nitrophenyl 4-(6-chloronaphth-2-ylsulphonyl)piperazine-1-carboxylate used as a starting material was obtained as follows:

A solution of 4-nitrophenyl chloroformate (0.4 g) in methylene chloride (15 ml) was added to a stirred mixture of 1-(6-chloronaphth-2-ylsulphonyl)piperazine hydrochloride salt (0.69 g), triethylamine (0.56 ml) and methylene chloride (30 ml) which had been cooled to 0° C. The mixture was stirred at ambient temperature for 16 hours. The mixture was evaporated and the residue was partitioned between ethyl acetate and a concentrated aqueous sodium bicarbonate solution. The organic solution was washed with 1N aqueous hydrochloric acid solution and with water, dried ($MgSO_4$) and evaporated. The solid so obtained was recrystallised from a mixture of isohexane and ethyl acetate. There was thus obtained 4-nitrophenyl 4-(6-chloronaphth-2-ylsulphonyl)piperazine-1-carboxylate (0.73 g);

NMR Spectrum ($CD_3SOCD_3$) 3.1 (m, 4H), 3.5–3.75 (m, 4H), 7.25 (m, 1H), 7.38 (d, 2H), 7.85 (m, 1H), 8.15–8.3 (m, 5H), 8.5 (s, 1H).

EXAMPLE 75

Using an analogous procedure to that described in Example 1, 1-(4-pyridyl)piperidine-4-carbonyl chloride was reacted with 4-(2-naphthylsulphonyl)piperidine to give 4-(2-naphthylsulphonyl)-1-[1-(4-pyridyl)piperidin-4-ylcarbonyl]piperidine in 33% yield;

NMR Spectrum ($CD_3SOCD_3$) 1.42–1.82 (m, 6H), 1.85–2.21 (m, 2H), 2.82–3.04 (m,4H), 3.73–3.98 (m, 5H), 4.43 (m, 1H), 6.78 (d, 2H), 7.64–7.89 (m, 3H), 8.04–8.27 (m, 5H), 8.37 (s, 1H).

The 4-(2-naphthylsulphonyl)piperidine used as a starting material was obtained as follows:

Triethylamine (8.8 ml) was added to a stirred mixture of tert-butyl 4-hydroxypiperidine-1-carboxylate (European Patent Application No. 0 495 750, Chem. Abstracts, Vol. 117, Abstract [19]1869g, 6.38 g), methanesulphonyl chloride (3.7 ml) and methylene chloride (70 ml) which had been cooled to 0° C. The mixture was stirred at 0° C. for 2 hours and then evaporated. The residue was partitioned between ethyl acetate and a concentrated aqueous citric acid solution. The organic phase was washed with water, dried ($MgSO_4$) and evaporated. The residue was purified by column chromatography using ethyl acetate as eluent to give tert-butyl 4-mesyloxypiperidine-1-carboxylate (7.82 g).

A mixture of a portion (0.99 g) of the material so obtained, sodium 2-naphthalenesulphinate (14.3 g) and DMF (70 ml) was stirred and heated to 120° C. for 5 hours. The mixture was evaporated and the residue was partitioned between ethyl acetate and 2N aqueous sodium hydroxide solution. The organic phase was dried ($MgSO_4$) and evaporated to give tert-butyl 4-(2-naphthylsulphonyl)piperidine-1-carboxylate (0.64 g) which was used without further purification.

A mixture of a portion (0.56 g) of the material so obtained and trifluoroacetic acid (5 ml) was stirred at ambient temperature for 1 hour. The mixture was diluted with ethyl acetate and washed with 2N aqueous sodium hydroxide. The organic layer was dried ($MgSO_4$) and evaporated to give 4-(2-naphthylsulphonyl)piperidine (0.18 g);

NMR Spectrum ($CD_3SOCD_3$) 1.36–2.08 (m, 4H), 2.8–3.05 (m, 4H), 4.12–4.55 (m, 1H), 7.6–8.25 (m, 6H), 8.34 (s, 1H).

The sodium 2-naphthalenesulphinate used above was obtained as follows:

2-Naphthalenesulphonyl chloride (15.9 g) was added portionwise during 2 hours to a stirred mixture of sodium sulphite (33 g), sodium bicarbonate (11.6 g) and water (66 ml) which had been warmed to 70° C. The resultant mixture was stirred at 75° C. for 1 hour and stored at ambient temperature for 16 hours. The precipitate was isolated. There was thus obtained sodium 2-naphthalenesulphinate (31 g).

EXAMPLE 76

Using an analogous procedure to that described in Example 1, 1-(4-pyridyl)piperidine-4-carbonyl chloride was reacted with 4-(2-naphthylthio)piperidine to give 4-(2-naphthylthio)-1-[1-(4-pyridyl)piperidin-4-ylcarbonyl]piperidine in 62% yield;

NMR Spectrum ($CD_3SOCD_3$, 100° C.) 1.25–1.75 (m, 6H), 1.87–2.1 (broad s, 2H), 2.78–3.0 (m, 4H), 3.20 (d, 1H), 3.64 (m, 1H), 3.6–4.04 (m, 3H), 4.2 (d, 1H), 6.78 (d, 2H), 7.44–7.58 (m, 3H), 7.63–7.74 (m, 3H), 7.75 (d, 1H), 8.12 (s, 2H);

Elemental Analysis Found C, 72.2; H, 6.7; N, 9.7; $C_{26}H_{29}N_3OS$ requires C, 72.4; H, 6.8; N, 9.7%.

The 4-(2-naphthylthio)piperidine used as a starting material was obtained as follows:

A solution of 2-naphthalenethiol (2.34 g) in DMF (10 ml) was added dropwise to a stirred mixture of sodium hydride (60% dispersion in mineral oil, 0.65 g) and DMF (20 ml) which had been cooled to 10° C. The resultant mixture was stirred at 0° C. for 30 minutes. A solution of tert-butyl 4-mesyloxypiperidine-1-carboxylate (3.9 g) in DPF (40 ml) was added dropwise. The mixture was allowed to warm to ambient temperature. The mixture was partitioned between ethyl acetate and water. The organic phase was washed with water, dried ($MgSO_4$) and evaporated. The residue was purified by column chromatography using methylene chloride as eluent. There was thus obtained tert-butyl 4-(2-naphthylthio)piperidine-1-carboxylate (0.65 g).

A mixture of the material so obtained and trifluoroacetic acid was stirred at ambient temperature for 30 minutes. The mixture was diluted with ethyl acetate and washed with 2N aqueous sodium hydroxide solution. The organic solution was dried ($MgSO_4$) and evaporated. There was thus obtained 4-(2-naphthylthio)piperidine (0.32 g);

NMR Spectrum ($CD_3SOCD_3$) 1.42 (m, 2H), 1.88 (m, 2H), 2.58 (m, 2H), 2.94 (m, 2H), 3.43 (m, 1H), 7.5 (m, 3H), 7.89 (m, 4H).

EXAMPLE 77

Using an analogous procedure to that described in Example 1, 1-(4-pyridyl)piperidine-4-carbonyl chloride was reacted with 2-hydroxymethyl-4-(2-naphthylsulphonyl)piperazine to give 2-hydroxymethyl-4-(2-naphthylsulphonyl)-1-[1-(4-pyridyl)piperidin-4-ylcarbonyl]piperazine in 42% yield;

NMR Spectrum ($CD_3SOCD_3$, 100° C.) 1.55–1.72 (m, 2H), 1.83–1.95 (m, 2H), 2.35–3.05 (m, 8H), 3.49 (I, 2H), 3.7 (m, 2H), 4.01 (7, 2H), 6.72,(d, 2H), 7.63–7.79 (mn, 3H), 8.0–8.2 (mn, 5H), 8.39(H, 1H);

Elemental Analysis Found C, 61.2; H, 6.2; N, 10.4; $C_{26}H_{30}N_4O_4S$ 0.25 EtAC 0.75$H_2O$ requires C, 61.2; H, 6.4; N, 10.6%.

The 2-hydroxinethyl-4-(2-naphthylsulphonyl)piperazine used as a starting material was obtained in 49% yield by the reaction of 2-hydroxymethylpiperazine (*J. Med. Chem.*, 1990, 33, 142) and 2-naphthylsulphonyl chloride using an analogous procedure to that described in Example 2;

NMR Spectrum ($CD_3SOCD_3$) 1.93 (t, 1H), 2.24 (.m, 2H), 2.68 (m, 2H), 2.93 (m, 1H), 3.6 (m, 2H), 4.67 (t, H, 7.76 (m, 3H), 8.07–8.28 ((m, 3H), 8.44 (s, 1H).

EXAMPLE 78

1,1'-Carbonyldiimidazole (0.208 g) was added to a stirred solution of N-(6-chloronaphth-2-ylsulphonyl)glycine (0.39 g) in DMF (10 ml) and the mixture was stirred at ambient temperature for 30 minutes. 1-(4-Pyridyl)piperazine (0.21 g) was added and the mixture was stirred at ambient temperature for 18 hours. The mixture was partitioned between ethyl acetate and water. The organic phase was washed with brine, dried ($MgSO_4$) and evaporated. The residue was recrystallised from a mixture of hexane, ethyl acetate and methanol. There was thus obtained 1-[2-(6-chloronaphthalenesulphonamido)acetyl] -4-(4-pyridyl)piperazine (0.179 g, 20%), m.p. 192–193° C.;

NMR Spectrum ($CD_3SOCD_3$) 3.15 (m, 2H), 3.3-3.6 (m , 6H), 3.85 ((, 2H), 6.7–7.0 (m, 2H), 7.6 (i, H), 7.8–8.0 ((, 2H), 8.1–8.3 (m, 4H), 8.5 (s, 1H);

Elemental Analysis Found C, 56.5; H, 4.8; N, 12.4; $C_{21}H_{21}ClN_4O_3S$ requires C, 56.7; H, 4.8; N, 12.6%.

The N-(6-chloronaphth-2-ylsulphonyl)glycine used as a starting material was obtained as follows:

Triethylamine (0.278 ml) was added to a stirred mixture of 6-chloronaphth-2-ylsulphonyl chloride (0.522 g), glycine methyl ester hydrochloride (0.251 g) and methylene chloride (10 ml) and the mixture was stirred at ambient temperature for 1 hour. The mixture was partitioned between ethyl acetate and water. The organic phase was washed with brine, dried ($MgSO_4$) and evaporated. The residue was recrystallised from methanol to give methyl N-(6-chloronaphth-2-ylsulphonyl)glycine (0.46 g).

A mixture of the material so obtained, and 2N aqueous sodium hydroxide solution (3 ml) was stirred at ambient temperature for 30 minutes. The mixture was partitioned between diethyl ether and water. The aqueous phase was acidified by the addition of 2N aqueous hydrochloric acid and extracted with ethyl acetate. The organic phase was washed with water and with brine, dried ($MgSO_4$) and evaporated. There was thus obtained the required starting material (0.39 g) which was used without further purification.

EXAMPLE 79

A mixture of 1-(4'-ethoxycarbonylbiphenyl-4-ylsulphonyl)-4-[1-(4-pyridyl)piperidin-4-ylcarbonyl]piperazine (0.08 g), 2N aqueous sodium hydroxide solution (0.28 ml), water (2 ml) and methanol (10 ml) was stirred and heated to reflux for 3 hours. The mixture was poured into water and extracted with methylene chloride. The aqueous suspension was filtered. The solid so obtained was resuspended in water. The mixture was acidified by the addition of glacial acetic acid and stirred for 2 hours. The solid was isolated, washed with water and with diethyl ether and dried. There was thus obtained 1-(4'-carboxybiphenyl-4-ylsulphonyl)-4-[1-(4-pyridyl)piperidin-4-ylcarbonyl]piperazine (0.035 g);

NMR Spectrum ($CD_3SOCD_3$, 100° C.) 1.6–1.86 (m, 4H), 3.0 (m, 1H), 3.15 (t, 4H), 3.32 (m, 2H), 3.63 (t, 4H), 3.97 (t, 1H), 4.03 (t, 1H), 7.01 (d, 2H), 7.24–7.96 (m, 6H), 8.09 (d, 4H).

EXAMPLE 80

Ethanethiol (0.15 ml) was added dropwise to a stirred suspension of sodium hydride (60% dispersion in mineral oil, 0.083 g) in DMPU (3 ml) which had been cooled to 3° C. and the mixture was stirred and allowed to warm to ambient temperature over 30 minutes. A solution of 1-(6-methoxynaphth-2-ylsulphonyl)-4-[1-(4-pyridyl)piperidin-4-ylcarbonyl]piperazine (0.1 g) in DMPU (2 ml) was added and the mixture was stirred and heated to 110° C. for 90 minutes. The mixture was cooled to ambient temperature and partitioned between methylene chloride and water. The organic phase was shaken with a slight excess of 2M aqueous sodium hydroxide. The resultant precipitate was isolated and dried. There was thus obtained 1-(6-hydroxynaphth-2-ylsulphonyl)-4-[1-(4-pyridyl)piperidin-4-ylcarbonyl]piperazine sodium salt (0.052 g);

NMR Spectrum (CD$_3$SOCD$_3$, 100° C.) 1.5–1.73 (m, 4H), 2.72–3.23 (m, 7H), 3.55 (t, 4H), 3.68–3.88 (m, 2H), 6.72 (m, 2H), 6.8 (m, 1H), 6.96 (m, 1H), 7.45 (m, 2H), 7.69 (m, 1H), 7.99 (m, 1H), 8.11 (m, 2H);

Elemental Analysis Found C 53.8; H, 5.6; N, 10.0; C$_{25}$H$_{27}$N$_4$O$_4$S 3H$_2$O Na requires C, 53.9; H, 5.9; N, 10.1%.

EXAMPLE 81

Using an analogous procedure to that described in Example 1, 1-(4-pyridyl)piperidine-4-carbonyl chloride was reacted with methyl 2-[1-(2-naphthylsulphonyl)piperazin-2-yl]acetate to give 2-methoxycarbonylmethyl-1-(2-naphthylsulphonyl)-4-[1-(4-pyridyl)piperidin-4-ylcarbonyl]piperazine in 90% yield as a glass;

NMR Spectrum (CD$_3$SOCD$_3$+CD$_3$CO$_2$D, 100° C.) 1.6–1.85 (m, 4H), 2.4–2.65 (m, 2H), 2.85–3.35 (m, 6H), 3.55 (s, 3H), 3.78 (m, 1H), 3.9–4.1 (m, 4H), 4.45 (m, 1H), 6.95 (d, 2H), 7.68 (m, 2H), 7.8 (m, 1H), 7.95–8.15 (m, 5H), 8.45 (d, 1H);

Elemental Analysis Found C, 61.7; H, 6.3; N, 10.3; C$_{28}$H$_{32}$N$_4$O$_5$S 0.5H$_2$O requires C, 61.65; H, 6.05; N, 10.3%.

The methyl 2-[1-(2-naphthylsulphonyl)piperazin-2-yl]acetate used as a starting material was obtained as follows:

Using an analogous procedure to that described in Example 2, methyl 2-(1-benzylpiperazin-3-yl)acetate (*J. Chem. Soc. Perkin I*, 1992, 1035) was reacted with 2-naphthylsulphonyl chloride to give methyl 2-[4-benzyl-1-(2-naphthylsulphonyl)piperazin-2-yl]acetate in 90% yield.

The material so obtained was reacted with 1-chloroethyl chloroformate using an analogous procedure to that described in the second paragraph of the portion of Example 44 which is concerned with the preparation of starting materials. There was thus obtained methyl 2-[1-(2-naphthylsulphonyl)piperazin-2-yl]acetate in 87% yield;

NMR Spectrum (CD$_3$SOCD$_3$) 2.55–2.7 (m, 2H), 2.9 (m, 1H), 3.05–3.45 (m, 4H), 3.55 (s, 3H), 3.9 (m, 1H), 4.6 (m, 1H), 7.65–7.9 (m, 3H), 8.12 (m, 3H), 8.55 (d, 1H), 9.3 (t, 2H).

EXAMPLE 82

Using an analogous procedure to that described in Example 1, 1-(4-pyridyl)piperidine-4-carbonyl chloride was reacted with ethyl 1-(6-bromonaphth-2-ylsulphonyl)piperazine-3-carboxylate to give 4-(6-bromonaphth-2-ylsulphonyl)-2-ethoxycarbonyl-1-[1-(4-pyridyl)piperidin-4-ylcarbonyl]piperazine in 42% yield, m.p. 117–121° C.;

NMR Spectrum (CD$_3$SOCD$_3$, 100° C.) 1.2 (t, 3H), 1.5–1.8 (m, 4H), 2.55 (m, 1H), 2.7–3.05 (m, 5H), 3.65–3.85 (m, 3H), 4.05–4.25 (m, 4H), 5.08 (m, 1H), 6.7 (d, 2H), 7.77 (m, 2H), 8.1 (m, 4H), 8.3 (d, 1H), 8.45 (d, 1H).

Elemental Analysis Found C, 54.2; H, 5.2; N, 9.0; C$_{28}$H$_{31}$BrN$_4$O$_5$S requires C, 54.6; H, 5.1; N, 9.1%.

The ethyl 1-(6-bromonaphth-2-ylsulphonyl)piperazine-3-carboxylate used as a starting material was obtained in 71% yield from ethyl 1-benzylpiperazine-2-carboxylate and 6-bromonaphth-2-ylsulphonyl chloride using analogous procedures to those described in the portion of Example 44 which is concerned with the preparation of starting materials.

EXAMPLE 83

Using an analogous procedure to that described in Example 61, 4-(6-bromonaphth-2-ylsulphonyl)-2-ethoxycarbonyl-1-[1-(4-pyridyl)piperidin-4-ylcarbonyl]piperazine was hydrolysed to give 4-(6-bromonaphth-2-ylsulphonyl)-2-carboxy-1-[1-(4-pyridyl)piperidin-4-ylcarbonyl]piperazine in 92% yield, m.p. 216–222° C. (decomposes);

NMR Spectrum (CD$_3$SOCD$_3$, 100° C.) 1.5–1.8 (m, 4H), 2.52 (m, 1H), 2.7 (m, 1H), 2.8–3.05 (m, 3H), 3.25 (m, 1H), 3.6–4.3 (m, 5H), 4.95 (m, 1H), 6.75 (d, 2H), 7.75 (m, 2H), 8.0–8.15 (m, 4H), 8.3 (d, 1H), 8.4 (d, 1H).

Elemental Analysis Found C, 52.4; H, 4.8; N, 9.3; C$_{26}$H$_{27}$BrN$_4$O$_5$S 0.5H$_2$O requires C, 52.35; H, 4.7; N, 9.4%.

EXAMPLE 84

Using an analogous procedure to that described in Example 20, 4-(6-bromonaphth-2-ylsulphonyl)-2-carboxy-1-[1-(4-pyridyl)piperidin-4-ylcarbonyl]piperazine was reacted with morpholine to give 4-(6-bromonaphth-2-ylsulphonyl)-2-morpholinocarbonyl-1-[1-(4-pyridyl)piperidin-4-ylcarbonyl]piperazine in 60% yield, m.p. 235–237 °C.;

NMR Spectrum (CD$_3$SOCD$_3$, 100° C.) 1.5–1.8 (m, 4H), 2.7–3.05 (m, 5H), 3.4 (m, 4H), 3.5–3.6 (mn, 4H), 3.67 (m, 1H), 3.75–3.9 (m, 4H), 3.98 (mn, 1H), 5.2 (m, 1H), 6.65–6.8 (mn, 2H), 7.75 (m, 2H), 8.1 (m, 4H), 8.3 (d, 1H), 8.45 (d, 1H);

Elemental Analysis Found C, 53.7; H, 5.2; N, 10.2; C$_{30}$H$_{34}$BrN$_5$O$_5$S H$_2$O requires C, 53.5; H, 5.35; N, 10.4%.

EXAMPLE 85

A mixture of 1-(6-chloronaphth-2-ylsulphonyl)-4-[1-(4,6-dichloro-1,3,5-triazin-2-yl)piperidin-4-ylcarbonyl]piperazine (0.891 g), magnesium oxide (0.5 g), 10% palladium-on-carbon catalyst (0.2 g) and DMF (15 ml) was stirred under an atmosphere of hydrogen gas until uptake of hydrogen ceased. The mixture was filtered and the filtrate was partitioned between ethyl acetate and water. The organic phase was dried (MgSO$_4$) and evaporated. There was thus obtained 1-(2-naphthylsulphonyl)-4-[1-(1,3,5-triazin-2-yl)piperidin-4-ylcarbonyl]piperazine (0.36 g);

NMR Spectrum (CD$_3$SOCD$_3$) 1.3–1.7 (m, 4N), 2.8–3.1 (m, 7H), 3.5–3.7 (m, 4H), 4.5–4.7 (m, 2H), 7.6–7.8 (m, 3H), 8.1–8.3 (m, 3H), 8.45 (s, 1H), 8.55 (s, 2H).

EXAMPLE 86

Using an analogous procedure to that described in Example 56, 2-amino-4-chloro-6-methylpyrimidine was reacted with 1-(6-chloronaphth-2-ylsulphonyl)-4-(4-piperidinylcarbonyl)piperazine. The reaction mixture was concentrated by evaporation to one half of its original volume and cooled to ambient temperature. The precipitate which formed was isolated, washed with diethyl ether and dried. There was thus obtained 4-[1-(2-amino-6-methylpyrimidin-4-yl)piperidin-4-ylcarbonyl]-1-(6-chloronaphth-2-ylsulphonyl)piperazine in 39% yield, m.p. 210–212° C.;

NMR Spectrum (CD$_3$SOCD$_3$) 1.2–1.6 (m, 4H), 2.0 (s, 3H), 2.8 (m, 3H), 2.9–3.1 (m, 4H), 3.5–3.7 (m, 4H), 4.2 (m, 2H), 5.82 (s, 2H), 5.86 (s, 1H), 7.7 (m, 1H), 7.8 (m, 1H), 8.2 (d, 1H), 8.25 (s, 1H), 8.3 (d, 1H), 8.5 (s, 1H);

Elemental Analysis Found C, 56.3; H, 5.5; N, 15.3; C$_{25}$H$_{29}$ClN$_6$O$_3$S 0.4H$_2$O requires C, 55.9; H, 5.6; N, 15.7%.

EXAMPLE 87

Using an analogous procedure to that described in Example 56, 4-chloropyrimidine was reacted with methyl 4-(6-chloronaphth-2-ylsulphonyl)-1-(4-piperidinylcarbonyl)piperazine-2-carboxylate and the reaction product was purified by column chromatography using increasingly polar mixtures of methylene chloride and methanol to give 4-(6-chloronaphth-2-ylsulphonyl)-2-methoxycarbonyl-1-[1-(4-pyridyl)piperidin-4-ylcarbonyl]piperazine in 77% yield;

NMR Spectrum 1.6–2.0 (m, 4H), 2.5 (m, 2H), 2.8 (m, 1H), 3.0 (m, 1H), 3.6–3.9 (m, 6H), 4.25–4.45 (m, 3H), 5.35 (m, 1H), 6.5 (d, 1H), 7.6 (m, 1H), 7.75 (m, 1H), 7.95 (m, 3H), 8.2 (d, 1H), 8.35 (s, 1H), 8.6 (s, 1H);

Elemental Analysis Found C, 54.5; H, 5.2; N, 11.8; C$_{26}$H$_{28}$ClN$_5$O$_5$S 0.2CH$_2$Cl$_2$ requires C, 54.7; H, 4.9; N, 12.2%.

The methyl 4-(6-chloronaphth-2-ylsulphonyl)-1-(4-piperidinylcarbonyl)piperazine-2-carboxylate used as a starting material was obtained as follows:

Benzyl chloroformate (8.5 g) was added dropwise to a stirred mixture of ethyl piperidine-4-carboxylate (7.85 g), triethylamine (6.95 ml) and methylene chloride (50 ml) which had been cooled to 5° C. The mixture was stirred at ambient temperature for 18 hours. The mixture was partitioned between ethyl acetate and 2N aqueous hydrochloric acid. The organic phase was washed with water and with brine, dried (MgSO$_4$) and evaporated. The residue was dissolved in methanol (100 ml) and 2N aqueous sodium hydroxide (125 ml) was added. The mixture was stirred at ambient temperature for 1 hour. The mixture was concentrated by evaporation and the residue was partitioned between diethyl ether and water. The aqueous phase was acidified to pH3 by the addition of concentrated hydrochloric acid and the mixture was extracted with ethyl acetate. The organic extract was washed with water, dried (MgSO$_4$) and evaporated to give 1-benzyloxycarbonylpiperidine-4-carboxylic acid (10.1 g).

Oxalyl chloride (0.429 ml) and DHF (1 drop) were added to a stirred solution of 1-benzyloxycarbonylpiperidine-4-carboxylic acid (0.622 g) in methylene chloride (20 ml). The mixture was stirred at ambient temperature for 2 hours and then evaporated. The residue was dissolved in methylene chloride (10 ml) and added dropwise to a stirred mixture of methyl 4-(6-chloronaphth-2-ylsulphonyl)piperazine-3-carboxylate (0.93 g), triethylamine (0.7 ml) and methylene chloride (10 ml) which had been cooled to 0° C. The mixture was stirred at ambient temperature for 2 hours. The mixture was partitioned between ethyl acetate and 2N aqueous hydrochloric acid. The organic phase was washed with a saturated aqueous sodium bicarbonate solution, with water and with brine, dried (MgSO$_4$) and evaporated. The residue was purified by column chromatography using increasingly polar mixtures of hexane and ethyl acetate as eluent. There was thus obtained methyl 1-(1-benzyloxycarbonylpiperidin-4-ylcarbonyl)-4-(6-chloronaphth-2-ylsulphonyl)piperazine-2-carboxylate (1.21 g);

NMR Spectrum 1.4–1.9 (m, 4H), 2.3–2.7 (m, 3H), 2.85 (m, 2H), 3.5–3.9 (m, 6H), 4.15 (m, 2H), 4.35 (m, 1H), 5.1 (s, 2H), 5.3 (m, 1H), 7.2–7.4 (m, 5H), 7.6 (m, 1H), 7.75 (m, 1H), 7.75–8.0 (m, 3H), 8.3 (s, 1H).

A mixture of a portion (0.512 g) of the material so obtained and a saturated solution of hydrogen bromide gas in glacial acetic acid (5 ml) was stirred at ambient temperature for 20 minutes. Diethyl ether (100 ml) was added and the mixture was stirred vigorously. The precipitate was isolated, washed with diethyl ether and dried. There was thus obtained methyl 4-(6-chloronaphth-2-ylsulphonyl)-1-(4-piperidinylcarbonyl)piperazine-2-carboxylate which was used without further purification.

The methyl 4-(6-chloronaphth-2-ylsulphonyl)piperazine-3-carboxylate used above as an intermediate was obtained by the reaction of methyl 1-benzylpiperazine-2-carboxylate (prepared in analogous fashion to the corresponding ethyl ester which is described in *Helv. Chim. Acta*, 1962, 45, 2383) and 6-chloronaphth-2-ylsulphonyl chloride using analogous procedures to those described in the portion of Example 44 which is concerned with the preparation of starting materials.

EXAMPLE 88

A mixture of 4-(6-chloronaphth-2-ylsulphonyl)-2-methoxycarbonyl-1-[1-(4-pyridyl)piperidin-4-ylcarbonyl]piperazine (0.362 g), 1N aqueous sodium hydroxide solution (1.3 ml) and methanol (5 ml) was stirred and heated to reflux for 30 minutes. The mixture was acidified by the addition of 2N aqueous hydrochloric acid (2 ml) and evaporated. The residue was dried to give 2-carboxy-4-(6-chloronaphth-2-ylsulphonyl)-1-[1-(4-pyridyl)piperidin-4-ylcarbonyl]piperazine (0.41 g);

NMR Spectrum (CD$_3$SOCD$_3$) 1.4–1.9 (m, 4H), 2.1–2.5 (m, 1H), 3.0–3.75 (m, 8H), 4.0–4.3 (m, 2H), 5.12 (m, 1H), 7.2 (m, 1H), 7.7 (m, 1H), 7.85 (m, 1H), 8.1–8.3 (m, 4H), 8.55 (s, 1H), 8.75 (s, 1H);

Elemental Analysis Found C, 41.0; H, 4.2; N, 9.4; C$_{25}$H$_{26}$ClN$_5$O$_5$S 2NaCl 2H$_2$O HCl requires C, 40.9; H, 4.3; N, 9.6%.

EXAMPLE 89

A solution of (E)-4-chlorostyrylsulphonyl chloride (0.12 g) in methylene chloride (2 ml) was added to a stirred suspension of 4-[4-(4-pyridyl)piperazin-1-ylcarbonyl]aniline (0.141 g) in methylene chloride (10 ml). The mixture was stirred at ambient temperature for 64 hours. The resulting solid was isolated and washed with methylene chloride. The residue was purified by column chromatography using a 10:1 mixture of methylene chloride and methanol as eluent. There was thus obtained N-{4-[4-(4-pyridyl)piperazin-1-ylcarbonyl]phenyl}-(E)-4-chlorostyrenesulphonamide (0.089 g), m.p. 207–209° C.;

NMR Spectrum (CD$_3$SOCD$_3$, 100° C.) 3.43 (m, 4H), 3.6 (m, 4H), 6.8 (d, 2H), 7.15 (d, 1H), 7.27 (d, 2H), 7.3–7.5 (m, 5H), 7.63 (d, 2H), 8.16 (d, 2H);

Elemental Analysis Found C, 59.0; H, 4.9; N, 11.3; C$_{24}$H$_{23}$ClN$_4$O$_3$S 0.25H$_2$O requires C, 59.1; H, 4.9; N, 11.5%.

The 4-[4-(4-pyridyl)piperazin-1-ylcarbonyl]aniline used as a starting material was obtained as follows:

4-Nitrobenzoyl chloride (4.64 g) was added to a stirred suspension of 1-(4-pyridyl)piperazine (4.08 g), triethylamine (3.48 ml) and DMF (50 ml) which had been cooled to 4° C. The mixture was stirred at 4° C. for 1 hour and at ambient temperature for 16 hours. The mixture was partitioned between methylene chloride and water. The organic phase was washed with brine, dried (MgSO$_4$) and evaporated. The residue was purified by column chromatography using a 10:1 mixture of methylene chloride and methanol as eluent. There was thus obtained 4-[4-(4-pyridyl)piperazin-1-ylcarbonyl]nitrobenzene (5.09 g), m.p. 158–160° C.

A mixture of a portion (3.74 g) of the material so obtained, 10% palladium-on-carbon catalyst (0.3 g), 1N aqueous hydrochloric acid (24 ml) and methanol (75 ml) was stirred under an atmosphere of hydrogen gas until uptake of hydrogen ceased. The mixture was filtered and the filtrate was evaporated. The residue was dissolved in water (25 ml) and the solution was basified to pH10 by the addition of 1N aqueous sodium hydroxide solution. The resultant precipitate was isolated, washed with water and dried. There was thus obtained 4-[4-(4-pyridyl)piperazin-1-ylcarbonyl]aniline (2.91 g), m.p. 254–256° C.

EXAMPLE 90

Using an analogous procedure to that described in Example 89, 4-[4-(4-pyridyl)piperazin-1-ylcarbonyl]aniline was reacted with 4'-bromo-4-biphenylylsulphonyl chloride to give N-{4-[4-(4-pyridyl)piperazin-1-ylcarbonyl]phenyl}-4'-bromo-4-biphenylylsulphonamide hydrochloride salt in 90% yield, m.p. 201–205° C.;

NMR Spectrum (CD$_3$SOCD$_3$) 3.6 (m, 4H), 3.73 (m, 4H), 7.18.(m, 4H), 7.39 (m, 2H), 7.69 (s, 4H), 7.9 (s, 4H), 8.27 (d, 2H);

Elemental Analysis Found C, 54.0; H, 4.4; N, 9.0; C$_{28}$H$_{25}$BrN$_4$O$_3$S HCl 0.5H$_2$O requires C, 54.0; H, 4.4; N, 9.0%.

EXAMPLE 91

Using an analogous procedure to that described in Example 20, 4-(6-bromonaphth-2-ylsulphonyl)-2-carboxy-1-[1-(4-pyridyl)piperidin-4-ylcarbonyl]piperazine was reacted with glycine methyl ester to give 4-(6-bromonaphth-2-ylsulphonyl)-2-[N-(methoxycarbonylmethyl)carbamoyl]-1-[1-(4-pyridyl)piperidin-4-ylcarbonyl]piperazine in 76% yield as a glass;

NMR Spectrum (CD$_3$SOCD$_3$, 100° C.) 1.55–1.8 (m, 4H), 2.55–3.1 (m, 6H), 3.4 (m, 1H), 3.65 (s, 3H), 3.7–3.95 (m, 4H), 4.15 (m, 2H), 4.95 (m, 1H), 6.75 (d, 2H), 7.7–7.9 (m, 3H), 8.05–8.15 (m, 4H), 8.3 (d, 1H), 8.4 (d, 1H);

Elemental Analysis Found C, 51.9; H, 5.0; N, 10.2; C$_{29}$H$_{32}$BrN$_5$O$_6$S 0.75H$_2$O requires C, 51.9; H, 5.0; N, 10.4%.

EXAMPLE 92

Using an analogous procedure to that disclosed in Example 2, 1-(4-piperidinylcarbonyl)-4-(4-pyridyl)piperazine was reacted with 6-bromonaphth-2-ylsulphonyl chloride to give 1-[1-(6-bromonaphth-2-ylsulphonyl)piperidin-4-ylcarbonyl]-4-(4-pyridyl)piperazine in 20% yield, m.p. 229–230° C.;

NMR Spectrum (CD$_3$SOCD$_3$) 1.6 (m, 4H), 2.3–2.7 (m, 3H), 3.5–3.8 (m, 10H), 6.8 (d, 2H), 7.8 (d, 2H), 8.2 (t, 4H), 8.4 (d, 1H), 8.5 (d, 1H).

The 1-(4-piperidinylcarbonyl)-4-(4-pyridyl)piperazine used as a starting material was obtained as follows:

Di-tert-butyl dicarbonate (5.09 g) was added to a stirred mixture of piperidine-4-carboxylic acid (3 g), sodium carbonate (2.48 g), 1,4-dioxan (20 ml) and water (20 ml) which had been cooled to 0° C. The mixture was stirred at ambient temperature for 18 hours. The mixture was concentrated by evaporation to one third of the original volume and a saturated sodium bisulphate solution was added to bring the solution to pH2 to 3. The mixture was extracted with ethyl acetate. The organic phase was washed with water and with brine, dried (MgSO$_4$) and evaporated to give 1-tert-butoxycarbonylpiperidine-4-carboxylic acid (4.36 g) which was used without further purification.

Using an analogous procedure to that described in Example 14, a portion (1.41 g) of the material so obtained was reacted with 1-(4-pyridyl)piperazine to give 1-(1-tert-butoxycarbonylpiperidin-4-ylcarbonyl)-4-(4-pyridyl)piperazine in 20% yield;

NMR Spectrum (CD$_3$SOCD$_3$) 1.4 (s, 9H), 1.6 (m, 2H), 2.9 (m, 6H), 3.4 (s, 2H), 3.6 (d, 3H), 4.0 (m, 4H), 7.0–8.0 (m, 4H).

A mixture of the material so obtained (0.45 g), 4N aqueous hydrochloric acid (2 ml) and diethyl ether (15 ml) was stirred at ambient temperature for 18 hours. The mixture was evaporated to give 1-(4-piperidinylcarbonyl)-4-(4-pyridyl)piperazine (0.31 g) which was used without further purification.

EXAMPLE 93

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium stearate | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

-continued

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml. buffered to pH6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

CHEMICAL FORMULAE

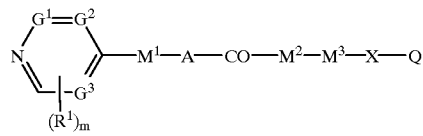

I

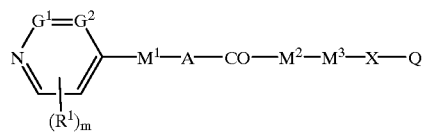

Ia

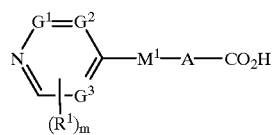

II

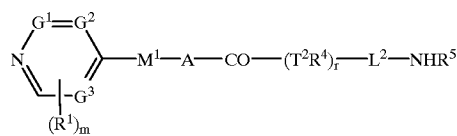

III

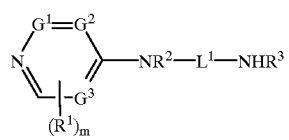

IV

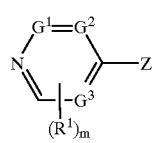

V

What is claimed is:

1. A compound of the formula I

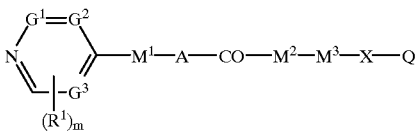

I wherein:
each of $G^1$, $G^2$ and $G^3$ is CH;
m is 1 or 2;
each $R^1$ is independently selected from hydrogen, amino, halogeno, cyano, (1–4C)alkyl and (1–4C)alkoxy;
$M^1$ is a group of the formula $$NR^2—L^1—T^1R^3$$

in which $R^2$ and $R^3$ together form a (1–4C)alkylene group, $L^1$ is (1–4C)alkylene, and
$T^1$ is CH or N,
and wherein 1 or 2 methylene groups within L and the rings formed when $R^2$ and $R^3$ are linked optionally bears a (1–4C)alkyl substituent;
A is a direct link to the carbonyl group, or A is (1–4C)alkylene;
$M^2$ is a group of the formula $$(T^2R^4)_r—L^2—T^3R^5$$

in which r is 0 or 1,
$T^2$ is N,
$T^3$ is N,
$R^4$ is hydrogen or (1–4C)alkyl,
$R^5$ is hydrogen or (1–4C)alkyl,
or $R^4$ and $R^5$ together form a (1–4C)alkylene, methylenecarbonyl or carbonylmethylene group, or $R^4$ is a (2–3C)alkylene group which is linked to a methylene group within $L^2$ forming a 5- or 6-membered ring involving $R^4$ and $T^2$, or $R^5$ is a (2–3C)alkylene group which is linked to a methylene group within $L^2$ forming a 5- or 6-membered ring involving $R^5$ and $T^3$,
$L^2$ is (1–4C)alkylene or (1–3C)alkylene-carbonyl, and, when r is 1, $L^2$ may also be carbonyl-(1–3C)alkylene,
and wherein 1 or 2 methylene groups within $L^2$ and the rings formed when $R^4$ and $R^5$,
$R^4$ and $L^2$ or $R^5$ and $L^2$ are linked optionally bears a substituent selected from the group consisting of oxo, carboxy, (1–4C)alkoxycarbonyl, carbamoyl, N-(1-4C)alkylcarbamoyl, N,N-di-(1–4C) alkylcarbamoyl, pyrrolidin-1-ylcarbonyl, piperidinocarbonyl, morpholinocarbonyl, piperazin-1-ylcarbonyl, 4-(1–4C)alkylpiperazin-1-ylcarbonyl, N-phenylcarbamoyl, N-(1-4C)alkyl-N-phenylcarbamoyl, N-[phenyl-(1–3C)alkyl] carbamoyl, N-(1–4C)alkyl-N-[phenyl-(1–3C)alkyl] carbamoyl, N-[hydroxy-(2–3C)alkyl]carbamoyl, N-(1–4C)alkyl-N-[hydroxy-(2–3C)alkyl]carbamoyl, N-[(1–4C)alkoxy-(2–3C)alkyl]carbamoyl, N-(1–4C) alkyl-N-[(1–4C)alkoxy-(2–3C)alkyl]carbamoyl, N-[carboxy-(1–3C)alkyl]carbamoyl, N-(1–4C)alkyl- N-[carboxy-(1–3C)alkyl]carbamoyl, N-[carboxy-(1–3C)alkyl]-N-[hydroxy-(2–3C)alkyl]carbamoyl, N-[carboxy-(1–3C)alkyl]-N-[(1–4C)alkoxy-(2–3C)alkyl]carbamoyl, N-[(1–4C)alkoxycarbonyl-(1–3C)alkyl]carbamoyl, N-(1–4C)alkyl-N-[(1–4C)alkoxycarbonyl-(1–3C)alkyl]carbamoyl, N-[(1–4C)alkoxycarbonyl-(1–3C)alkyl]-N-[hydroxy-(2–3C)alkyl]carbamoyl, N-[(1–4C)alkoxycarbonyl-(1–3C)alkyl]-N-[(1–4C)alkoxy-(2–3C)alkyl]carbanoyl, (1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, pyrrolidin-1-ylcarbonyl-(1–4C)alkyl, piperidinocarbonyl-(1–4C)alkyl, morpholinocarbonyl-(1–4C)alkyl, piperazin-1-ylcarbonyl-(1–4C)alkyl, 4-(1–4C)alkylpiperazin-1-ylcarbonyl-(1–4C)alkyl, N-phenylcarbamoyl-(1–4C)alkyl, N-[phenyl-(1–3C)alkyl]carbamoyl-(1–4C)alkyl, hydroxy-(1–4C)alkyl, (1–4C)alkoxy-(1–4C)alkyl and phenyl-(1–4C)alkyl, and wherein any heterocyclic group in said substituent optionally bears 1 or 2 substituents selected from the group consisting of (1–4C)alkyl, (1–4C)alkoxy, carboxy, (1–4C)alkoxycarbonyl, carbamoyl, N-(1–4C)alkylcarbamoyl and N,N-di-(1–4C)alkylcarbamoyl, and wherein any phenyl or phenylene group in $M^2$ optionally bears 1 or 2 substituents selected from the group consisting of halogeno, trifluoromethyl, (1–4C)alkyl and (1–4C)alkoxy;

$M^3$ is a direct link to X, or $M^3$ is a group of the formula $$L^3-(NR^6)_s$$

in which s is 0 or 1, $R^6$ is hydrogen or (1–4C)alkyl, or $R^5$ and $R^6$ together form a (1–4C)alkylene, methylenecarbonyl or carbonylmethylene group, or $R^6$ is a (2–3C)alkylene group which is linked to a methylene group within $L^3$ forming a 5- or 6-membered ring involving $NR^6$, $L^3$ is (1–4C)alkylene or carbonyl-(1–3C)alkylene, and, when s is 1, $L^3$ may also be (1–3C)alkylene-carbonyl, and wherein 1 or 2 methylene groups within $L^3$ and the rings formed when $R^5$ and $R^6$ or $R^6$ and $L^3$ are linked optionally bears a substituent selected from the group consisting of oxo, carboxy, (1–4C)alkoxycarbonyl, carbamoyl, N-(1–4C)alkylcarbamoyl, N,N-di-(1–4C)alkylcarbamoyl, pyrrolidin-1-ylcarbonyl, piperidinocarbonyl, morpholinocarbonyl, piperazin-1-ylcarbonyl, 4-(1–4C)alkylpiperazin-1-ylcarbonyl, N-phenylcarbamoyl, N-(1–4C)alkyl-N-phenylcarbamoyl, N-[phenyl-(1–3C)alkyl]carbamoyl, N-(1–4C)alkyl-N-[phenyl-(1–3C)alkyl]carbamoyl, (1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, pyrrolidin-1-ylcarbonyl-(1–4C)alkyl, piperidinocarbonyl-(1–4C)alkyl, morpholinocarbonyl-(1–4C)alkyl, piperazin-1-ylcarbonyl-(1–4C)alkyl, 4-(1–4C)alkylpiperazin-1-ylcarbonyl-(1–4C)alkyl, N-phenylcarbamoyl-(1–4C)alkyl, N-[phenyl-(1–3C)alkyl]carbamoyl-(1–4C)alkyl, hydroxy-(1–4C)alkyl, (1–4C)alkoxy-(1–4C)alkyl and phenyl-(1–4C)alkyl, and wherein any heterocyclic group in said substituent optionally bears 1 or 2 substituents selected from the group consisting of (1–4C)alkyl, (1–4C)alkoxy, carboxy, (1–4C)alkoxycarbonyl, carbamoyl, N-(1–4C)alkylcarbamoyl and N,N-di-(1–4C)alkylcarbamoyl, and wherein any phenyl or phenylene group in $M^3$ optionally bears 1 or 2 substituents selected from the group consisting of halogeno, trifluoromethyl, (1–4C)alkyl and (1–4C)alkoxy;

X is oxy, thio, sulphonyl, sulphonyl or sulphonylamino; and

Q is phenyl, naphthyl, phenyl-(1–4C)alkyl, phenyl-(2–4C)alkenyl, phenyl-(2–4C)alkynyl, (5–7C)cycloalkyl or a heterocyclic moiety containing up to 4 heteroatoms selected from the group consisting of nitrogen, oxygen and sulphur, and Q optionally bears 1, 2 or 3 substituents selected from the group consisting of hydroxy, amino, halogeno, cyano, trifluoromethyl, nitro, carboxy, carbamoyl, formyl, formimidoyl, formohydroximoyl, (1–4C)alkoxycarbonyl, (1–4C)alkyl, (1–4C)alkoxy, N-(1–4C)alkylcarbarnoyl, N,N-di-(1–4C)alkylcarbamoyl, (1–4C)alkylamino, di-(1–4C)alkylamino, (2–4C)alkanoylamino, (2–4C)alkanoyl, (2–4C)alkanoimidoyl, (2–4C)alkanohydroximoyl, phenyl, heteroaryl, phenoxy, phenylthio, phenylsulphinyl, phenylsulphonyl, heteroaryloxy, heteroarylthio, heteroarylsulphinyl, heteroarylsulphonyl, benzyl and benzoyl, and wherein said heteroaryl substituent or the heteroaryl group in a heteroaryl-containing substituent comprises a 5- or 6-membered monocyclic heteroaryl ring containing up to 3 heteroatoms selected from the group consisting of nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1, 2, 3 or 4 substituents selected from the group consisting of halogeno, trifluoromethyl, cyano, trifluoromethoxy, nitro, (1–4C)alkyl, (1–4C)alkoxy, hydroxy, amino, carboxy, carbamoyl, (1–4C)alkoxycarbonyl, N-(1–4C)alkylcarbamoyl, N,N-di-(1–4C)alkylcarbamoyl, (1–4C)alkylamino, di-(1–4C)alkylamino, (2–4C)alkanoylamino and tetrazolyl;

or a pharmaceutically-acceptable salt thereof.

2. A compound of the formula I as claimed in claim 1 wherein each $R^1$ is independently selected from hydrogen, amino, fluoro, chloro, bromo, cyano, methyl, ethyl and methoxy;

$M^1$ is a group of the formula $$NR^2-L^1-T^1R^3$$

in which $R^2$ and $R^3$ together form an ethylene group, $L^1$ is methylene or ethylene, and $T^1$ is CH or N, and wherein 1 or 2 methylene groups within $L^1$ and the ring formed when $R^2$ and $R^3$ are linked optionally bears a substituent selected from the group consisting of methyl and ethyl;

A is a direct link to the carbonyl group or A is methylene;

$M^2$ is a group of the formula $$(T^2R^4)_r-L^2-T^3R^5$$

in which r is 0 or 1,
    $T^2$ is N,
    $T^3$ is N,
    $R^4$ is hydrogen, methyl or ethyl,
    $R^5$ is hydrogen, methyl or ethyl,
    or $R^4$ and $R^5$ together form a methylene, ethylene, trimethylene or methylenecarbonyl group, or $R^4$ is an ethylene group which is linked to a methylene group within $L^2$ forming a 5- or 6-membered ring involving $R^4$ and $T^2$, and
    $L^2$ is methylene, ethylene, trimethylene or methylenecarbonyl,
    and wherein 1 or 2 methylene groups within $L^2$ and the ring formed when $R^4$ and $R^5$ are linked optionally bears a substituent selected from the group consisting of oxo, carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, morpholinocarbonyl, piperazin-1-ylcarbonyl, 4-methylpiperazin-1-ylcarbonyl, methyl, ethyl, carboxymethyl, methoxycarbonylmethyl, ethoxycarbonylmethyl, hydroxymethyl, methoxymethyl and benzyl,
        and wherein the pyrrolidin-1-ylcarbonyl, piperidinocarbonyl, morpholinocarbonyl, piperazin-1-ylcarbonyl or 4-methylpiperazin-1-ylcarbonyl substituent optionally bears a methyl or ethyl substituent;
$M^3$ is a direct link to X, or $M^3$ is a group of the formula $$L^3-(NR^6)_s$$

in which s is 1,
    $R^6$ is hydrogen
    and $L^3$ is carbonylmethylene or carbonylethylene;
X is thio, sulphinyl or sulphonyl; and
Q is phenyl, naphthyl, benzyl, phenethyl, styryl, 2-phenylethynyl, dibenzofuranyl, biphenylyl, pyridylphenyl or pyridylthienyl, and Q optionally bears 1, 2 or 3 substituents selected from the group consisting of hydroxy, amino, fluoro, chloro, bromo, iodo, cyano, trifluoromethyl, nitro, carboxy, carbamoyl, methoxycarbonyl, ethoxycarbonyl, methyl, ethyl, methoxy and ethoxy;
or a pharmaceutically-acceptable salt thereof.

3. A compound of the formula I as claimed in claim 1 wherein each $R^1$ is independently selected from hydrogen, amino, chloro, methyl and ethyl;
    $M^1$ is a group of the formula $$NR^2-L^{11}-T^1R^3$$

in which $R^2$ and $R^3$ together form an ethylene group,
    $L^1$ is ethylene, and
    $T^1$ is CH or N;
A is a direct link to the carbonyl group or A is methylene;
$M^2$ is a group of the formula $$(T^2R^4)_r-L^2-T^3R^5$$

in which r is 0 or 1,
    $T^2$ is N,
    $T^3$ is N,
    $R^4$ is hydrogen, $R^5$ is hydrogen,
    or $R^4$ and $R^5$ together form an ethylene group, or $R^4$ is an ethylene group which is linked to a methylene group within $L^2$ forming a 5- or 6-membered ring involving $R^4$ and $T^2$, and
$L^2$ is methylene or ethylene,
    and wherein 1 or 2 methylene groups within $L^2$ and the ring formed when $R^4$ and $R^5$ are linked optionally bears a substituent selected from the group consisting of carboxy, methoxycarbonyl, ethoxycarbonyl, pyrrolidin-1-ylcarbonyl, piperidinocarbonyl, morpholinocarbonyl, piperazin-1-ylcarbonyl, 4-methylpiperazin-1-ylcarbonyl, methyl, ethyl and benzyl,
    and wherein the pyrrolidin-1-ylcarbonyl, piperidinocarbonyl, morpholinocarbonyl, piperazin-1-ylcarbonyl or 4-methylpiperazin-1-ylcarbonyl substituent optionally bears a methyl or ethyl substituent;
$M^3$ is a direct link to X, or $M^3$ is a group of the formula $$L^3-(NR^6)_s$$

in which s is 1,
    $R^6$ is hydrogen and
    $L^3$ is carbonylmethylene;
X is sulphonyl; and
Q is phenyl, naphthyl, benzyl, phenethyl, styryl, 2-phenylethynyl, dibenzofuranyl, biphenylyl, pyridylphenyl or pyridylthienyl, and Q optionally bears 1 or 2 substituents selected from the group consisting of fluoro, chloro, bromo, iodo, methyl, ethyl, methoxy and ethoxy;
or a pharmaceutically-acceptable salt thereof.

4. A compound of the formula I as claimed in claim 1 wherein
m is 1;
$R^1$ is hydrogen;
$M^1$ is a group of the formula $$NR^2-L^1-T^1R^3$$

in which $R^2$ and $R^3$ together form an ethylene group,
    $L^1$ is methylene or ethylene, and
    $T^1$ is CH or N,
    and wherein 1 or 2 methylene groups within $L^1$ and the ring formed when $R^2$ and $R^3$ are linked optionally bears a substituent selected from the group consisting of methyl and ethyl;
A is a direct link to the carbonyl group or A is methylene;
$M^2$ is a group of the formula $$(T^2R^4)_r-L^2-T^3R^5$$

in which r is 1,
    $T^2$ is N,
    $T^3$ is N,
    $R^4$ is hydrogen, methyl or ethyl,
    $R^5$ is hydrogen, methyl or ethyl,
    or $R^4$ and $R^5$ together form a methylene, ethylene or trimethylene group, or $R^4$ is an ethylene group which is linked to a methylene group within $L^2$ forming a 5- or 6-membered ring involving $R^4$ and $T^2$, and
$L^2$ is methylene, ethylene or trimethylene,
    and wherein 1 or 2 methylene groups within $L^2$ and the ring formed when $R^4$ and $R^5$ are linked optionally bears a substituent selected from the group consisting of oxo, carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, morpholinocarbonyl, methyl, ethyl and benzyl, and wherein the pyrrolidin-1-ylcarbonyl or piperidinocarbonyl substituent optionally bears one or two methyl or ethyl substituents;

$M^3$ is a direct link to X, or $M^3$ is a group of the formula $$L^3-(NR^6)_S$$

in which s is 1,
$R^6$ is hydrogen and
$L^3$ is carbonylmethylene or carbonylethylene;

X is sulphonyl; and

Q is 3- or 4-biphenylyl which optionally bears, in the ring attached to X, 1 or 2 substituents selected from the group consisting of hydroxy, fluoro, chloro, bromo, cyano, trifluoromethyl, methyl, ethyl, methoxy and ethoxy and which optionally bears in the terminal phenyl group up to 4 substituents selected from the group consisting of fluoro, chloro, bromo, trifluoromethyl, cyano, trifluoromethoxy, methyl, ethyl, methoxy and ethoxy;

or a pharmaceutically-acceptable salt thereof.

5. A compound of the formula I as claimed in claim 1 wherein m is 1;

$R^1$ is hydrogen;

$M^1$ is a group of the formula $$NR^2-L^1-T^1R^3$$

in which $R^2$ and $R^3$ together form an ethylene group,
$L^1$ is methylene or ethylene, and
$T^1$ is CH or N, and wherein 1 or 2 methylene groups within $L^1$ and the ring formed when $R^2$ and $R^3$ are linked optionally bears a substituent selected from the group consisting of methyl and ethyl;

A is a direct link to the carbonyl group or A is methylene;

$M^2$ is a group of the formula $$(T^2R^4)_r-L^2-T^3R^5$$

in which r is 1,
$T^2$ is N,
$T^3$ is N,
$R^4$ is hydrogen, methyl or ethyl,
$R^5$ is hydrogen, methyl or ethyl,
or $R^4$ and $R^5$ together form a methylene, ethylene or trimethylene group, or $R^4$ is an ethylene group which is linked to a methylene group within $L^2$ forming a 5- or 6-membered ring involving $R^4$ and $T^2$, and
$L^2$ is methylene, ethylene or trimethylene, and wherein 1 or 2 methylene groups within $L^2$ and the ring formed when $R^4$ and $R^5$ are linked optionally bears a substituent selected from the group consisting of oxo, carboxy, methoxycarbonyl, ethoxycarbonyl, carbamoyl, N-methylcarbamoyl, N,N-dimethylcarbamoyl, pyrrolidin-1-ylcarbonyl, piperidinocarbonyl, morpholinocarbonyl, methyl, ethyl and benzyl, and wherein the pyrrolidin-1-ylcarbonyl or piperidinocarbonyl substituent optionally bears one or two methyl or ethyl substituents;

$M^3$ is a direct link to X, or $M^3$ is a group of the formula $$L^3-(NR^6)_S$$

in which s is 1,
$R^6$ is hydrogen and
$L^3$ is carbonylmethylene or carbonylethylene;

X is sulphonyl; and

Q is benzyl, phenethyl, styryl or 2-phenylethynyl which optionally bears 1, 2 or 3 substituents selected from the group consisting of fluoro, chloro, bromo, cyano, trifluoromethyl, methyl, ethyl, methoxy and ethoxy;

or a pharmaceutically-acceptable salt thereof.

6. A compound of the formula I as claimed in any one of claims 1–5 wherein A is a direct link to the carbonyl group.

7. A compound of the formula I as claimed in claim 1 wherein $M^2$ is a group of the formula $$(T^2R^4)_r-L^2-T^3R^5$$

in which r is 1,
$T^2$ is N,
$T^3$ is N,
$R^4$ is hydrogen or (1–4C)alkyl,
$R^5$ is hydrogen or (1–4C)alkyl,
or $R^4$ and $R^5$ together form a (1–4C)alkylene group and $L^2$ is (1–4C)alkylene.

8. A compound of the formula I as claimed in any one of claims 1–5 wherein $M^3$ is a direct link to X.

9. A compound of the formula I as claimed in claim 1 or claim 2 wherein X is sulphonyl.

10. A compound of the formula I as claimed in claim 1 wherein Q is phenyl, naphthyl or phenyl-(1–4C)alkyl which optionally bears 1, 2 or 3 substituents selected from the group consisting of hydroxy, halogeno, cyano, trifluoromethyl, (1–4C)alkyl, (1–4C)alkoxy, phenyl, phenoxy, phenylthio, phenylsulphinyl, phenylsulphonyl, benzyl and benzoyl, and wherein the phenyl group in a phenyl-containing substituent optionally bears 1 or 2 substituents selected from the group consisting of halogeno, (1–4C)alkyl and (1–4C)alkoxy.

11. A compound as claimed in claim 1 of the formula Ia

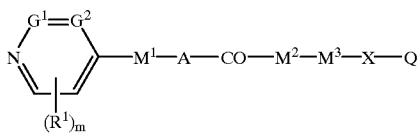

Ia wherein $G^1$ and $G^2$ are CH;

m is 1;

$R^1$ is hydrogen;

$M^1$ is a group of the formula $$NR^2-L^1-T^1R^3$$

in which $R^2$ and $R^3$ together form an ethylene group,

L¹ is ethylene, and
T¹ is CH or N;
A is a direct link to the carbonyl group;
M² is a group of formula $$(T^2R^4)_r\text{—}L^2\text{—}T^3R^5$$

in which r is 1,
T² is N,
T³ is N,
R⁴ is hydrogen,
R⁵ is hydrogen,
or R⁴ and R⁵ together form an ethylene group, and
L² is ethylene,
and wherein 1 methylene group within L² optionally bears a substituent selected from carboxy, ethoxycarbonyl, N-methylcarbamoyl, piperidinocarbonyl, methyl and benzyl;
M³ is a direct link to X, or M³ is a group of the formula $$L^3\text{—}(NR^6)_s$$

in which s is 1,
R⁶ is hydrogen and
L³ is carbonylmethylene;
X is sulphonyl; and
Q is 2-naphthyl which optionally bears 1 or 2 substituents selected from the group consisting of fluoro, chloro, bromo, trifluoromethyl, methyl, methoxy and ethoxy;
or a pharmaceutically-acceptable acid-addition salt thereof.

12. A compound selected from the group consisting of: 2-(2-naphthalenesulphonamido)-N-{1-piperidinocarbonyl-2-[1-(4-pyridyl)-piperidin-4-ylcarbonylamino]ethyl}acetamide, 1-(2-naphthylsulphonyl)-4-[1-(4pyridyl)piperidin-4-ylcarbonyl]-piperazine, 2-(2-naphthalenesulphonamido)-N-(piperidinocarbonyl-2-{2-[1-(4-pyridyl)piperidin-4-yl]acetamido}ethyl)acetamide, 2-(2-naphthalenesulphonamido)-N-(1-piperidinocarbonyl-2-{2-[4-(4-pyridyl)piperazin-1-yl]acetamido}ethyl)acetamide, ethyl 2-(2-naphthalenesulphonamido)-3-[1-(4-pyridyl)piperidin-4-ylcarbonylaamino]propionate, 1-[1-(2-naphthylsulphonyl)piperidin-4-ylcarbonyl]-4-(4-pyridyl)-piperazine, 2-(2-naphthalenesulphonamido)-N-{1-phenyl-3-[1-(4-pyridyl)piperidin-4-ylcarbonylamino]prop-2-yl}acetamide, 4-[1-(4-pyridyl)piperidin-4-ylcarbonyl]-1-[(E)-styrylsulphonyl]-piperazine, 1-[(E)-4-chlorostyrylsulphonyl]-4-[-(4-pyridyl)piperidin-4-ylcarbonyl]piperazine, 1-[(E)-4-methylstyrylsulphonyl]-4-1-(4-pyridyl)piperidin-4-ylcarbonyl]piperazine, 4-[(E)-4-chlorostyrylsulphonyl]-2-methyl-1-[1-(4-pyridyl)piperidin-4-ylcarbonyl]piperazine, 1-(4-biphenylylsulphonyl)-4-[1-(4-pyridyl)piperidin-4-ylcarbonyl]piperazine, 1-(4'-chloro-4-biphenylylsulphonyl)-4-[1-(4-pyridyl)-piperidin-4-ylcarbonyl]piperazine, 1-(7-chloronaphth-2-ylsulphonyl)-4-[1-(4-pyridyl)piperidin-4-ycarbonyl]piperazine, 2-ethoxycarbonyl-4-(2-naphthylsulphonyl)-[1-(1-(4-pyridyl)piperidin-4-ylcarbonyl]piperazine, 1-[(E)-4-fluorostyrrylsulphonyl]-4-[1-(4pyridyl)piperidin-4-ylcarbonyl]piperazine, 1-[(E)-4-bromostyrylsulphonyl]-4-[1-(4-pyridyl)piperidin-4-ylcarbonyl]piperazine, 1-(4'-bromo-4-biphenylylsulphonyl)-4-[(4-pyridyl)piperidin-4-ylcarbonyl]piperazine, 1-(6-chloronaphth-2-ylsulphonyl)-4-[1-(4-pyridyl)piperidin-4-ylcarbonyl]piperazine, 1-(6-bromonaphth-2-ylsulphonyl)-4-[1-(4-pyridyl)piperidin-4-ylcarbonyl]piperazine, 1-(6-chloronaphth-2-ylsulphonyl)-4-[4-(4-pyridyl)piperazin-1-ylcarbonyl]piperazine, 4-(2-naphthylsulphonyl)-2-piperidinocarbonyl-1-[1-(4-pyridyl)piperidin-4-ylcarbonyl]piperazine, 4-(6-chloronaphth-2-ylsulphonyl)-2-ethoxycarbonyl-1-[1-(4-pyridyl)piperidin-4-ylcarbonyl]piperazine, 2-carboxy-4-(6-chloronaphth-2-ylsulphonyl)-1-[1-(4-pyridyl)piperidin-4-ylcarbonyl]piperazine, 4-(6-bromonaphth-2-ylsulphonyl)-2-ethoxycarbonyl-1-[1-(4-pyridyl)-piperidin-4-ylcarbonly]piperazine, 4-(6-bromonaphth-2-ylsulphonyl)-2-carboxy-1-[1-(4-pyridyl)piperidin-4 -ylcarbonyl]piperazine, 4-(6-bromonaphth-2-ylsulphonyl)-2-morpholinocarbonyl-1-[1-(4-pyridyl)piperidin-4-ylcarbonyl]piperazine,
4-(6-chloronaphth-2-ylsulponyl)-2-methoxycabonyl-1-[1-(4-pyridyl)piperidin-4-ylcarbonyl]piperazine, and
2-carboxy-4-(6-chloronaphth-2-ylsulphonyl)-1-[1-(4-pyridyl)piperidin-4-ylcarbonyl]piperazine,
and pharmaceutically-acceptable salts thereof.

13. A compound of the formula I as claimed in claim 1 or claim 3 wherein Q is substituted by fluoro, chloro, bromo or iodo.

14. A compound of the formula I as claimed in claim 1 or claim 7 wherein R¹ is methyl, ethyl, propyl, ioropyl, butyl, isobutyl, sec-butyl or tert-butyl.

15. A pharmaceutical composition which comprises a compound of the formula I or of the formula Ia, or a pharmaceutically-acceptable salt thereof, as claimed in claim 1 or claim 11 together with a pharmaceutically-acceptable diluent or carrier.

16. A method of producing an anticoagulant or antithrombotic effect in a warm blooded animal in need thereof, said method comprising administrating to said animal an anticoagulant or antithrombotic effective amount of a compound according to claim 11.

17. A method of producing a Factor Xa enzyme inhibitory effect in a warm blooded animal in need thereof, said method comprising administering to said animal Factor Xa enzyme inhibitory effective amount of a compound according to claim 11.

18. A method of selectively producing a Factor Xa enzyme inhibitory effect in a warm blooded animal in need thereof, without inhibiting, or inhibiting to a lesser extent, the enzyme thrombin, said method comprising administering to said animal an amount of a compound according to claim 1 which is effective to inhibit Factor Xa enzyme while having no, or a lesser, inhibitory effect on the enzyme thrombin.

19. A method treating a Factor Xa enzyme mediated disease or medical condition in a warm blooded animal in need of such treatment, said method comprising administering to said animal a Factor Xa enzyme inhibitory effective amount of a compound according to claim 1.

20. A method treating a thrombosis mediated disease or medical condition in a warm blooded animal in need of such treatment, said method comprising administering to said animal an antithrombotic effective amount of a compound according to claim 1.

21. A method treating a coagulation disorder in a warm blooded animal in need of such treatment, said method comprising administering to said animal an anticoagulation effective amount of a compound according to claim 1.

22. A method treating a warm blooded animal having a thrombosis or embolism involving Factor Xa mediated coagulation, said method comprising administering to said animal an anticoagulation effective amount of a compound according to claim 1.

23. A method of producing an anticoagulant effect ex vivo in a biological sample suspected to contain Factor Xa enzyme, said method comprising introducing into said biological sample an anticoagulant-effective amount of a compound according to claim 1.

24. The method of claim 23 wherein said biological sample is whole blood.

25. A process for the preparation of an aminoheterocyclic derivative of the formula I or of the formula Ia, or a pharmaceutically-acceptable salt thereof, as claimed in claim 1 or claim 11 which comprises:

(a) for the production of those compounds of the formula I or formula Ia wherein $M^2$ is a group of the formula

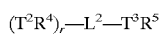

in which $T^2$ is N and r is 1, the reaction of an acid of the formula II, or a reactive derivative thereof,

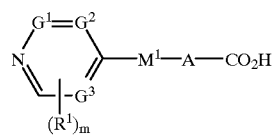

with an amine of the formula

(b) for the production of those compounds of the formula I or formula Ia wherein $M^2$ is a group of the formula

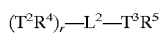

in which T is N, and wherein M is a direct link to X, the reaction of an amine of formula III

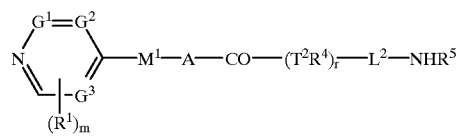

with a compound of the formula Z—X—Q wherein Z is a displaceable group;

(c) for the production of those compounds of the formula I or formula Ia wherein $M^1$ is a group of the formula

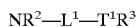

in which $T^1$ is N, and wherein A is a direct link to the carbonyl group, the reaction of an amine of the formula IV

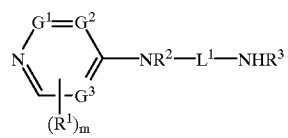

with an acid of the formula

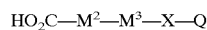

or a reactive derivative thereof, (d) for the production of those compounds of the formula I or formula Ia wherein $M^2$ is a group of the formula

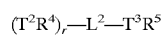

in which $T^3$ is N, and wherein $M^3$ is a group of the formula

in which $L^3$ is carbonylmethylene, the reaction of an amine of the formula III with an acid of the formula

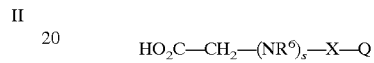

or a reactive derivative thereof, (e) the reaction of a compound of the formula V

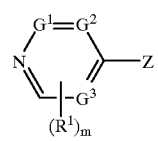

wherein Z is a displaceable group, with an amine of the formula

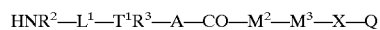

(f) for the production of those compounds of the formula I or formula Ia wherein $M^2$, $M^3$ or Q bears a carboxy or carboxy-containing group, the hydrolysis of a compound of the formula I wherein $M^2$, $M^3$ or Q bears a (1–4C)alkoxycarbonyl group;

(g) for the production of those compounds of the formula I or formula Ia wherein $M^2$, $M^3$ or Q bears a carbamoyl, N-alkylcarbamoyl or N,N-dialkylcarbamoyl group, the reaction of a compound of the formula I wherein $M^2$, $M^3$ or Q bears a carboxy group, or a reactive derivative thereof, with ammonia or an appropriate alkylamine or dialkylamine; or (h) for the production of those compounds of the formula I or formula la wherein Q bears a hydroxy group, the dealkylation of a compound of the formula I wherein Q bears a (1–4C)alkoxy group;

and optionally the reaction of the compound thus obtained with a suitable acid or base using a conventional procedure to form a pharmaceutically-acceptable salt of a compound of the formula I or of the formula la;

and optionally carrying out one of the aforesaid procedures using an optically active starting material, or carrying out a resolution of a racemic form of said compound using a conventional procedure, to obtain an optically active form of a compound of the formula I or of the formula Ia.

* * * * *